US012782271B2

(12) United States Patent
Mercati et al.

(10) Patent No.: US 12,782,271 B2
(45) Date of Patent: Nov. 3, 2026

(54) VALIDATION OF NATURAL MATRICES FOR THERAPEUTIC USE

(71) Applicant: Bios-Therapy, Physiological Systems for Health S.p.A., Sansepolcro (IT)

(72) Inventors: Valentino Mercati, Sansepolcro (IT); Jacopo Lucci, Sansepolcro (IT)

(73) Assignee: Bios-Therapy, Physiological Systems for Health S.p.A., Sansepolcro (IT)

( * ) Notice: Subject to any disclaimer, the term of this patent is extended or adjusted under 35 U.S.C. 154(b) by 0 days.

(21) Appl. No.: 19/430,699

(22) Filed: Dec. 23, 2025

(65) Prior Publication Data

US 2026/0168921 A1 Jun. 18, 2026

Related U.S. Application Data

(63) Continuation of application No. 18/410,096, filed on Jan. 11, 2024, now Pat. No. 12,546,707.

(51) Int. Cl.
*G01N 33/50* (2006.01)
*G01N 21/31* (2006.01)
*G01N 21/359* (2014.01)

(52) U.S. Cl.
CPC ......... *G01N 21/31* (2013.01); *G01N 33/5008* (2013.01)

(58) Field of Classification Search
CPC ........................... G01N 21/31; G01N 33/5008
See application file for complete search history.

(56) References Cited

U.S. PATENT DOCUMENTS

| | | | | |
|---|---|---|---|---|
| 9,315,564 | B2 | 4/2016 | Serraima et al. | |
| 9,987,286 | B2 * | 6/2018 | Goeders .................. | A61P 25/22 |
| 12,546,707 | B2 | 2/2026 | Mercati et al. | |
| 2019/0358280 | A1 * | 11/2019 | Mercati .................. | A61K 36/28 |
| 2021/0333285 | A1 | 10/2021 | Coppe et al. | |
| 2026/0118258 | A1 | 4/2026 | Mercati et al. | |

FOREIGN PATENT DOCUMENTS

| | | | |
|---|---|---|---|
| CA | 2626049 | A1 | 4/2006 |
| CA | 3221031 | A1 | 12/2022 |

OTHER PUBLICATIONS

Conlon et al., "A compendium of kinetic modulatory profiles identifies ferroptosis regulators", Nature Chemical Biology, vol. 17, Jun. 2021, pp. 665-674. (Year: 2021).*
Fakhry, C.T., et al., "Interpreting transcriptional changes using causal graphs: new methods and their practical utility on public networks," BMC Bioinformatics 17(1):318, BioMed Central Ltd., United Kingdom (Aug. 2016).
Felciano, R.M., et al., "Predictive systems biology approach to broad-spectrum, host-directed drug target discovery in infectious diseases," Pac Symp Biocomput 17-28, World Scientific Publishing Company, Singapore (2013).
Kramer, A., et al., "Causal analysis approaches in Ingenuity Pathway Analysis," Bioinformatics 30(4):523-530, Oxford University Press, United Kingdom (Feb. 2014).
Lehn, J.M., "Toward complex matter: supramolecular chemistry and self-organization," Proc Natl Acad Sci USA 99(8):4763-4768, National Academy of Sciences, United States (Apr. 2002).
Martin, F., et al., "Assessment of network perturbation amplitudes by applying high-throughput data to causal biological networks," BMC Syst Biol 6:54, BioMed Central Ltd., United Kingdom (May 2012).
Kremb, S., et al., "Easy-Hit: HIV Full-Replication Technology for Broad Discovery of Multiple Classes of HIV Inhibitors," Antimicrobial Agents and Chemotherapy 54(12):5257-5268, (Dec. 2010).

* cited by examiner

*Primary Examiner* — Shafiqul Haq
*Assistant Examiner* — Nam P Nguyen
(74) *Attorney, Agent, or Firm* — STERNE, KESSLER, GOLDSTEIN & FOX P.L.L.C.

(57) ABSTRACT

The present invention relates to a new method for assessing acceptability ranges or cut-offs for the compliance validation of batches of products comprising or consisting of one or more natural matrix, wherein said products have an ascertained therapeutic or beneficial effect. The invention also relates to a new process for the compliance validation of one or more batches of said products.

10 Claims, 17 Drawing Sheets

| OSTEOARTHRITIS | | STATE OF THE ART | |
|---|---|---|---|
| Hallmarks of the pathology | Biological functions | Pathological state | Healthy physiological state |
| Induction of proliferation | Skeletal and muscular system development and function → articular dysfunction → joint space → **Formation of cartilage tissue** | ↓ | ↑ |
| Reduction of inflammation | Inflammatory disease → inflammation and nociceptions → **Inflammation of joint** | ↑ | ↓ |
| Protection from anatomical damage | Skeletal and muscular system function → difficulty moving a joint → **Non-traumatic arthropathy** | ↑ | ↓ |
| | Organismal injury and abnomalities → joint inflammation and swelling, difficulty moving a joint → **Osteoarthritis** | ↑ | ↓ |

UP modulation
DOWN modulation

Fig. 1

| OSTEOARTHRITIS | | STATE OF THE ART | | TREATMENTS | |
|---|---|---|---|---|---|
| | | | | DISEASE MODEL | CONTROL CARD BATCH |
| Hallmarks of the pathology | Biological functions | Pathological state | Healthy physiological state | IL1β vs untreated | Gold standard batch 2081955 vs IL1β |
| Induction of proliferation | Skeletal and muscular system development and function → articular dysfunction → joint space → **Formation of cartilage tissue** | ↓ | ↑ | -0.20 | 0.15 |
| Reduction of inflammation | Inflammatory disease → inflammation and nociceptions → **Inflammation of joint** | ↑ | ↓ | 0.24 | -0.24 |
| Protection from anatomical damage | Skeletal and muscular system function → difficulty moving a joint → **Non-traumatic arthropathy** | ↑ | ↓ | 0.05 | -0.32 |
| | Organismal injury and abnomalities → joint inflammation and swelling, difficulty moving a joint → **Osteoarthritis** | ↑ | ↓ | 0.04 | -0.31 |

UP modulation
DOWN modulation

Fig. 2

| OSTEOARTHRITIS | | STATE OF THE ART | | TREATMENTS | | | | | | | |
|---|---|---|---|---|---|---|---|---|---|---|---|
| | | | | DISEASE MODEL | REFERENCE DRUG | TRAINING SET | | | | | |
| Hallmarks of the pathology | Biological functions | Pathological state | Healthy physiological state | IL1B vs untreated | Triamcinolone acetonide vs IL1B | Gold standard batch 20B1955 vs IL1B | Batch 20I1279 vs IL1B | Batch 20B0596 vs IL1B | Batch 20J1770 vs IL1B | Batch DEST.21E1640 vs IL1B | Reference Z-score value |
| Induction of proliferation | Skeletal and muscular system development and function → articular dysfunction → joint space → **Formation of cartilage tissue** | ↓ | ↑ | -0.20 | -0.31 | 0.15 | 0.15 | 0.15 | 0.15 | 0.20 | 0.15 |
| Reduction of inflammation | Inflammatory disease → inflammation and nociceptions → **Inflammation of joint** | ↑ | ↓ | 0.24 | -0.26 | -0.24 | -0.33 | -0.33 | -0.33 | -0.32 | -0.24 |
| Protection from anatomical damage | Skeletal and muscular system function → difficulty moving a joint → **Non-traumatic arthropathy** | ↑ | ↓ | 0.05 | -0.17 | -0.32 | -0.33 | -0.30 | -0.31 | -0.08 | -0.17 |
| | Organismal injury and abnormalities → joint inflammation and swelling, difficulty moving a joint → **Osteoarthritis** | ↑ | ↓ | 0.04 | -0.15 | -0.31 | -0.31 | -0.29 | -0.27 | -0.16 | -0.15 |

| |
|---|
| UP modulation |
| DOWN modulation |

Fig. 3

| OSTEOARTHRITIS | | STATE OF THE ART | | TREATMENTS | | | | | | | | |
|---|---|---|---|---|---|---|---|---|---|---|---|---|
| | | | | DISEASE MODEL | REFERENCE DRUG | TRAINING SET | | | | | NEWLY TESTED BATCH | |
| Hallmarks of the pathology | Biological functions | Pathological state | Healthy physiological state | IL1B vs untreated | Triamcinolone acetonide vs IL1B | Gold standard batch 20B1955 vs IL1B | Batch 20I1279 vs IL1B | Batch 20B0596 vs IL1B | Batch 20J1770 vs IL1B | Batch DEST.21E1640 vs IL1B | Batch 21E1640 vs IL1B | Reference Z-score value |
| Induction of proliferation | Skeletal and muscular system development and function → articular dysfunction → joint space → **Formation of cartilage tissue** | ⬇ | ⬆ | -0.20 | -0.31 | 0.15 | 0.15 | 0.15 | 0.15 | 0.20 | 0.15 | 0.15 |
| Reduction of inflammation | Inflammatory disease → inflammation and nociceptions → **Inflammation of joint** | ⬆ | ⬇ | 0.24 | -0.26 | -0.24 | -0.33 | -0.33 | -0.33 | -0.32 | -0.30 | -0.24 |
| Protection from anatomical damage | Skeletal and muscular system function → difficulty moving a joint → **Non-traumatic arthropathy** | ⬆ | ⬇ | 0.05 | -0.17 | -0.32 | -0.33 | -0.30 | -0.31 | -0.08 | -0.25 | -0.17 |
| | Organismal injury and abnormalities → joint inflammation and swelling, difficulty moving a joint → **Osteoarthritis** | ⬆ | ⬇ | 0.04 | -0.15 | -0.31 | -0.31 | -0.29 | -0.27 | -0.16 | -0.30 | -0.15 |

UP modulation
DOWN modulation

Fig. 4

| MILD COGNITIVE IMPAIRMENT | | STATE OF THE ART | |
|---|---|---|---|
| **Hallmarks of the pathology** | **Biological functions** | **Alteration of healthy physiological state** | **Healthy physiological state** |
| Cognition | Neurobiology → Cognition and behavior → **Cognition** | ↓ | ↑ |
| | Neurobiology → Cognition and behavior → Learning and memory → **Learning** | ↓ | ↑ |
| Activation and viability | Neurobiology → Central nervous system → Development of nervous system → **Development of neurons** | ↓ | ↑ |
| | Neurobiology → Development of nervous system → Neurogenesis and neuronal differentiation → Neurogenesis → **Differentiation of neurons** | ↓ | ↑ |
| | Neurobiology → Development of nervous system → Neurogenesis and neuronal differentiation → Neurogenesis → **Proliferation of neuronal cells** | ↓ | ↑ |

| |
|---|
| **UP modulation** |
| **DOWN modulation** |

Fig. 8a

| MILD COGNITIVE IMPAIRMENT | | STATE OF THE ART | |
|---|---|---|---|
| **Hallmarks of the pathology** | **Biological functions** | **Alteration of healthy physiological state** | **Healthy physiological state** |
| Myelination and branching | Neurobiology → Development of nervous system → **Branching of neurons** | ↓ | ↑ |
| | Cell Morphology → **Sprouting** | ↓ | ↑ |
| Reduction of inflammation | Inflammatory disease → **Chronic inflammatory disorder** | ↑ | ↓ |
| Skeletal and muscular system function | Skeletal and muscular system function → Proliferation → **Proliferation of muscle cells** | ↓ | ↑ |
| | Skeletal and muscular disorders → necrosis → **Necrosis of muscle** | ↑ | ↓ |

UP modulation
DOWN modulation

Fig. 8b

| MILD COGNITIVE IMPAIRMENT | | STATE OF THE ART | | TREATMENT<br>CONTROL CARD BATCH |
|---|---|---|---|---|
| **Hallmarks of the pathology** | **Biological functions** | **Alteration of healthy physiological state** | **Healthy physiological state** | **Gold standard batch** |
| Cognition | Neurobiology → Cognition and behavior → **Cognition** | ↓ | ↑ | 2,38 |
| | Neurobiology → Cognition and behavior → Learning and memory → **Learning** | ↓ | ↑ | 2,60 |
| Activation and viability | Neurobiology → Central nervous system → Development of nervous system → **Development of neurons** | ↓ | ↑ | 2,12 |
| | Neurobiology → Development of nervous system → Neurogenesis and neuronal differentiation → Neurogenesis → **Differentiation of neurons** | ↓ | ↑ | 1,83 |
| | Neurobiology → Development of nervous system → Neurogenesis and neuronal differentiation → Neurogenesis → **Proliferation of neuronal cells** | ↓ | ↑ | 2,04 |

| |
|---|
| UP modulation |
| DOWN modulation |

Fig. 9a

| MILD COGNITIVE IMPAIRMENT | | STATE OF THE ART | | TREATMENT<br>CONTROL CARD BATCH |
|---|---|---|---|---|
| Hallmarks of the pathology | Biological functions | Alteration of healthy physiological state | Healthy physiological state | Gold standard batch |
| Myelination and branching | Neurobiology → Development of nervous system → **Branching of neurons** | ↓ | ↑ | 1,22 |
| | Cell Morphology → **Sprouting** | ↓ | ↑ | 2,03 |
| Reduction of inflammation | Inflammatory disease → **Chronic inflammatory disorder** | ↑ | ↓ | -1,48 |
| Skeletal and muscular system function | Skeletal and muscular system function → Proliferation → **Proliferation of muscle cells** | ↓ | ↑ | 2,05 |
| | Skeletal and muscular disorders → necrosis → **Necrosis of muscle** | ↑ | ↓ | -2,14 |

UP modulation
DOWN modulation

Fig. 9b

| OSTEOPOROSIS | | STATE OF THE ART | |
|---|---|---|---|
| **Hallmarks of the pathology** | **Biological functions** | **Alteration of healthy physiological state** | **Healthy physiological state** |
| Remodelling of bone | Skeletal and Muscular System Development and Function → Remodelling → **Remodelling of bone** | ↑ | ↓ |
| | Skeletal and Muscular System Development and Function → Remodelling → **Resorption of bone** | ↑ | ↓ |
| Osteoporosis | Skeletal and Muscular Disorders → Osteoporosis → **Osteoporosis** | ↑ | ↓ |
| Differentiation of osteoblasts | Increased Levels of Alkaline phosphatase → Activation → **Increased activation of alkaline phosphatase** | ↓ | ↑ |
| | Connective Tissue Development and function → Differentiation → **Differentiation of bone cells** | ↓ | ↑ |
| | Skeletal and Muscular System Development and Function → Differentiation → **Differentiation of osteoblasts** | ↓ | ↑ |

UP modulation
DOWN modulation

Fig. 10a

| OSTEOPOROSIS | | STATE OF THE ART | |
|---|---|---|---|
| Hallmarks of the pathology | Biological functions | Alteration of healthy physiological state | Healthy physiological state |
| Mineralization | Skeletal and Muscular System Development and Function → Mineralization → **Mineralization of bone cell lines** | ↓ | ↑ |
| | Skeletal and Muscular System Development and Function → Mineralization → **Mineralization of osteoblasts** | ↓ | ↑ |
| | Skeletal and Muscular System Development and Function → Formation → **Formation of bone** | ↓ | ↑ |
| Reduction of inflammation | Inflammatory Response → Inflammation → **Inflammation of adipose tissue** | ↑ | ↓ |
| | Inflammatory Response → Inflammation → **Inflammation of connective tissue** | ↑ | ↓ |
| | Inflammatory Response → Inflammation → **Inflammation of white adipose tissue** | ↑ | ↓ |
| Reduction of bone adipose tissue | Connective Tissue Development and Function → Quantity → **Quantity of adipose tissue** | ↑ | ↓ |
| | Nutritional Disease → Weight gain → **Weight gain** | ↑ | ↓ |
| | Connective Tissue Development and Function → Transdifferentiation → **Transdifferentiation** | ↓ | ↑ |
| | Connective Tissue Development and Function → Differentiation → **Differentiation of adipocytes** | ↑ | ↓ |

UP modulation
DOWN modulation

Fig. 10b

| OSTEOPOROSIS | | STATE OF THE ART | | TREATMENT<br>CONTROL CARD BATCH |
|---|---|---|---|---|
| Hallmarks of the pathology | Biological functions | Alteration of healthy physiological state | Healthy physiological state | Gold standard batch |
| Remodelling of bone | Skeletal and Muscular System Development and Function → Remodelling → **Remodelling of bone** | ↑ | ↓ | -0,49 |
| | Skeletal and Muscular System Development and Function → Remodelling → **Resorption of bone** | ↑ | ↓ | -0,49 |
| Osteoporosis | Skeletal and Muscular Disorders → Osteoporosis → **Osteoporosis** | ↑ | ↓ | -0,31 |
| Differentiation of osteoblasts | Increased Levels of Alkaline phosphatase → Activation → **Increased activation of alkaline phosphatase** | ↓ | ↑ | 0,19 |
| | Connective Tissue Development and function → Differentiation → **Differentiation of bone cells** | ↓ | ↑ | 0,37 |
| | Skeletal and Muscular System Development and Function → Differentiation → **Differentiation of osteoblasts** | ↓ | ↑ | 0,39 |

| |
|---|
| UP modulation |
| DOWN modulation |

Fig. 11a

| OSTEOPOROSIS | | STATE OF THE ART | | TREATMENT<br>CONTROL CARD BATCH |
|---|---|---|---|---|
| Hallmarks of the pathology | Biological functions | Alteration of healthy physiological state | Healthy physiological state | Gold standard batch |
| Mineralization | Skeletal and Muscular System Development and Function → Mineralization → **Mineralization of bone cell lines** | ↓ | ↑ | 0,29 |
| | Skeletal and Muscular System Development and Function → Mineralization → **Mineralization of osteoblasts** | ↓ | ↑ | 0,34 |
| | Skeletal and Muscular System Development and Function → Formation → **Formation of bone** | ↓ | ↑ | 0,17 |
| Reduction of inflammation | Inflammatory Response → Inflammation → **Inflammation of adipose tissue** | ↑ | ↓ | -0,46 |
| | Inflammatory Response → Inflammation → **Inflammation of connective tissue** | ↑ | ↓ | -0,46 |
| | Inflammatory Response → Inflammation → **Inflammation of white adipose tissue** | ↑ | ↓ | -0,38 |
| Reduction of bone adipose tissue | Connective Tissue Development and Function → Quantity → **Quantity of adipose tissue** | ↑ | ↓ | -0,29 |
| | Nutritional Disease → Weight gain → **Weight gain** | ↑ | ↓ | -0,49 |
| | Connective Tissue Development and Function → Transdifferentiation → **Transdifferentiation** | ↓ | ↑ | 0,28 |
| | Connective Tissue Development and Function → Differentiation → **Differentiation of adipocytes** | ↑ | ↓ | -0,45 |

| |
|---|
| UP modulation |
| DOWN modulation |

Fig. 11b

| OSTEOARTHRITIS | | STATE OF THE ART | | | TREATMENTS | | | | | |
|---|---|---|---|---|---|---|---|---|---|---|
| | | | | | REFERENCE STANDARD | DISEASE MODEL | TRAINING SET | | | |
| Hallmarks of the pathology | Biological functions | Pathological state | Healthy physiological state | Untreated cells | Ascorbic acid + AAPH (ROS %) | AAPH (ROS %) | Gold standard batch 2081955 + AAPH (ROS %) | Batch 2011279 + AAPH (ROS %) | Batch 2011770 + AAPH (ROS %) | 2080596 + AAPH (ROS %) |
| Reduction of inflammation | Free radical scavenging→biosynthesis→ **oxidative stress** | ↑ | ↓ | 18 | 17 | 100 | 17 | 17 | 17 | 21 |

| |
|---|
| UP modulation |
| DOWN modulation |

Fig. 12

VALIDATION OF NATURAL MATRICES FOR THERAPEUTIC USE

CROSS-REFERENCE TO RELATED APPLICATIONS

This application is a continuation of U.S. application Ser. No. 18/410,096, filed on Jan. 11, 2024, which is incorporated herein by reference in its entirety.

The present invention relates to new batch control methods for products comprising or consisting of a natural matrix or mixtures of vegetal matrices, said products being characterised by the fact that the matrix or matrices themselves show distinctive emerging properties different from those represented by the sum of the properties of their individual components.

STATE OF THE ART

The historical concept under which patents are granted for the benefit of the public, particularly in matters of health and safety, has roots that date back centuries. The underlying principle is that, while patents provide inventors with a temporary monopoly on their creations, the ultimate aim is to serve the greater good of society.

In contemporary times, this historical concept is reflected in various legal provisions and policies that govern patents. It underscores the understanding that while inventors deserve recognition and protection for their contributions, society as a whole should ultimately benefit from these innovations, particularly in areas critical to public health and safety.

In other words, the humanitarian basis of the patent system lies in its goal to strike a balance between fostering innovation and ensuring that the benefits of that innovation are shared for the betterment of society as a whole. In particular, the patent system should ensure a knowledge sharing and the promotion of progress for the scope indicated above.

In particular, the patent system can play a crucial role in addressing humanitarian and global challenges. For instance, it can incentivize the development of sustainable medicines, environmentally sustainable technologies, and solutions for pressing issues like clean energy and water scarcity.

From the beginning of the 16th century until today, in particular in the field of medical and beneficial products, has been possible to standardise, and hence to validate only artificial substances produced with chemically definable alchemical processes.

This path, which although very reductionist has proven to be of great value, allowing many diseases to be eradicated in the past 5 centuries, is now encountering its limits, which derive from the extraneous nature of chemical substances to vital processes.

Concerning the development of new sustainable medicaments, it is now also ascertained that artificial (in particular, chemically synthesised) therapeutical products are generating harmful impacts on biodiversity and native immune systems.

It is well known that synthetic APIs can enter ecosystems through various routes, primarily through the discharge of pharmaceutical waste from manufacturing plants and improper disposal of unused or expired medications. This can lead to bioaccumulation of artificial and poorly biodegradable substances in aquatic and terrestrial organisms, potentially disrupting food chains and threatening biodiversity.

Studies have shown adverse effects on aquatic organisms, such as altered behaviour, reproduction, and even mortality, as a result of exposure to synthetic APIs. (Boxall, A. B. et al (2012). Pharmaceuticals and personal care products in the environment: what are the big questions?. Environmental health perspectives, 120 (9), 1221-1229); Fick, J., & Lindberg, R. H. (2015). Tysklind, M. and Larsson, D. G. J. (2015). Predicted critical environmental concentrations for 500 pharmaceuticals. Regulatory Toxicology and Pharmacology, 73 (1), 607-616.)

It is well known that many synthetic APIs are designed to be biologically active and particularly stable, which, as a result, can hinder their natural degradation processes. Consequently, these molecules persist in the environment for extended periods, potentially accumulating in soils and waters. This reduced biodegradability raises concerns about long-term environmental impacts and the potential for bioaccumulation in organisms [Kasprzyk-Hordern, B., et al (2008). The removal of pharmaceuticals, personal care products, endocrine disruptors and illicit drugs during wastewater treatment and its impact on the quality of receiving waters. Water research, 43 (2), 363-380; Verlicchi P., et al (2012). Occurrence of pharmaceutical compounds in urban wastewater: Removal, mass load and environmental risk after a secondary treatment—A review. Science of the total environment, 429, 123-155].

Furthermore, there is growing concern about the potential effects of synthetic APIs on human and animal immune systems. Some pharmaceuticals have been found to interfere with immune function, either directly or indirectly, leading to altered immune responses or increased susceptibility to infections. This can have significant implications for both individual health and population-level immunity [Vos T. et al (2016). Global, regional, and national incidence, prevalence, and years lived with disability for 310 diseases and injuries, 1990-2015: a systematic analysis for the Global Burden of Disease Study 2015. The Lancet, 388 (10053), 1545-1602; Calabrese, E. J., & Baldwin, L. A. (2003). Toxicology rethinks its central belief. Nature, 421 (6924), 691-692].

In conclusion, while synthetic APIs have undoubtedly contributed to advancements in healthcare, their environmental and health impacts should be carefully considered. Efforts to develop greener pharmaceuticals, improve waste management, and monitor environmental contamination are crucial steps towards mitigating these concerns.

In addition, it has to be noted that, while being chemically analogous to their synthetic counterparts if taken in isolation, natural molecules within a natural matrix are likely to possess distinct fingerprints with respect to their synthetic analogues, due to the totally different synthetic pathway in terms of primary metabolites, reactants, reaction temperatures, energy sources, catalysts etc., potentially influencing their physicochemical behaviour and reactivity, therefore their biological activity.

According to the conventional paradigm, from a chemical-structural viewpoint, the identity of a molecule is embedded in its atomic composition and the geometric arrangement thereof. By way of example, estragol (1-allyl-4-methoxybenzene), which in nature is prominently identified in essential oils such as those derived from *Ocimum basilicum* and *Artemisia dracunculus* is known in the art for its potential aromatic and medicinal application. The molecular constitution and associated energy states of estragol, contingent upon its origin, have been a subject of robust scientific deliberation. While traditional perspectives postulate uniform molecular attributes, a more rigorous scrutiny suggests nuanced differences.

Given this premise, estragol, whether procured from botanical sources via distillation or synthesized in laboratory confines, should ideally be congruent in its inherent physicochemical attributes.

However, it's paramount to distinguish between the pathways of production. In botanical matrices, biosynthesis of estragol is orchestrated by a series of enzymatic reactions, commencing with primary metabolites, and culminating in this specific secondary metabolite. It is known in the art that each of these enzymatic transformations operates within a distinct energy landscape, potentially conferring to the molecule a unique energy state.

Conversely, the laboratory synthesis of estragol hinges on chemical reactions steered by different precursors and conditions (such as temperatures not compatible with the life of a plant). The energy dynamics of such synthetic routes, governed by the thermodynamics and kinetics intrinsic to the reactions, are highly likely to deviate from the plant-mediated enzymatic pathways.

In addition, it is evident that also the isotopic abundances resulting from the two different pathways (natural and synthetic) are unlikely to be the same. Isotopic abundances, even if subtly varied, are known to exert tangible influences on vibrational frequencies, bond strengths, and consequentially, the energy states of the molecule itself [Bigeleisen, J. (1996). Nuclear spin conversion in polyatomic molecules. Journal of Chemical Physics, 105 (18), 8121-8129]. Given the likely isotopic disparities between botanical sources and synthetic reagents, the resultant estragol molecules are likely to harbour differential energy imprints and biological activities. In the light of the above, while being chemically analogous, molecules from natural and synthetic origins are reasonably likely to possess distinct energetic fingerprints, potentially influencing their physicochemical properties, reactivity and therefore their biological activity. Indeed, the difference between the activity of synthetic and natural estragol has been reported in the art (Suzanne M. F. et al. "Basil extract inhibits the sulfotransferase mediated formation of DNA adducts of the procarcinogen l'-hydroxyestragole by rat and human liver S9 homogenates and in HepG2 human hepatoma cells" Food and Chemical Toxicology, 2008, 46 (6) 2296-2302, https://doi.org/10.1016/j.fct.2008.03.010.).

In addition, synthetic molecules (intended as molecules obtained through a production carried out by man through chemical synthesis laboratory/industrial processes) are designed in order to provide the desired interaction with a specific given target molecule, said design not taking into account all the interactions that the said molecule may and will have within a natural matrix, with the environment, and with the whole receiving network of the organism in which they will be used. On the other hand, native biosynthesised molecules, being produced in natural, non-artificial settings, will intrinsically carry all the essential features in order to exist and exert their functions in an epigenetically determined contest whose description is inaccessible when a conventional deterministic chemical approach is used. A possible deciphering of natural matrices and biosynthesised molecules may be provided applying quantum biology.

Products obtained from natural sources have been used for thousands of years to prevent and cure human diseases. In this context, a large number of studies have been limited to characterizing their chemical composition at the monomolecular level and the monomolecular activities, while the spontaneous assemblies, interactions and supramolecular organisation of all the components in said natural products have not been fully investigated and thus understood. Since the development of modern chemistry, the reductionist approach focusing on the isolation of single molecules from natural products and the subsequent artificial synthesis of molecules of therapeutic interest, the aim has been to develop selected active principles that act on a given target following the key-lock paradigm.

This had led to the conviction that research in the field of life sciences was to be aimed at substances that can be chemically validated, with data such as quantities of the individual substances at a molecular level, generating very powerful and effective artificial products, with linear dynamics. It is now becoming evident that this direction is also generating harmful impacts on biodiversity and native immune systems.

The inability to standardise products deriving from natural sources, including, in particular, products that are prepared by humans, but that consist mainly or only of components originating from natural raw (starting) sources i.e. that consist 100% of non-artificial matter, has been one of the major difficulties for technology, thereby opening the doors to the current API-based, pharmacological approach in order to ensure the batch to batch validation of products deriving from natural sources intended for medical or beneficial application.

By way of example, natural matrices, such as plant matrices, are complex systems characterized by a large number of molecular components belonging to different phytochemical classes that interact with each other already in the plant in order to determine the plant's biology. This interaction continues also in the processing phases and different processing techniques affect the post-processing interactions of said components. These compounds can interact at the functional and structural level. Supramolecular aggregates as well as their chemical-physical and structural characteristics that result in both structural and functional networks are dynamic interactions and can be modulated by environmental conditions and, as one can expect, these interactions affect the reactivity of the individual components and, through the so called "matrix effect", result in properties typical of the distinct entity represented by the matrix and are different from the sum of the properties of its single molecular components. Such properties are defined as "emerging properties". This phenomenon has been described and attributed specifically to living matter, which has a drive to self-assemble and self-organize to form supramolecular complex entities [Jean-Marie Lehn Toward complex matter: Supramolecular chemistry and self-organization. PNAS, 2002, 99 (8) 4763-4768 https://doi.org/10.1073/pnas.072065599]. This inherent complexity leads to the fact that individual molecules within a natural matrix cannot be considered to be contained in isolated and fixed packages, as mutual non-covalent and dynamic interactions continuously occur between them. Such interactions are intra- and intermolecular and occur both among molecules of the same type as well as among molecules belonging to different chemical classes. This introduces the need to consider that the ability of a natural matrix to exert a therapeutic activity on the human body depends not only on the quali-quantitative composition of the matrix, which is by its own nature prone to be variable per se, but also on the presence of such interactions between same and different molecules, including small molecules as well as more complex ones such as proteins, polysaccharides, lipids, RNA, etc.

In this context, it is clear that the classical validation of therapeutic products based on the pharmacological relationship between structure and activity (SAR) which is the most relevant relationship in classical pharmacological activities between an active pharmaceutical ingredient (API) and the receptor targeted by said API, which is considered at the level of single molecules, is unlikely to be respected across different batches of the same natural matrix.

These considerations appear to profoundly distinguish the study of the interaction between a self-assembled natural matrix and a biological system, imbued with complexity at the molecular and supramolecular level, from the interaction which would be established by an API and its target receptor cellular structure. In fact, the latter is unequivocally defined by the exquisitely deterministic canons of the key-lock mechanism by fixing, also and above all in structural terms defined in both a quantitative and qualitative manner the interaction between the API and its specific target. This concept is so pervasive from a conceptual point of view that it then translates into the possibility of controlling the reproducibility of the biological activity of the API through the sole control of the reproducibility of its molecular structure based on their structure-activity relationship (SAR). This is evidently not applicable to natural matrices or products comprising them, due to the characteristics discussed above.

It therefore appears necessary to note fundamental differences between natural self-assembled matrices and APIs:

the first, which are eubiotic with respect to man and the environment, are characterized by a physiological interconnection at the molecular level with the receiver's biological system and, precisely by virtue of their complexity, are clearly inappropriately described and characterised through the use of deterministic tools such as the key-lock model;

the latter, which are xenobiotes with respect to man and the environment, are instead characterized by the clear possibility of describing their interaction with the receiver's biological system according to totally deterministic canons, typically summarized by the "key and lock" model.

Therefore, knowledge of the identity and amount of each and every molecule in a natural matrix is not sufficient to predict the dynamic and kinetic properties, as well as the therapeutic effectiveness, of the matrix itself. The opposite happens when selected single molecules, such as APIs, are considered, whereby the SAR, the pharmacodynamic and pharmacokinetic properties are intrinsically related to the chemical identity of the active principle, and to the pharmacodynamic inertia of the excipients. For this reason, the canonical concepts of pharmacodynamics and pharmacokinetics make sense solely when referring to a single molecule (the active principle), or a representative thereof (a functional marker).

The network established among all components of the matrix yielding "the matrix effect" makes it impossible to identify a single marker as representative of the network, because no single component is capable of conveying alone all of the properties specific to the matrix, since no single component reflects the interaction between the matrix and the target living organism.

The matrix effect confers the specific and unique properties of the matrix itself or of a mixture of matrices that result in a new different matrix, called emergent properties, which cannot be reconducted to the properties of any of the components taken in isolation. This reflects perfectly the impossibility to correctly study such properties through deterministic chemical methods, commonly used in classical pharmacological chemistry, which, as said above, are well adequate only for single active principles and excipients in pharma settings.

Rather, the dynamic and kinetic behaviour of the matrix is the result of the dynamic network of interactions taking place within the matrix, showing:

the presence of a great number of components, the inability to reconduct the properties of the matrix to the sum of the properties of the single substances the impossibility to describe the interaction between the matrix and the receiving organism according to the key-lock paradigm (model), which is the foundation of SAR.

At present, human beings are becoming aware that the response to most problems lies in nature itself, and that there is the need of developing processes and methods that allow to understand, and therefore somehow standardise, natural complex entities self-organizing their supramolecular networks, such as natural matrices. These entities are the only ones physiologically compatible with everything that forms creation. Therefore, the need of moving from the Enlightenment-reductionist based validation to a probabilistic approach inspired to the latest evolutions in scientific thinking, thus eventually opposing linear dynamics to circular dynamics. The deterministic chemical approach is therefore not adequate to investigate and monitor matrix properties and quality. Approaches that assess the interactions within complex systems are necessary, in order to allow, as required, the identification of the features relevant for the reproducibility of the therapeutic properties of the matrix.

Hence the need to turn to approaches inspired by Systems Theory.

The study of such properties, previously not achievable, requires tools such as the "omics" sciences, among which transcriptomics and metabolomics can be identified as of pivotal importance.

Concerning products comprising or consisting of natural matrices, having a therapeutic effect, it is herein reminded that the Medical Device (MD) EU Regulation 2017/745 (Regulation) was officially published in Europe May on 5th, 2017 [REGULATION (EU) 2017/745 OF THE EUROPEAN PARLIAMENT AND OF THE COUNCIL of 5 Apr. 2017 on medical devices, amending Directive 2001/83/EC, Regulation (EC) No 178/2002 and Regulation (EC) No 1223/2009 and repealing Council Directives 90/385/EEC and 93/42/EEC] and introduced a completely new governance into all aspects of the lifecycle of a MD.

The term Medical Device, according to the Regulation, comprises products which do achieve a therapeutic effect but not with a pharmacological, immunological or metabolic (Ph.IM) mode of action (MOA). The Ph.I.M MOA is the mode of action characterized by a key-lock model where the selected API obeys the rules of SAR and acts on its target receptor. Thus, products comprising or consisting of complex systems such as natural matrices can comply with the Regulation. In particular, the Regulation also indicates that a product which modifies a pathological or physiological state or process through a non-Ph-IM mechanism of action is a MD.

Therefore, the Regulation poses a double problem to be solved: on one side, MDs consisting of materials of natural origin, such as plant matrices and the like, need to undergo a quality control validation in order to be available for therapy, on the other side, there is the need to demonstrate that the therapeutic effect of said products is achieved by means of non-Ph-IM mechanisms of action.

The current validation of products for therapeutic use, based exclusively on reproducibility of their chemical composition, is applicable exclusively to products acting with a Ph-IM mechanisms of action.

Although taking in account the complexity of the natural matrices, the present state of the art is based on the validation of products comprising or consisting of natural matrices for use in the treatment of a pathological condition (i.e. a product falling within the definition of MD according to EU Regulation) at the chemical level as for APIs. This is in striking contrast with the intimate nature of such products for all the reasons provided above. There is hence the need in the art to develop validation procedures that are based on the acknowledgement of said complexity and that are not limited to the evaluation of the reproducibility of such products based uniquely on their molecular composition. In addition, the present state of the art does not provide methods for the assessment of the mechanism of action of said product.

There is at present a strongly felt need in finding alternatives to the traditional pharmacology but at the same time guaranteeing the validation and standardization of products, comprising or consisting of one or more natural matrix, used for therapeutic purposes.

The provision of methods validating the quality of a product comprising or consisting of natural matrices that are not based on the mere chemical composition thereof, would allow the use in therapy of products of natural origin, having a circular dynamic rather than a linear one, i.e. acting on the overall physiological state altered by a pathological condition rather than on a single alteration. This would result in the development of new research fields and in the possibility of using a whole network (such as a natural matrix) in therapy, said network operating on the network represented by the receiving treated subject i.e. with a circular dynamic rather than a single compound, acting on a single point of the receiving network i.e. with a linear dynamic.

The present invention solves the first problem summarised in the paragraph above.

SUMMARY OF THE INVENTION

The present invention provides a new method for defining the acceptability ranges or cut-offs of a spectroscopy or spectrophotometry analysis for the validation of one or more batches of a product, for use in the treatment of a pathological condition, comprising or consisting of one or more natural matrix; comprising a step in which said acceptability ranges or cut-offs are calculated on the spectroscopy or spectrophotometry spectra of a gold standard of said product, said gold standard having an ascertained therapeutic effect in the treatment of said pathological condition, and of one or more different batches of said product, wherein said spectra are defined as acceptable or not acceptable on the basis of selected biological activities exerted in at least one cellular-based assay by said gold standard and said one or more different batches on one or more hallmarks of said pathological condition and not on the mere chemical composition thereof.

In other words, the acceptability ranges or cut-offs are defined on the basis of the deviation of said aforementioned spectra from the average spectrum obtained from them.

The products that can be validated with the method of the invention are preferably prepared according to good manufacturing practices, hence following standardised procedures in order to obtain a priori a high degree of homogeneity between batches despite the fact that they contain or consist of natural matrices and are therefore obtained from natural products.

As disclosed above, due to the complex interactions within natural matrix or matrices and therapeutic or beneficial (for health) products comprising or consisting of said matrices and the impossibility to ascribe the therapeutical or beneficial effects to specific APIs, there is a clear need in the art, not only for a best practice and standardisation through the whole process of preparation of eubiotic products comprising or consisting of natural matrices, but also for a batch control model of said products that is not based on the identification, quantification and evaluation of the individual chemical entities contained in said matrix or matrices as their therapeutic or beneficial emerging properties are not ascribable to the mere sum of the properties of their individual components of said matrix or matrices. This control model should therefore take into account the whole system, allowing batch assessment within context of mutual interactions among all components. This different assessment method is necessary because the properties (emerging properties) of products comprising or consisting of a natural matrix or matrices, in particular a vegetal matrix, an animal matrix or mixtures thereof are due to the very interconnection among all the components of the natural matrices present in this kind of products. This means that, as explained above, as opposed to classical pharmaceutical products, whose activity is defined by a specific API, it is not possible to ascribe the emerging properties typical of natural matrices to a single or few components functional interactions. Indeed, the properties of a natural matrix stem not only from each and every single component therein but also from the supramolecular interconnection among said components including the way said components self-assemble themselves at the supramolecular level, which results in a network of interactions among all the components of the matrix. In other words, in products comprising or consisting of a natural matrix there is not an “active principle” responsible for the therapeutic features of the product, or “excipients” responsible for not interfering with the features of the active principle, as in a typical pharmaceutical product, but there are multiple interconnected and interacting components which are all responsible for the emergent properties of the matrix. “Emergent” is the term most often used to describe the observed integrated features of a system.

Characteristic is also the interaction between the natural matrix and the receiving organism, by way of example, the human body i.e. interactions between the donor network (the matrix or natural material according to the specification) and the receiving network (the body of the subject to whom the product is administered e.g.: the human body). Such interactions bring to the modification of a multitude of interconnected biological pathways in a way that is distinctive of each biological matrix. As opposed to specific APIs, the effect of a therapeutical product comprising or consisting of one or more natural matrix is broad and encompasses so many aspects of the physiology, that the result is that the product affects the overall pathological state rather than modifying a single function contributing to the pathological state. The modification of the overall pathological state is the result of the multitude of biological components constituting the natural material consisting of or comprising one or more natural matrix (i.e. the product), acting in a coordinated way (i.e. emergent properties or matrix effect) by means of both functional and structural interactions.

As discussed above, it is herein also reminded that, while being chemically analogous to their synthetic counterparts if taken in isolation, natural molecules within a natural matrix are likely to possess distinct fingerprints with respect to their synthetic analogues, due to the totally different synthetic pathway in terms of primary metabolites, reactants, reaction temperatures, energy sources, catalysts etc., potentially influencing their physicochemical behaviour and reactivity, therefore their biological activity.

For the reasons depicted above, a preferred standardised eubiotic protocol is used for the production of the natural matrices, in particular plant matrices and of the final products to be validated with the methods of the invention. The eubiotic protocol preferably starts from the agricultural production to the final transformation of raw sources designed such as to preserve the basic natural programmatic rules, which have allowed the interconnection between all the components of living things, organic and inorganic, for millions of years is provided herein.

The Applicant's research disclosed herein demonstrates that the classical approach used for standard pharmaceutical products (i.e. quali-quantitative characterisation of the matrix) is not applicable to products providing therapeutic and/or health benefits, when the product comprises or consists of complex natural systems (i.e. natural matrices). As known in the art, one of the major problems linked to the validation of therapeutical product comprising or consisting of one or more natural matrix, lies in that a natural matrix extracted, e.g. from a given plant, is never totally identical to "the same" natural matrix extracted in the same way from another plant of the same species or even variety, from the point of view of the molecular components.

Due to the very nature of natural matrices, contrary to the classical quality control acceptance parameters used for classical pharmaceutical products based on a specific API rule, a degree of variability in the quali-quantitative composition of products comprising or consisting of natural matrices, must be tolerated as a manifestation of the most intimate nature of such entities and their mode of action on the receiving organism; the problem is however to identify how to assess said acceptable degrees of variability.

The present application provides a new and reliable method for assessing spectroscopy or spectrophotometry acceptability ranges or cut-offs suitable for the quality processes of products, comprising or consisting of complex natural systems, having a therapeutic or healthy effect the acceptability ranges or cut-offs being based on the biological activities of said kind of products on hallmarks of a given pathological state rather than on the quali-quantitative analysis of specific chemical substances in said products.

The authors of the present invention, surprisingly found that, notwithstanding the quali-quantitative differences among natural matrices obtained from different members of the same source (even through the same production procedures), the different molecular entities in said matrices appear to act in a redundant manner with each other both functionally and structurally. This redundance results in a clear maintenance of the biological activity exercised by products comprising or consisting of natural matrices even when the quali-quantitative composition of different batches of said products would not be considered acceptable using classical batch control protocols at present demanded by the legislations designed to regulate deterministically acting APIs. Without being bound to theories, the observed maintenance of the biological activity is likely due to the fact that, as said above, the emerging properties of a natural matrix are due to the matrix network acting as a whole entity with distinctive properties, and may not be ascribable to each single molecule as if it were in isolation.

The inventors have hence discovered that different batches of products comprising or consisting of complex natural systems, that, according to the common standard quality control validation techniques based on their quali-quantitative compositions resulted in a determination of non-compliance, surprisingly maintained equivalent biological effects resulting in their desired biological activity notwithstanding their different composition.

Therefore, for therapeutic products comprising or consisting of one or more natural matrix, instead of basing the acceptability ranges or cut-offs of the quality control on the identification and evaluation of selected individual chemical entities, and/or performing statistical preclearing of spectroscopy data in order to discard outliers classically accepted for APIs, the applicant developed a new method that bases the assessment of quality control parameters, for validating different batches said product, on the analysis of selected parameters that are representative of its biological effect, which is the pivotal feature of a medical device constituted by natural matrices. The assessment of the acceptability ranges or cut-offs and validation method herein provided, are adequate for the quality control of biological material with therapeutic activity as defined by Regulation 2017/745, reflect product conformity to GSPR 1 of Annex I of said Regulation, specifically in the first lines reciting: "Devices shall achieve the performance intended by their manufacturer and shall be designed and manufactured in such a way that, during normal conditions of use, they are suitable for their intended purpose".

The present invention therefore provides a method for defining the acceptability ranges or cut-offs of a spectroscopy or spectrophotometry analysis for the quality validation of one or more batches of a product for use in the treatment of a pathological condition comprising or consisting of one or more natural matrix; comprising a step in which said acceptability ranges or cut-offs are calculated on the spectroscopy or spectrophotometry spectra of a gold standard having an ascertained therapeutic effect in the treatment of said pathological condition and one or more batches of said product wherein said spectra are defined as acceptable or not acceptable on the basis of the biological activities exerted by said gold standard and one or more batches of said product on one or more hallmarks of said pathological condition in at least one cell-based assay.

The invention further provides a method for assessing, among different batches, a gold standard of a product for use in the treatment of a pathological condition, comprising one or more natural matrix, as defined in the claims. The invention also provides a process for the validation (i.e. quality control compliance) of one or more batches of a product for the treatment of a pathological condition, said product comprising one or more natural matrix, comprising the following steps:

a. carrying out a spectroscopy or spectrophotometry analysis of each batch,
b. validating each batch wherein the obtained parameters fall within the ranges or cut-offs identified according to the method of the invention for said spectroscopy or spectrophotometry analysis.

Glossary

A "natural matrix" in the present application refers to a material consisting of a network represented by a broad number of components/constituents obtained (e.g. extracted)

directly from a member of the natural kingdom or a naturally occurring portion thereof (i.e. from a natural raw source), without significant processing or synthetic alteration, wherein "without significant processing or synthetic alteration" is intended as processed only by manual, mechanical or gravitational means e.g. by dissolution in water or other naturally occurring solvents, such as water, water-alcohol solutions etc.; by flotation; by extraction with water or other naturally occurring solvents; by steam distillation or by heating solely to remove water or any other naturally occurring solvent; or extracted from air by any means and with the provision that "natural matrix" excludes said member of the natural kingdom or a naturally occurring portion thereof as such. In other words, a natural matrix or a mixture of natural matrices, are materials obtained from entities that are self-assembled in nature and processed while preserving their native bio-physical characteristics which determine their physiological interaction with other living organisms, such as the human organism. Their emerging properties can be expressed by contributing to the rebalancing of metabolic processes or states of the receiving organism and/or of some organs or tissues alongside the physiological actions that will be activated in each specific context. According to the present invention the natural matrix can be from a material obtained from any source in the life kingdoms i.e. Monera, Protista, Fungi, Plantae and Animalia. The term hence encompasses a plant natural matrix, an animal natural matrix, a fungi natural matrix a protista (archaea or bacteria) natural matrix a monera natural matrix. A natural matrix may also comprise natural inorganic materials such as minerals extracted from natural raw materials. A synonym of natural matrix or one or more natural matrix in the present description is "natural material" as defined below.

An example of naturally occurring portion of an organism may be represented by e.g. roots, leaves, bark, fruit, flower, of a plant or sections thereof, organs, tissues.

In any part of the description the general term natural matrix can be substituted with:

- a plant natural matrix or a natural matrix obtained from a plant,
- an animal natural matrix or a natural matrix obtained from an animal,
- a fungi natural matrix or a natural matrix obtained from a fungus,
- a protista natural matrix or a natural matrix obtained from a protista,
- a monera natural matrix or a natural matrix obtained from a monera,
- or with a plant material and/or extract, an extract from an animal tissue or organ, a fungi and/or a fungi extract, or a mixture thereof. In addition a natural matrix may contain minerals or components obtained from minerals.

Plant is synonymous with herb.

For example, in the context of products comprising or consisting of material of plant origin (obtained from plants) such as herbal supplements a natural matrix would comprise a part of the original, not intentionally altered, preferably unaltered, constituents that are naturally present in the source materials (e.g. extracts of the source material) and therefore contain various organic and inorganic constituents that are found in the aforementioned kingdoms.

The term "natural" matrix emphasizes the retaining the integrity and complexity of a network of constituents/components as in the original natural source, rather than isolating, purifying or extracting specific molecules or molecular classes through extensive processing or chemical modification.

Due to the supramolecular self-assembly of the constituents/components of a natural matrix, the whole matrix behaves as a complex network that does not interact with a single target molecule but that interacts with a network of recipients (also organised as a network) in the receiving organism. Therefore, the interaction natural matrix-receiving organism is not, as for common pharmaceutical APIs the result of a point-to-point interaction, but the result of an "interactor" network (i.e. the matrix)-"receiver" network (i.e. the organism to whom the matrix is administered) interaction.

The term natural matrix can be also substituted in any part of the description and claims with complex natural system.

Nowhere in the description and in the claims the term natural matrix can be interpreted as "a product of nature", rather, a natural matrix is a product obtained from a natural organism and processed (e.g. extracted) therefrom by techniques that do not substantially alter biological structure and the supramolecular interconnections among the components within the matrix.

Emerging properties according to the present description and to the art, the term defines the properties of a natural matrix or of a natural material according to the present specification, i.e. properties that are not represented by the mere sum of properties of each singled out constituent/component of said matrix/material but by the intermolecular interactions among all constituents/components of the matrix/material that are the result of the supramolecular self-assembly of said components/constituents within the matrix/material itself.

"Emerging properties" hence refer to technical effects, such as therapeutic or homeostasis-adjuvating properties (i.e. beneficial effect), that the interactions and relationships among the constituents/components of a natural matrix exert on a receiving living system. Emergent properties are not immediately evident or predictable based solely on the individual characteristics of each constituent/component of the matrix. Instead, they "emerge" as all the constituents/component of the matrix network interact with one another and with the living system receiving network in a dynamic and complex way. Emerging properties have been broadly discussed in the art in various scientific and systems-oriented fields, including physics, chemistry, biology, and complex systems theory.

Key points about emerging properties include:

System Complexity: Emerging properties are associated with systems that exhibit a certain level of complexity. In simple systems, the interactions between constituents/components are limited, and properties are more easily deducible from the properties of individual constituents. In complex systems, however, the interactions between components and their supramolecular organisation can give rise to novel and unexpected features.

Nonlinearity: Emergent properties often result from nonlinear interactions, where the relationship between cause and effect is not proportional.

Holism: The concept of emerging properties emphasizes a holistic perspective, recognizing that the whole system is more than the sum of its parts.

A product comprising or consisting of one or more natural matrix (alias "a product comprising or consisting of complex natural system/s") according to the present invention is a product that comprises or consists of one or more natural matrix, herein also defined as a "natural material" i.e. a "material obtained/manufactured/processed from a natural raw source (raw material) or from a member of the natural kingdom" cfr. below.

In any part of the description and the claims "a product comprising or consisting of one or more natural matrix" can be replaced by "a product comprising or consisting of one or more plant matrix" or by "a product comprising or consisting of complex natural system/s" "a natural material or a material of natural origin".

Furthermore, the term "product comprising or consisting of one or more natural matrix" according to the present description can be an intermediate, or the final formulation for intended use (e.g. resuspended dry product) or, in particular when the formulation for intended use is in liquid form, the term can define a dry or a lyophilised or a concentrated form thereof to which water will be added by the user or by the physician in order to prepare the formulation for administration.

Nowhere in the description and in the claims "a product comprising or consisting of one or more natural matrix" can be intended as a product of nature as such. In addition, when a single natural matrix is present in or consists of said product, said natural matrix is obtained (e.g. extracted) from an organism as defined above by technological means; when a mixture of natural matrices is comprised in or consists of the product, said mixture is a mixture of selected natural matrices made by man, and said mixture cannot be found as such in any of the natural products of origin of each matrix contained therein. Therefore, when the product comprises or consists of a plurality of natural matrices, said natural matrices have been combined by man and the resulting product is endowed of new emergent properties.

According to the present description, the expression "biological functions related to a pathological condition" refers to a set of biological functions associated to a distancing/deviation from homeostasis which may or may not reach the onset, progression, worsening, of a pathological condition. Hence, the expression "biological functions modifications related to a pathological condition" refers to modulations or changes in the normal (healthy) physiological state of biological functions (e.g. activities or processes) within an organism (preferably a human) that are directly associated to an alteration/impairment of homeostasis, up to a pathological state or disease. In other words, it describes the specific adjustments or deviations from the healthy physiological state of a set of biological functions that occur as a result or that concur to the onset, progression, worsening, of a pathological condition or disease. By way of example, in the case of diabetes, biological functions related to glucose metabolism, insulin production and management are modified in ways that are directly associated to the pathological condition of diabetes and are hence related to the pathological condition or state of diabetes according to the present description.

Synthetic according to the present description has the meaning conventionally accepted in chemistry.

Conventionally, in chemistry, the term "synthetic" refers to the origin or source of a material or substance. Synthetic substances or materials are produced by man through artificial synthesis i.e. through laboratory chemical reactions usually by reacting simpler chemicals to create more complex ones through processes that often use different pathways, temperature conditions, pressure conditions, energy sources and/or catalysers from those used by living organisms.

Examples: Synthetic substances or materials include plastics, pharmaceutical drugs, and many industrial chemicals. For example, nylon is a synthetic polymer made through chemical synthesis, and aspirin is a synthetic drug produced through specific chemical reactions.

The term "eubiotics" in the present description has the meaning of "being innate to the living kingdoms" (i.e. plant, animal, fungi, protista, monera kingdoms). The term is derived from the Greek words "eu," meaning good or well, and "bios," meaning life. In the present description, the Greek concept of "eu" is intended with the meaning of "being innate to"/"belonging to" the living kingdoms and as such retaining the integrity and complexity of their interactions. The term is counterposed to "xenobiotic". The term "xenobiotic" is derived from the Greek words "xenos", meaning foreign, and "bios", meaning life. It refers to substances and materials that are "foreign to the living kingdom", in the sense that they are foreign to the natural nutrition/metabolism of living organisms.

In general, eubiotic medicines or treatments or supplements are designed to support and promote a healthy balance within a biological system without introducing substances or materials which constitute a source of dis-equilibrium within said biological system. This could involve medications aimed at positively influencing the microbiome, promoting a healthy immune response, or enhancing overall well-being e.g. by promoting a physiological state. Eubiotic medicines may only be natural, since synthetic products are a source of dis-equilibrium to physiological processes.

In agriculture, eubiotic is normally related to practices that enhance soil health and promote a balanced ecosystem for crops. This may involve the use of organic fertilizers, crop rotation, and other sustainable farming practices.

In microbiology, eubiotic commonly refers to the study of microorganisms that contribute positively to the health of their environment. This includes understanding the role of beneficial bacteria in various ecosystems.

Overall, the general underlying concept in the term eubiotic is the promotion of a state of well-being, balance, and harmony within a biological system, whether it be the digestive system of animals, the human microbiome, or an ecosystem.

An in vitro cell-based assay, in the present description has the meaning conventionally used in the art, in particular, it refers to a cell-based assay for evaluating the cell behaviour and reaction to insults or stimuli, in the context of a disease or of a pathological or pre-pathological condition and is intended as a laboratory technique used to evaluate how a specific disease or pathological or pre-pathological condition affects the behaviour, functions, or characteristics of selected cultured cells. This type of assay is designed to study the biological response of cells in a controlled environment, often in a petri dish or a well plate.

Cell-Based: This term indicates that the assay involves living cells. These cells can be derived from humans, animals, or cell lines that mimic specific tissues or organs.

Assay: An assay is a series of tests or procedures conducted in a laboratory setting to measure or analyse a particular characteristic or function of biological material. In this case, it's focused on cells.

Disease or pathological/pre-pathological condition context: In the context of a disease or pathological/pre-pathological condition, a cell-based assay is specifically designed to simulate or mimic conditions related to the disease or pathological condition. In particular a cell based assay can be used to evaluate in vitro the therapeutic, adjuvating and/or beneficial effect of different compounds or products. It could involve exposing cells to factors known to be associated with the disease or pathological condition, to potential therapeutic or adjuvating products adjuvating the restoration of the physiological state, or using cells that have been genetically modified to carry disease or pathological condition-specific traits.

A healthy physiological state refers to the condition of an organism's body, organ, apparatus, system or body district, and its internal processes when they are functioning optimally and within normal parameters for that individual, i.e. the state to which homeostasis tends. A healthy physiological state, in the context of biological functions known to contribute to hallmarks of a given disease or pathological condition, refers to the condition in which said various biological functions are operating optimally and within normal (healthy) parameters. This state is characterized by the absence of significant aberrant cellular or molecular processes associated with the specific disease under consideration.

The term takes into account the hallmarks of a particular disease, which are distinctive features or characteristics that are typically observed in individuals affected by that disease. These hallmarks can include specific cellular behaviours, molecular pathways, or physiological responses that play a key role in the development or progression of the disease.

In summary, a healthy physiological state in the context of a specific disease or pathological condition is a state in which the biological functions related to the known hallmarks of that disease or pathological condition are modulated in a direction that is consistent with a non-diseased (non-pathological) state, in other words, opposed to the diseased (pathological) state.

A healthy physiological state, therefore, also indicates the direction of the modulation of biological functions that are known hallmarks of a pathological condition in homeostasis, i.e. before the onset of a pathological condition, in other words the homeostatic direction of the modulation of a set of biological functions ascribed to a specific system, district, apparatus or organ of a healthy subject.

Hallmark of a disease or of a pathological or medical condition according to the present description has the meaning conventionally used in the art. According to the state of the art, hallmarks of a disease are indicators that can mark the progression or control of a given disease or pathological condition. These hallmarks (also called 'key indicators') are typically a set of features or patterns that a physician would monitor, over time, to track the progression or regression of a particular illness. In summary, a hallmark of a disease is a defining feature or characteristic whose modification is indicative of a given medical condition, aiding in its identification, diagnosis, monitoring and understanding. By way of example, for neurodegenerative diseases (NDDs) at least the following eight hallmarks of NDD are known in the art: (pathological protein) aggregation, synaptic and neuronal network (dysfunction), (aberrant) proteostasis, cytoskeleton (abnormalities), (altered) energy homeostasis, DNA and RNA (defects), inflammation (increase), and neuronal cell death (increase). In cancer research, the hallmarks of cancer are a set of distinctive characteristics that are commonly found in cancer cells. These hallmarks include (sustained) proliferative signalling, (evasion of) growth suppressors, (resistance to) cell death, (enabling) replicative immortality, (inducing) angiogenesis, and (activating) invasion and metastasis.

Hallmarks of a disease, their biomarkers, biological functions associated to said hallmarks etc. are a framework to study a disease or a pathological or medical condition using an integrated/holistic approach.

The expression "natural material," according to the present description, refers to materials consisting of one or more natural matrix with the provision that said material/s are not found in nature as such but are the result of a technical human intervention (such as, e.g. extraction processes, filtration, and the like, i.e. elaborates). These materials are typically obtained from plants, animals, fungi or microorganisms, and minerals through preparation processes that aim to preserve the integrity of the networks within the natural raw sources from which the natural material is prepared. In the present description "natural material" is considered as a synonym of one or more natural matrix. A natural material according to the present description can therefore be a product, such as a product with a therapeutic effect, consisting only of or comprising different natural matrices selectively assembled (that are not combined in such combination in nature) in order to produce a given therapeutic effect thereby forming an "interactor network" whose administration to a subject (i.e. a receiving living network) shows emerging properties providing a therapeutic effect or a homeostasis adjuvating effect, i.e. an effect beneficial to the health of said subject.

"Having Therapeutic effect": according to the present description a product having a therapeutic effect is a product which, upon administration to a subject affected by a pathological condition, reduces the severity of the subject's condition (i.e. the severity is at least partially reduced or mitigated), and/or provides some alleviation, mitigation or decrease in at least one clinical symptom and/or in a delay in the progression of said condition or reinstates (completely or in part) a healthy physiological condition in the district affected by said pathological condition.

Having beneficial effect according to the present description encompasses a product whose administration to a healthy subject or a subject which is healthy but not in homeostasis, or to an in vitro cell assay representing an adequately healthy status, results in an in vitro or in vivo evidence of a reinstatement or adjuvation of homeostasis upon administration in said cell assay or in the recipient's system/district/apparatus/organ of interest.

The terms "prevent," "preventing," and "prevention of" (and grammatical variations thereof) refer to reduction and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of a composition according to the present invention.

Having a "beneficial/healthy/beneficial to health" effect according to the present description encompasses a product whose administration to a healthy subject or to a healthy subject who is not in homeostasis or to an in vitro cell assay representing an adequately healthy status, results in an in vitro or in vivo evidence of a reinstatement or adjuvation of homeostasis upon administration in said cell assay or in the recipient's system/district/apparatus/organ of interest.

The term "product having (ascertained) therapeutic properties comprising one or more natural matrix" or "product for the treatment of a pathological condition, said product comprising one or more natural matrix" according to the present invention is a product as defined above wherein the emerging properties of said product provide a therapeutic effect as defined below in this glossary.

The term can be replaced in any part of the description and of the claims by "product having therapeutic activities comprising or consisting of complex natural systems" "formulation having therapeutic properties comprising (or consisting of) complex natural systems" or with "composition having therapeutic properties comprising (or consisting of) complex natural systems" or with "mixture having therapeutic properties comprising (or consisting of) complex natural systems" wherein the term "complex natural systems" can be substituted with "one or more natural matrix" or with "natural material".

The definition applies, mutatis mutandis, to the term "product having beneficial/healthy/beneficial to health properties comprising one or more natural matrix".

According to the present description the term homeostasis has the meaning conventionally accepted in the art, and refers therefore, to the physiological process by which living organisms maintain a stable internal environment despite external changes. This stability is crucial for the proper functioning of cells, tissues, and organs. The goal of homeostasis is to ensure that the internal conditions of an organism remain within optimal ranges for survival and proper physiological functioning (healthy physiological state). Homeostasis is obtained by organisms by the modulation of a set of biological functions and processes aimed to maintain a healthy physiological state.

A product adjuvating homeostatic processes is a product that modulates biological functions in the direction of a healthy physiological state, hence, a product that is suitable for a healthy individual and that supports the homeostatic mechanisms that contribute to the healthy physiological state and that can be used by a healthy individual in order to adjuvate the homeostatic regulations of biological functions associated to hallmarks of a given pathological condition.

Medical device, also MD, according to the present description is a product as defined above, according to the definition in EU Regulation 2017/745 Article 2 (1) indents 1-3, necessarily used for therapeutic purposes hence, 'medical device' means any . . . [omissis] . . . material intended by the manufacturer to be used, alone or in combination, for human beings for one or more of the following specific medical purposes:

treatment or alleviation of disease, treatment, alleviation of, or compensation for, an injury or disability, modification of a physiological or pathological process or state, . . . omissis . . .

and which does not achieve its principal intended action by pharmacological, immunological or metabolic means, in or on the human body, but which may be assisted in its function by such means.

'performance' of a medical device means the ability of a medical device as herein defined to achieve its intended purpose as stated by the manufacturer;

'clinical performance' of a medical device means the ability of a medical device as herein defined, resulting from any direct or indirect medical effects which stem from its technical or functional characteristics, including diagnostic characteristics, to achieve its intended purpose as claimed by the manufacturer, thereby leading to a clinical benefit for patients, when used as intended by the manufacturer;

'clinical benefit' of the medical device means the positive impact of a device as herein defined on the health of an individual, expressed in terms of a meaningful, measurable, patient-relevant clinical outcome(s), including outcome(s) related to diagnosis, or a positive impact on patient management or public health.

Also, if a composition, (e.g. a contrivance, such as product having therapeutic properties comprising one or more natural matrix), is intended to have a medical purpose, such as diagnosis, treatment, mitigation, or prevention of a disease or to affect the structure or function of the body, and it meets the criteria outlined in the definition, it may be classified as a medical device by the US FDA.

Per Section 201(h)(1) of the Food, Drug, and Cosmetic Act, a device is:

An instrument, apparatus, implement, machine, contrivance, implant, in vitro reagent, or other similar or related article, including a component part, or accessory which is:

(A) recognized in the official National Formulary, or the United States Pharmacopoeia, or any supplement to them, (B) intended for use in the diagnosis of disease or other conditions, or in the cure, mitigation, treatment, or prevention of disease, in man or other animals, or (C) intended to affect the structure or any function of the body of man or other animals, and which does not achieve its primary intended purposes through chemical action within or on the body of man or other animals and which is not dependent upon being metabolized for the achievement of its primary intended purposes. The term "device" does not include software functions excluded pursuant to section 520(o).

The classification of medical devices within a risk class is typically based on factors such as intended use, indications for use, and risk associated with the device.

A product considered as having an ascertained therapeutic effect according to the present invention means that it is a product for which a gold standard of the product that shows the desired therapeutic effect at least in vitro, e.g. in laboratory settings using cells, organoids, tissues and/or in vivo on animal models or clinical trials exists.

The expression having an ascertained beneficial/healthy/beneficial effect according to the present invention means that it is a product for which a gold standard of the product that shows the desired effect of reinstatement/adjuvation of homeostasis in the at least in vitro, e.g. in laboratory settings using cells, organoids, tissues and/or in vivo on animal models exists.

A subject "in need thereof" as used herein refers to a subject that can benefit from the therapeutic and/or prophylactic effects of the therapeutical compositions. Such a subject can be diagnosed with a disease or disorder, a subject suspected of having or developing a disorder or, and/or a subject determined to be at increased risk of having or developing a disease or disorder.

By the terms "treat," "treating," or "treatment of" (and grammatical variations thereof) it is meant that the severity of the subject's condition is reduced, at least partially improved or ameliorated, and/or that some alleviation, mitigation or decrease in at least one clinical symptom is achieved and/or there is a delay in the progression of the disease or disorder.

BRIEF DESCRIPTION OF THE DRAWINGS

Legend of the Batches

FIGS. 2-7 and 12:

Figure 5:
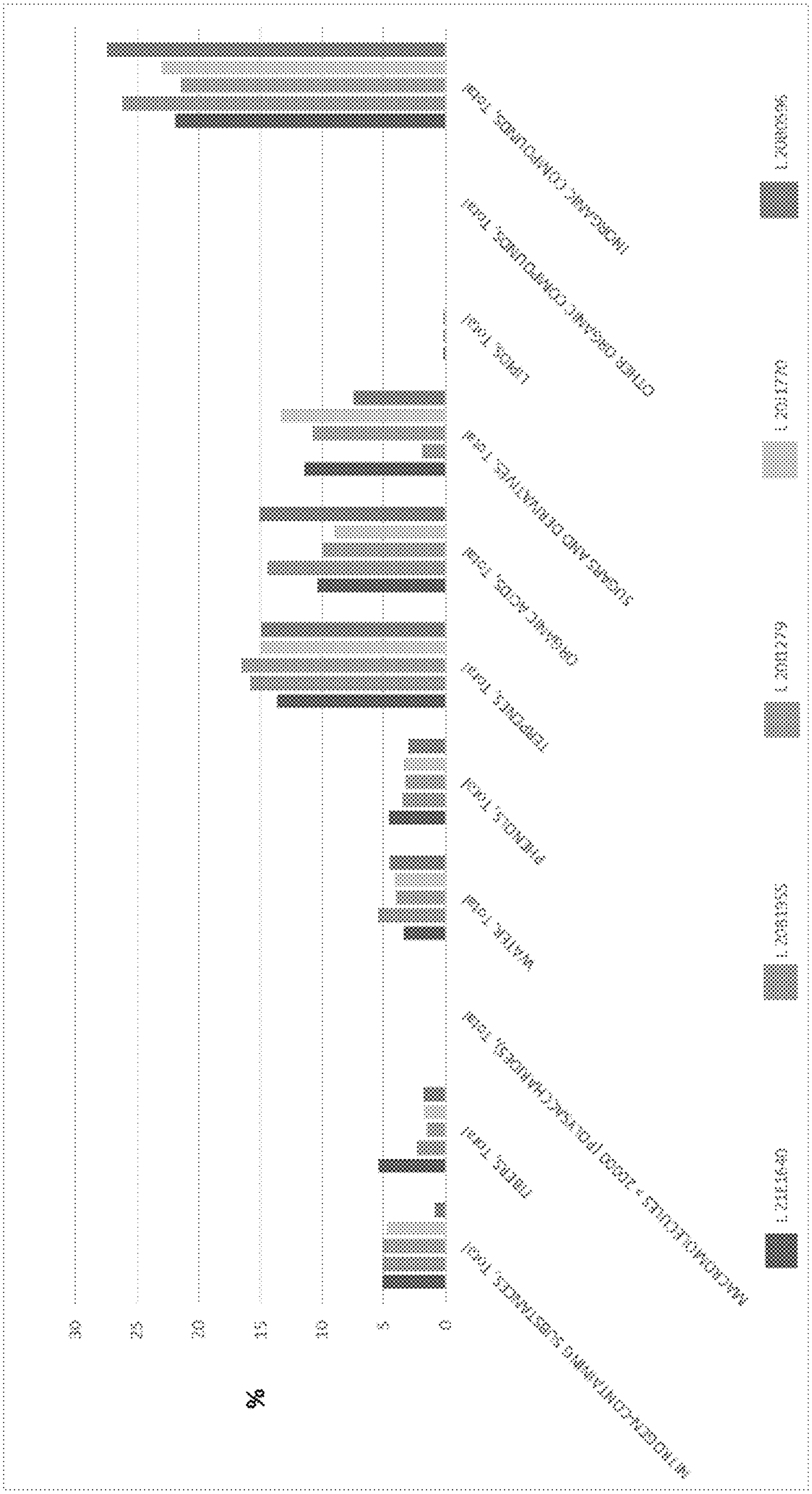

Product Arté-Gx in lyophilised form (see detailed composition of the product in Example 1

Batch 20B1955 also L 20B1955 Gold Standard

Batch 20B0596 also L 20B0596

Batch 20I1297 also L 20I1297

Batch 21E1640 also L 21E1640

Batch 20J1770 also L 20J1770

Batch Dest 21E1640

FIG. 9 Product B Gold standard

FIG. 11 Product C Gold standard (see detailed composition of the products in Example 1).

FIG. 1 Exemplification of hallmarks of osteoarthritis including the trend of the hallmark representing an improvement of the diseased state, (column 1), biological functions concurring to each disease (column 2) and modulations thereof in the pathological conditions (column 3) and modulation of each of said biological function representative of a healthy physiological state (column 4) dark grey: up modulation light grey: down modulation.

FIG. 2 Modulation of selected biological functions in a chondrocytes cell-based assay in osteoarthritis: column 1 hallmarks including the trend of the hallmark representing an improvement of the diseased state, column 2 biological functions, column 3 predicted modulation of biological functions in pathological state, column 4 desired modulation of biological functions in healthy physiological state, column 5 cell-based assay without therapeutic treatment, representative of the biological functions modulation of the pathological state, column 6 modulation induced by the gold standard of the tested product. The cell-based assay shows that the gold standard modulates the selected functions according to the healthy physiological state. The numbers reported in each square represent a Z-score calculated with the method of the invention representing the modulation of each biological function observed.

FIG. 3 Modulation of selected biological functions in a chondrocytes cell-based assay representative of osteoarthritis: column 1 hallmarks including the trend of the hallmark representing an improvement of the diseased state, column 2 biological functions, column 3 predicted modulation of biological functions in pathological state, column 4 desired modulation of biological functions in healthy physiological state, column 5 cell-based assay without therapeutic treatment, representative of the biological functions modulation of the pathological state, column 6 modulation induced by a reference drug (Triamcinolone Acetonide), column 7 modulation induced by the gold standard of the tested product, columns 8-11 modulation induced by four different batches of the tested product. In particular, column 11 represents the modulation induced by an intentionally destabilised batch (DEST 21E1640) showing weaker therapeutic activity. The cell-based assay shows that the gold standard and the additional batches similarly modulate the selected functions according to the healthy physiological state. The numbers reported in each square represent the Z-score value calculated representing the modulation of each biological function observed.

FIG. 4 Corresponds to FIG. 3 plus column 12 showing the control analysis of the modulation induced by the non destabilised batch (21E1640) that was validated as compliant according to the process of the invention. The cell-based assay shows that the gold standard and the additional batches similarly modulate the selected functions according to the healthy physiological state and therefore confirms the compliance of the batch that was validated with the method of the invention. The numbers reported in each square represent the Z-score value calculated representing the modulation of each biological function observed. The reference Z score values were calculated according to the invention taking into account the Gold Standard Z-score values (column 8 of FIG. 4) and the drug Z-score values (column 9 of FIG. 4) selecting as reference Z-score value (column 13 of FIG. 4) for each modulated biological function the Z-score value associated to the weakest performance as depicted in the table below:

| Hallmarks of the pathology | Biological functions | Reference drug Triamcinolone acetonide Drug Z-score values | Gold standard Z-score values | Reference Z-score values |
|---|---|---|---|---|
| Induction of proliferation | Skeletal and muscular system development and function → articular dysfunction → joint space → Formation of cartilage tissue | −0.31 | 0.15 | 0.15 |
| Reduction of inflammation | Inflammatory disease → inflammation and nociceptions → Inflammation of joint | −0.26 | −0.24 | −0.24 |
| Protection from anatomical damage | Skeletal and muscular system function → difficulty moving a joint → Non-traumatic arthropathy | −0.17 | −0.32 | −0.17 |
| | Organismal injury and abnormalities → joint inflammation and swelling, difficulty moving a joint → Osteoarthritis | −0.15 | −0.31 | −0.15 |

As the therapeutic effect is ascertained both for the product as well as for the drug, it is correct to accept, when both the reference drug and the gold standard provide modulation of a selected biological function in the same direction of the healthy physiological state, the weakest performance z-score as reference cut-off for that modulation.

FIG. 5 Targeted metabolomics of five batches (including gold standard) of Arté Gx main chemical classes. The figure clearly shows that each batch tested differs from each other and from the gold standard in the quali-quantitative composition. Comparison with tests of the selected biological activities of the same batches on the cell based-assay (FIGS. 3 and 4), shows that the quali-quantitative analysis of different batches of a product for use in the treatment of a pathological condition, the product comprising or consisting of one or more natural matrix does not allow to correctly estimate it's activity profile.

Figure 6A:
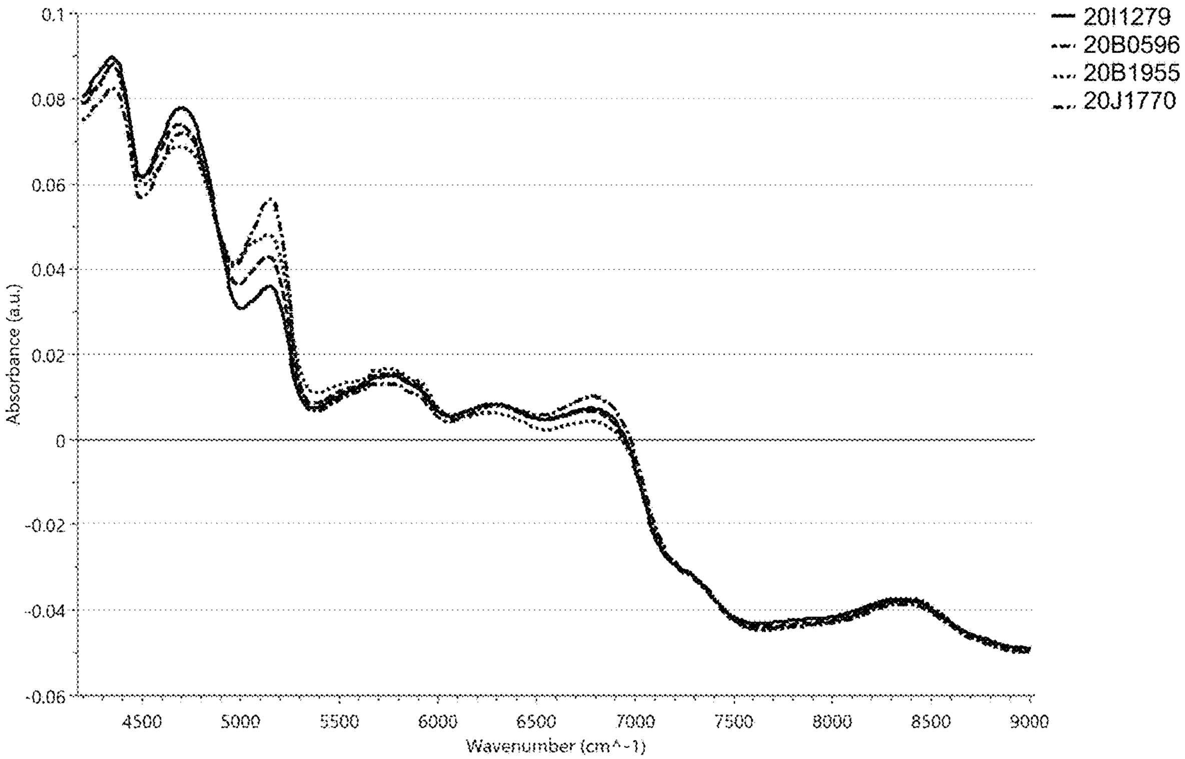
Figure 6B:
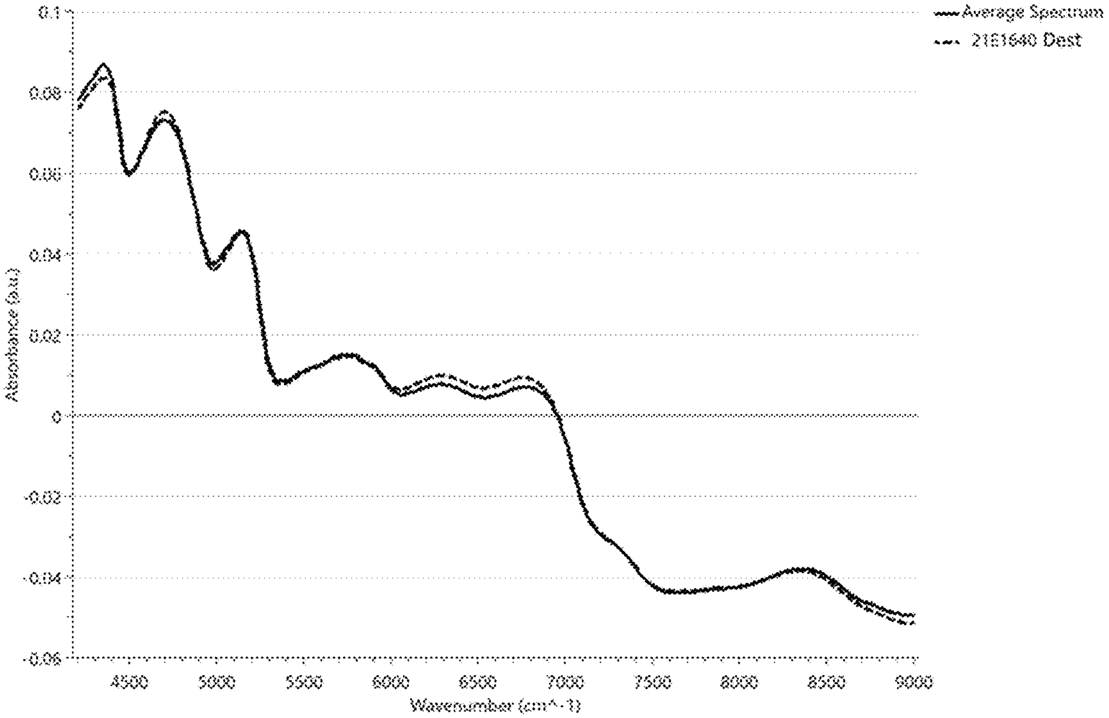
Figure 6C:
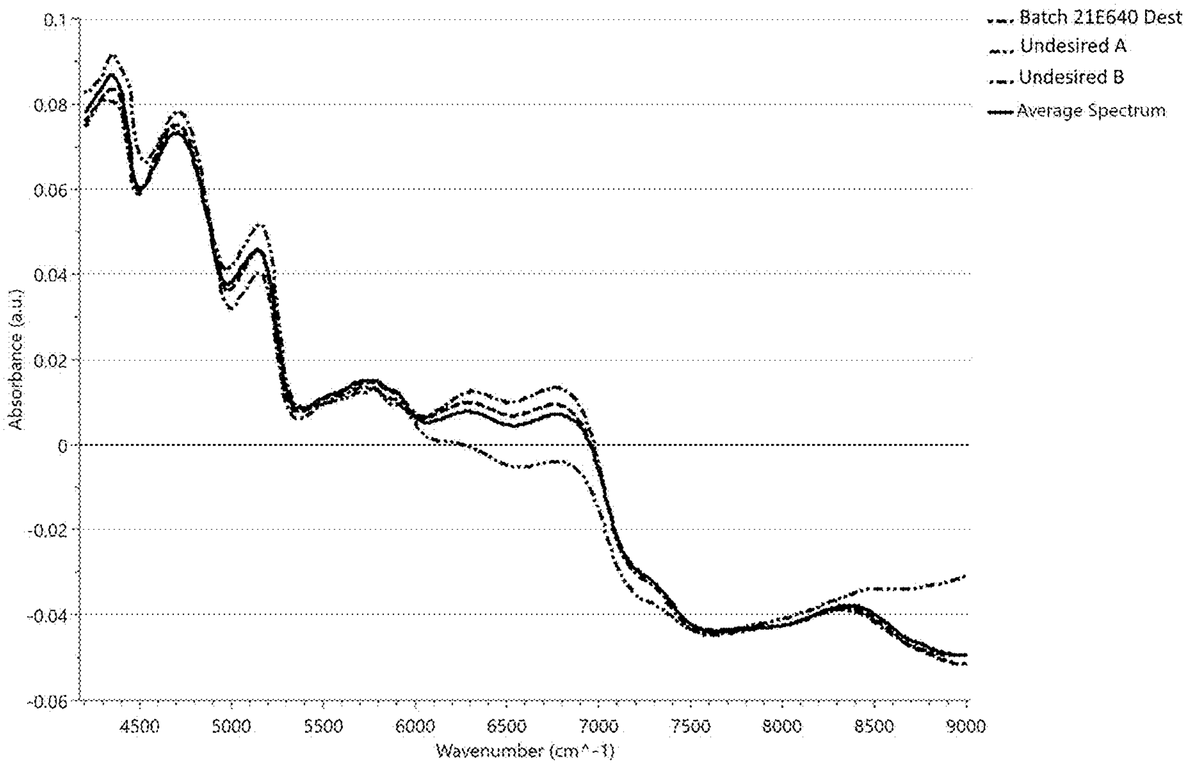
Figure 6D:
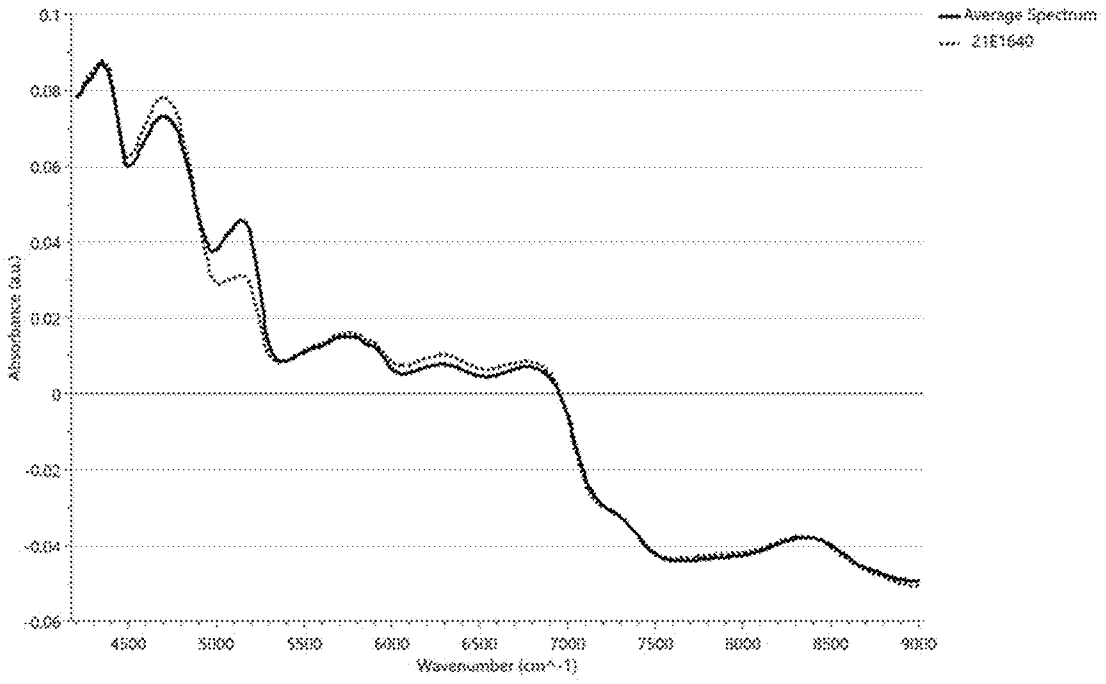

FIG. 6*a*. NIR spectrum of the gold standard and three different positive batches selected in iv) in the wavelength range of interest. FIG. 6*b*. NIR average spectrum of the four batches of FIG. 6*a*, and NIR spectrum of negative batch 21E1640 Dest, FIG. 6*c*. NIR average spectrum of the four batches of FIG. 6*a* and two a priori undesired spectra (undesired A *Centella asiatica* extract, undesired B *Echinacea* extract) FIG. 6*d*. NIR average spectrum of the four batches of FIG. 6*a*, and NIR spectrum of unassessed batch 21E1640 (not destabilised).

Figure 7:
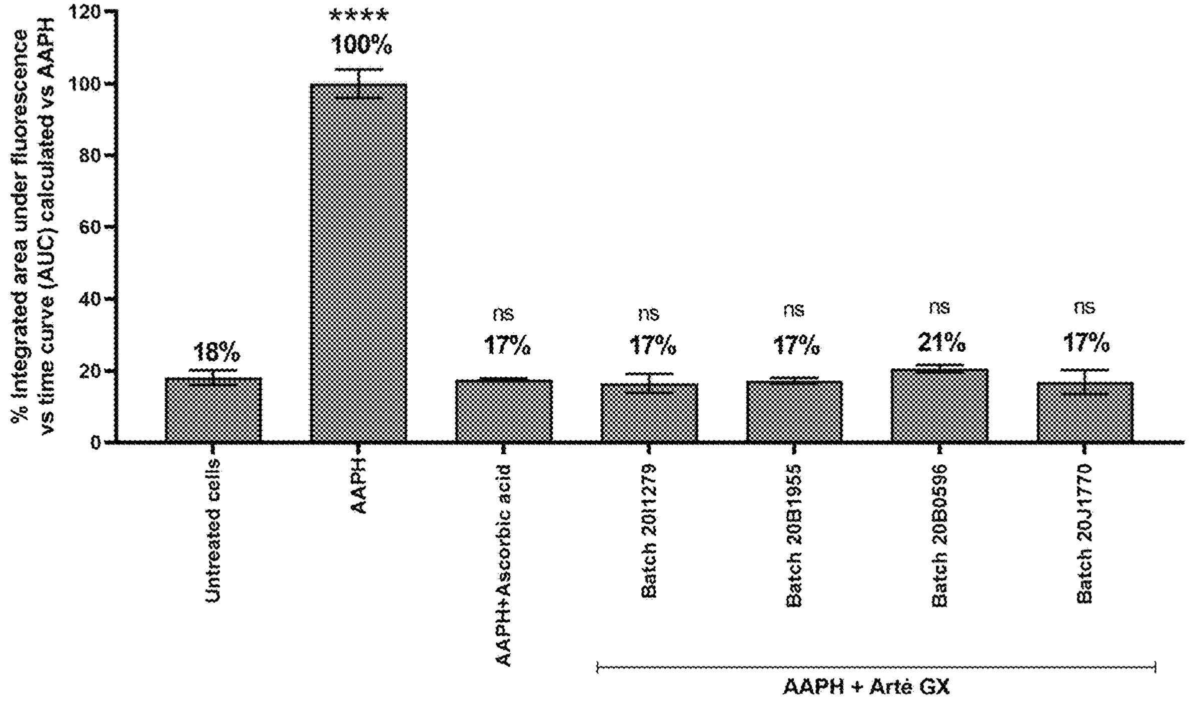

FIG. 7 ROS scavenging activity of 4 validated batches including gold standard of Arté-Gx. The quantity of ROS detected in samples treated with AAPH was considered as the maximum release of ROS (100%) and the quantity of ROS detected in the other samples was calculated as percentage with respect to the maximum release induced by AAPH. One-way ANOVA and Dunnett's post-test were applied. Only values capable of returning $p<0.05$ were considered significant (*$p<0.05$, $p<0.01$, *$p<0.001$, ****$p<0.0001$). Statistical significance of all samples vs untreated cells. The figure demonstrates that the validated batches are, indeed, inducing ROS scavenging activity as desired for the intended therapeutic use.

FIGS. 8*a* and 8*b* Exemplification of hallmarks of mild cognitive impairment (MCI), (column 1), biological functions concurring to each disease (column 2) and modulations thereof in the pathological conditions (expressed as alteration of healthy physiological state) (column 3) and modulation of each of said biological function representative of a healthy physiological state (column 4) dark grey: up modulation light grey: down modulation.

FIGS. 9*a* and 9*b* Modulation of selected biological functions in a human neuronal cell-based assay (cells SH-SY5Y): column 1 hallmarks, column 2 biological functions, column 3 predicted modulation of biological functions in pathological state, column 4 desired modulation of biological functions in healthy physiological state, column 5 modulation induced by the gold standard of the tested product B. The cell-based assay shows that the gold standard modulates the selected functions according to the healthy physiological state. The numbers reported in each square represent a Z-score calculated with the method of the invention representing the modulation of each biological function observed.

In FIGS. 9*a* and 9*b* the tested product B used is described in example 1.

FIGS. 10*a* and 10*b* Exemplification of hallmarks of osteoporosis (OP) including the trend of the hallmark representing an improvement of the diseased state, (column 1), biological functions concurring to each disease (column 2) and modulations thereof in the pathological conditions (expressed as alteration of healthy physiological state) (column 3) and modulation of each of said biological function representative of a healthy physiological state (column 4) dark grey: up modulation light grey: down modulation.

FIGS. 11*a* and 11*b* Modulation of selected biological functions in adipocyte-derived, mesenchymal stem cell lines (hADMSC), capable of differentiating into osteoblasts and mineralize the extracellular matrix (ECM): column 1 hallmarks, column 2 biological functions, column 3 predicted modulation of biological functions in pathological state, column 4 desired modulation of biological functions in healthy physiological state, column 5 modulation induced by the gold standard of the tested product C. The cell-based assay shows that the gold standard modulates the selected functions according to the healthy physiological state. The numbers reported in each square represent a Z-score calculated with the method of the invention representing the modulation of each biological function observed.

In FIGS. 11*a* and 11*b* the Tested Product C Used is Described in Example 1

FIG. 12 modulation of the biological function oxidative stress (hallmark inflammation) of 4 validated batches including gold standard of Arté-Gx. Ascorbic acid has been used as positive control and insult with AAPH as negative control representative of pathological state. As clear from the figure, also the use of a different marker for monitoring the modulation of the biological function causally related to the pathological hallmark of osteoarthritis (OA) is suitable for validating the batches as an alternative to transcriptomics markers.

Figure 13:
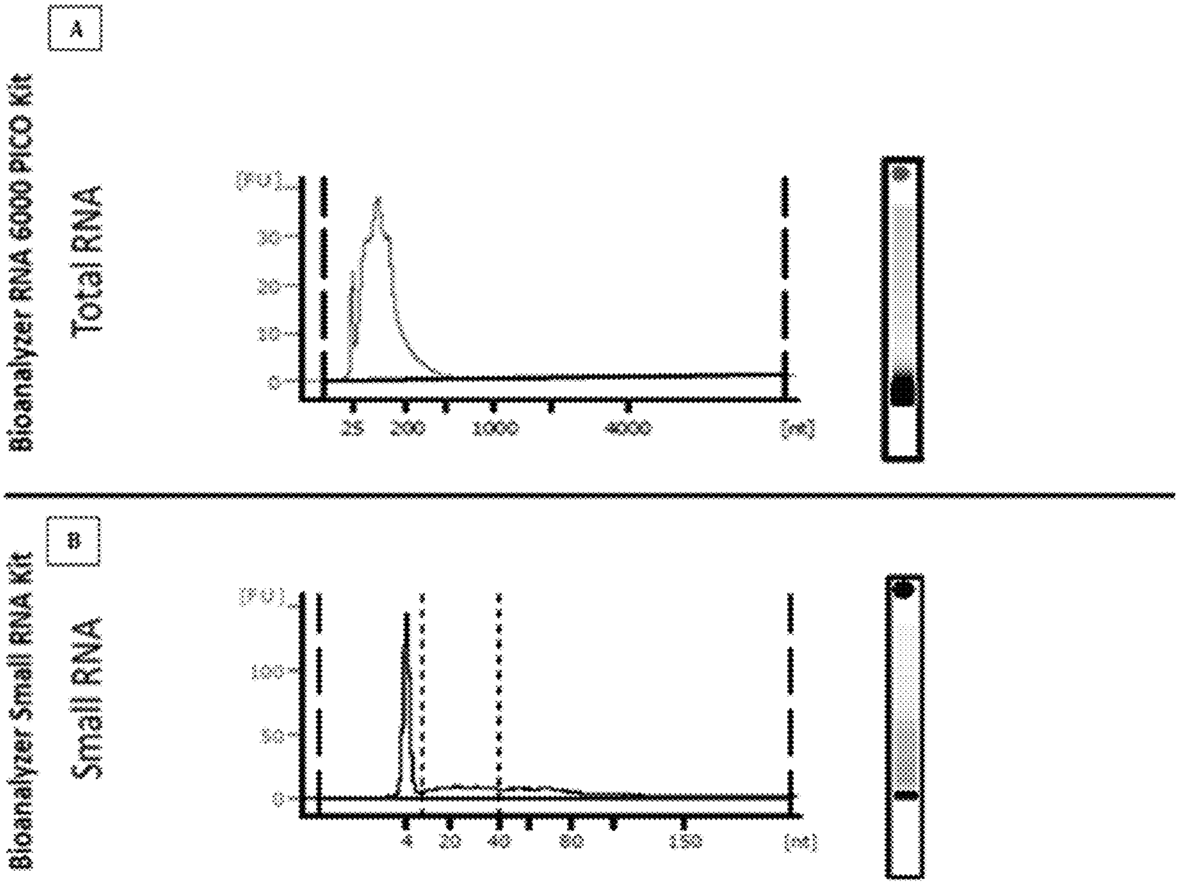

FIG. 13 Biophysical characterization of biological vegetal material total RNA.

FIG. 13 shows the electropherogram of the production intermediate of Arté GX, i.e. the *Centella asiatica* and *Echinacea* water coextract in the proportions depicted in example 1, before ultrafiltration, panel "A" shows the size distribution of the total RNA and panel "B" shows the RNA size distribution between 4 and 150 nt.

DETAILED DESCRIPTION OF THE INVENTION

The present invention provides methods and processes for the batch to batch validation of products comprising or consisting of natural matrices, such as products consisting of 100% eubiotic entities and exerting therapeutic or beneficial activity by allowing the homeostatic rebalancing of physiopathological states or slight imbalances in living beings such as the human organism, through the provision of spectroscopy or spectrophotometry acceptability ranges or cut-offs based on measurements of the modification of specific biological activities concurring to the therapeutic or beneficial effect. The Applicant herein hence provides a new state of the art which will allow to standardise said kind of products and therefore allow to comply with the regulatory frameworks for granting a viable space for innovative uses of said products in therapy. In the past decades the Applicant did pursue an intersectoral research path which, along with scientific innovations, resulted in the development of eubiotic protocols for agricultural production and transformation processes of raw sources (starting materials) so as to preserve their basic natural programmatic rules, which have allowed interconnection for millions of years among all the components of living things, organic and inorganic.

Following the teachings of the present invention it is now possible to assess precise parameters to validate the batch-to-batch compliance of products with emerging properties resulting in a physiological therapeutic activity or beneficial activity, when the product comprises or consists of one or more natural matrices.

This is of particular interest for all the products for therapeutic/beneficial use that are not based on classical pharmacological formulation APIs plus excipients such as products that comprise or consists of one or more natural matrix. The main problem with this kind of products is that, notwithstanding the important therapeutic/beneficial effects exerted, in the absence of repeatable and precise methods for a batch to batch validation, ensuring the compliance of the product with the claimed therapeutic/beneficial effect, which, due to their very origin (nature) present an intrinsic variability in their quali-quantitative composition, cannot be correctly assessed by classical validation processes based on a mere quali-quantitative composition. Up to now, in fact, it has not been possible to bring products comprising or consisting of one or more natural matrix in a regulatory framework that would take this into account and allow for a high degree of innovation. This problem is solved by the present invention.

As the method and process of the invention are designed for products comprising or consisting of natural matrices, it is preferred that the production of these products is carried out standardising the entire production process both in the agricultural and manufacturing processes.

The inventors herein demonstrate that an approach based exclusively on reproducibility assays with classical targeted metabolomics, such as the quali-quantitative analysis of the chemical classes or of specific chemical compounds of a product with therapeutical effects, judged based on criteria designed for management of single APIs acting via the deterministic key-lock mechanism thanks to the existence of a clear SAR, when the product comprises or consists of one or more natural matrix is not suitable for a quality control. In fact, the results obtained by the inventors from the analysis of the chemical classes of different batches of the same product, when confronted with selected biological activities of each batch, show that the quantitative fluctuations of the individual chemical classes of substances that are present in said different batches, if taken as the sole reference parameter for assessing the quality of said batches according to criteria applied to APIs would lead to an a priori assumption that these batches have a different biological activity (see example 3.1 second table and FIG. 5). The experiments carried out by the inventors (cfr. example 3.1 and, in particular, FIGS. 3, 4 and 5) on the contrary, demonstrate that, notwithstanding their variable quali-quantitative chemical composition, said batches nevertheless possess the same biological activity, a resilient behaviour possibly due to the presence of redundancy among the single components at both structural and functional level.

Thus, the experiments carried out by the inventors (in particular, cfr. FIGS. 3, 4 and 5) show that, when considered alone, the quali-quantitative analysis of different batches of a product for use in the treatment of a pathological condition, does not allow to correctly estimate the activity profile when the product comprises or consists of one or more natural matrix. Hence, the data provided herein demonstrate that, contrary to APIs based pharmaceutical products, the quali-quantitative analysis of the individual constituents of a therapeutical product comprising or consisting of one or more natural matrix (i.e. providing a therapeutic effect based on a network to network interaction), therefore especially when performed as a method for assessing the reproducibility of a non-SAR-based entity, is not suitable to evaluate the correct compliance batch to batch of said product.

In fact, given the very nature of a natural matrices, the batch to batch quantitatively variable chemical profiles, would prompt the validator to consider various batches of a product that comprises or consists of one or more natural matrix as a “different material” with respect to a given gold standard of said product, and therefore to discard said batches, while, on the contrary, the results provided by the inventors herein, demonstrate that in biological systems, quali-quantitatively different batches of a given product exert the same relevant reactions for their intended therapeutical use. This is another demonstration that biological activity of a complex matrix cannot be traced back to the sum of the activities of each single molecule within the matrix itself and that reproducibility of the activity of the matrix does not exclusively depend on reproducibility of the identity and quantity of the molecular components which constitute it.

The results obtained by the inventors demonstrate that there are both structural and functional redundancy mechanisms within natural matrices that confer to said matrices a particular resilience, and that that matrix per se should not be perceived as a compilation of molecules acting independently from one another as if they were still subject to the SAR there are commonly attributed when studied in isolation.

As shown in the present description (see examples and figures), different batches of a tested product that comprises or consists of one or more natural matrix, with ascertained differences in their quali-quantitative composition one from the other and from a gold standard of said product, can retain the ability to mediate the same therapeutic or beneficial activity notwithstanding their different quantitative compositions at molecular level.

The authors of the invention therefore, developed a new method for defining the acceptability ranges or cut-offs of a spectroscopy or spectrophotometry analysis that are suitable for the validation of one or more batches of a product for use in the in the treatment of a pathological condition, the product comprising or consisting of one or more natural matrix; and a process for the validation of different batches a product comprising or consisting of one or more natural matrix, that is based on the conservation of selected intrinsic characteristics (modulation of selected biological features) of the matrix rather than on conservation of its molecular components. The method of the invention allows to identify validation acceptability ranges or cut-offs based on the assessment of selected parameters to which the maintenance of a desired overall biological activity is, as demonstrated in the present description, effectively correlated.

The present description discloses in the examples experimental data on a model product herein indicated as Arté-GX (see examples for the composition of the product), which is for use in the treatment of osteoarthritis (disclosed in WO 2018/138678) and substantially consists of plant derived natural matrices. Faced to the problem of satisfying the regulatory requirements for bringing the aforementioned product into therapy, the inventors tested the classical validation methods and realised that the classical validation methods (quali-quantitative chemical composition) were not suitable for correctly assessing the therapeutic effect of the product (compare FIGS. 3, 4 and 5). The inventors therefore developed the method and process herein disclosed and found results consistent with the ones reported herein also on other different products, with therapeutical effects, comprising or consisting of one or more natural matrix.

All the tested products were consisting or comprising of natural matrices and for use in the treatment of a pathological condition, said matrices being obtained from plant biological material suitably processed and formulated so to obtain a final natural material (as defined in the glossary) which is able to modify, upon administration, a pathological state and to promote the restoration of healthy physiological conditions. For all the tested products, a gold standard with an ascertained therapeutic effect was available. A detailed description of the tested products is provided in the examples section.

In the tested products, the hundreds of components coming from the coarse raw plant parts have not been deprived of the ability, characteristic of materials of natural, biological origin, to establish multiple combinations of molecular and supramolecular interactions among themselves and with the target tissues and therefore maintain therapeutic emerging properties.

In particular, the products tested by the Applicant have been prepared, starting from the preparation of the soil to the production of the final product, following eubiotic protocols that have been selected and standardised by Applicant throughout more than 40 years of experience to render, a priori, the final products as homogeneous as possible and therefore increase the efficiency in terms of yield of valid batches. The eubiotic protocol developed by the applicant, has been construed in order to standardise as much as possible each step leading to the desired final product respecting the eubiotics of each step, so to provide a final product which is 100% natural as opposed to a synthetic or partially synthetic product (i.e. a product that does not comprise a single component obtained by artificial chemical synthesis) wherein each component is produced under eubiotic conditions. It is possible to develop a fully eubiotic, standardised, production process with the integration of inter-sectoral technologies and research in several different fields, from the agricultural one to -omics and mathematical sciences ones by comparing, or rather integrating, the reductionist approach discussed above with that of systems theory and quantum biology. Preferably, according to the invention, the tested products comprising or consisting of one or more natural matrix do not comprise molecules of chemical synthesis nor comprises natural matrices that have been put in contact and that may have internalised molecules of chemical synthesis, thereby allowing to provide natural matrices and final products consisting of 100% natural ingredients.

An object of the invention is a method for defining the acceptability ranges or cut-offs of a spectroscopy or spectrophotometry analysis for the validation of one or more batches of a product for use in the treatment of a pathological condition, comprising or consisting of one or more natural matrix, comprising calculating said acceptability ranges or cut-offs on a spectroscopy or spectrophotometry spectra of a gold standard having an ascertained therapeutic effect in the treatment of said pathological condition and one or more batches of said product said spectra being defined as acceptable or non-acceptable on the basis of the biological activity exerted in at least one cell-based assay by said gold standard and of one or more batches on one or more hallmarks of said pathological condition.

Depending on the pathological condition of interest, the hallmarks can be one or more, preferably more hallmarks are selected, however, e.g. in the case of cancers, the skilled person is well aware that the more relevant hallmark is the proliferation of the cancer cells, therefore the elected cell based assay will be in this case, an assay verifying the viability of neoplastic cells or of tumour masses upon administration of the product of interest. Still, according to the invention it is preferred to use a single cell based assay is used, however, more than one cell based assays can also be used, in a non-limiting example, when for the analysis of different hallmarks different cell based assays are deemed more suitable, additional cell based assays can be carried out.

The main difference between the product validation procedures of the present invention and the state of the art, is based on the demonstration that, although informative, the quali-quantitative characterisation of a product comprising or consisting of one or more natural matrices, due to the dynamic interactions of all its constituents that result in new emerging properties, is not suitable for assessing the real effectiveness of these kind of products and therefore the validation procedures have to be carried out on basis that differ from the ones of classical API based therapeutical products. Indeed, a quali-quantitative validation, in case of products comprising or consisting of natural matrices, as shown also by the data provided in the examples and in the figures, is not sufficient nor suitable to ensure the therapeutic effectiveness of the product.

As a result, the applicant has developed new methods and processes that base the validation procedures on the definition of validation parameters that are truly representative of the therapeutic effectiveness of the product.

Additional metabolomics analysis may nevertheless still be desirable for the manufacturers e.g. in order to evaluate the toxicological profile of the product.

Depending on the pathological condition of interest, the hallmarks can be one or more, when available, preferably more hallmarks are selected, however, e.g. in the case of cancers, the skilled person is well aware that the most relevant hallmark is the proliferation of the cancer cells, therefore the skilled person can limit the method of the invention to this single hallmark and the elected cell based assay will be in this case, assays verifying the viability of neoplastic cells or of tumour masses upon administration of the product of interest.

According to an embodiment of the invention, the method comprises the following steps:

i)

a. retrieving from the state of the art a list of the hallmarks of said pathological condition;

b. identifying for each of said hallmarks a set of biological functions modifications detectable in said pathological condition and determining the modulation of each of said functions concurring to the desired therapeutic effect thereby designing the modulation pattern of each of said functions representing a healthy physiological state;

c. identifying the markers and the modulation pattern thereof underlying the modification detectable in said pathological condition for each of said biological functions and setting for each of said markers the modulation pattern opposite to the one identified as the modulation pattern indicative of said healthy physiological state;

ii) analysing the expression pattern of each of the markers identified in i) c. induced by a gold standard of said product in a suitable in vitro cell-based assay, determining the quali-quantitative modulation of each of said markers induced by said gold standard with respect to the pathophysiological state control of said in vitro cell based assay, and calculating the gold standard Z-score value of the modulation of each of said biological functions induced by said gold standard and selecting each of said gold standard Z-score values as reference cut-off Z-score values indicative of said desired therapeutic effect, iii) analysing the modulation pattern of the markers identified in i) c. induced by further different batches of said product in said in vitro cell-based assay and determining the quali-quantitative modulation of each of said markers induced by each of said batches thereby calculating the Z-score value of the modulation of each of said biological functions induced by each of said batches iv) comparing the Z-score value of the modulation of each of said biological functions induced by each of said batches calculated in iii) with the corresponding cut-off Z-score values of the modulation of each of said biological functions provided in ii) and selecting at least three positive batches for which each Z-score value of the modulation of each of said biological functions calculated in iii) complies with the corresponding reference cut-off Z-score values and at least one negative batch for which at least one Z-score value of the modulation of each of said biological functions calculated in iii) does not comply with the corresponding reference cut-off Z-score value v) carrying out a spectroscopy or spectrophotometry analysis of said gold standard and of the batches selected in iv)

vi) defining as acceptable the variability spectroscopy or spectrophotometry ranges resulting by the considering each the results obtained in v) as acceptable for each positive batch and non-acceptable for each negative batch thereby providing said acceptability spectroscopy or spectrophotometry ranges or cut-offs.

When the same hallmark can be associated with biological functions that can be monitored through different biological markers, the skilled person can decide to carry out one or more assay in order to monitor said function. In the example section and in the figures the definition of the acceptability ranges with different markers is provided, the results show that in each case, although different markers for analysing the modulation of the biological function/s selected, the result is consistent and, when the same spectroscopy technique is used, the resulting cut-offs are the same.

The skilled person will be able to select the more suitable markers depending on the selected hallmarks of the pathological condition of interest.

Said markers can be, by way of example, gene expression patterns, ROS, oxidative stress, cell viability and others.

According to a preferred, but not limited thereto, embodiment of the invention the method comprises the following steps:

i)

a. retrieving from the state of the art a list of the hallmarks of said pathological condition;

b. identifying for each of said hallmarks a set of biological functions modifications detectable in said pathological condition and determining the modulation of each of said functions concurring to the desired therapeutic effect thereby designing the modulation pattern of each of said functions representing a healthy physiological state;

c. identifying the genes and the expression pattern thereof underlying the modification detectable in said pathological condition for each of said biological functions and setting for each of said genes the expression pattern opposite to the one identified as the expression pattern indicative of said healthy physiological state;

ii) analysing the expression pattern of each of the genes identified in i) c. induced by a gold standard of said product in a suitable in vitro cell-based assay, determining the quali-quantitative modulation of the expression of each of said genes induced by said gold standard with respect to the pathophysiological state control of said in vitro cell based assay, and calculating the gold standard Z-score value of the modulation of each of said biological functions induced by said gold standard and selecting each of said gold standard Z-score values as reference cut-off Z-score indicative of said desired therapeutic effect;

iii) analysing the expression pattern of the genes identified in i) c. induced by further different batches of said product, in said in vitro cell-based assay and determining the quali-quantitative modulation of the expression of each of said genes induced by each of said batches thereby calculating the Z-score value of the modulation of each of said biological functions induced by each of said batches iv) comparing the Z-score value of the modulation of each of said biological functions induced by each of said batches calculated in iii) with the corresponding reference cut-off Z-score values and selecting at least three positive batches for which each Z-score value calculator in iii) complies with the corresponding reference cut-off Z-score values and at least one negative batch for which at least one Z-score value calculated in iii) does not comply with the corresponding reference cut-off Z-score value v) carrying out a spectroscopy or spectrophotometry analysis of said gold standard and of the batches selected in iv)

vi) defining the variability spectroscopy or spectrophotometry ranges resulting by considering each of the results obtained in v) as acceptable for each positive batch and non-acceptable for each negative batch thereby providing said acceptability spectroscopy or spectrophotometry ranges or cut-offs.

According to the invention the product subject to the batch to batch validation process of the invention and for which suitable acceptability ranges or cut-offs values are provided with the method of the invention is a product, comprising or consisting of one or more natural matrix, for use in the treatment of a pathological condition i.e. a product with a therapeutic effect verified at least preclinically in vitro on cells and/or tissues and/or organoids and/or animal models, and therefore a product expected to, when administered to a patient suffering of a given pathological condition, reduce the severity of the subject's condition (i.e. the severity is at least partially improved or ameliorated), and/or provide some alleviation, mitigation or decrease in at least one clinical symptom of said condition and/or delays in the progression of the said condition. The subject treated, according to the invention, is an animal including humans (hence the product is for human or for veterinary use), or even a plant.

The methods and processes provided in the present invention are, indeed, processes that can be carried out with the goal of validating batches of a given therapeutic product, comprising or consisting of natural matrices, in the production chain.

The product, as already stated above, is a product that comprises or consists of one or more natural matrix, i.e. of complex natural systems; a non-limiting example of said natural matrices is represented by one or more of: cut or pulverized plant parts, plant extracts, processed plant parts, fractions of plant extracts such as, for example, the fractions obtained by filtration on a semi-permeable membrane (microfiltration, ultrafiltration, nanofiltration) or by treatment on adsorption resins, microorganisms, honey, propolis, silk, wax, plant resins, plant gums, plant exudates, vegetable oils, vegetable essential oils, animal tissues lysates, plant or animal fluids.

Preferably, said microorganisms are inactivated microorganisms such as tyndallized organisms.

In a mostly preferred embodiment, the therapeutic product is a product consisting of 100% of natural components, intended as components that are not obtained by man through chemical synthesis reactions, therefore, when the product comprises one or more natural matrix, it can also comprise minerals, and in general any other organic or inorganic material found in nature. Preferably, the product subject to methods and processes of the invention, is a product obtained or obtainable according to a standardised protocol, more preferably through an eubiotic standardised protocol. When no standardised protocol is available, the skilled person can nevertheless minimise the differences between batches of the same products by using, for each natural matrix comprised in the product, a pool of a starting raw sources or of intermediate materials or of natural matrices. In this way, the inherent variability of natural matrices derived from different samples of the same kind of source (e.g. same plant from different cultivars), can be diminished by said pooling.

According to the invention said product can be a nutraceutical, a food supplement, a medical device, a medicament.

In an embodiment said product is a medical device as defined in EU Regulation 2017/745 Article 2 (1) indents 1-3 wherein the medical purpose is the treatment or alleviation of a disease or the modification of a pathological process or state.

Article 2 (1) indents 1-3 of EU Regulation 2017/745 recite:

For the purposes of this Regulation, the following definitions apply:

(1) 'medical device' means any [ . . . ] material or other article intended by the manufacturer to be used, alone or in combination, for human beings for one or more of the following specific medical purposes:
  - diagnosis, prevention, monitoring, prediction, prognosis, treatment or alleviation of disease,
  - diagnosis, monitoring, treatment, alleviation of, or compensation for, an injury or disability,
  - investigation, replacement or modification of the anatomy or of a physiological or pathological process or state,

[ . . . ]

and which does not achieve its principal intended action by pharmacological, immunological or metabolic means, in or on the human body, but which may be assisted in its function by such means. The product may also be a product classified as a medical device by the FDA.

Per Section 201(h)(1) of the Food, Drug, and Cosmetic Act, a device is:

An instrument, apparatus, implement, machine, contrivance, implant, in vitro reagent, or other similar or related article, including a component part, or accessory which is:

(A) recognized in the official National Formulary, or the United States Pharmacopoeia, or any supplement to them, (B) intended for use in the diagnosis of disease or other conditions, or in the cure, mitigation, treatment, or prevention of disease, in man or other animals, or (C) intended to affect the structure or any function of the body of man or other animals, and which does not achieve its primary intended purposes through chemical action within or on the body of man or other animals and which is not dependent upon being metabolized for the achievement of its primary intended purposes. The term "device" does not include software functions excluded pursuant to section 520(o).

The method of the invention is preferably carried out on a dry form of the product of interest, so when the final product intended for use is a solution, a suspension or other liquid forms, the method can be carried out on the lyophilised product prior to its rehydration.

In its final form for administration the product may be in the form of a powder, a granulate, a tablet, a syrup, a solution, a suspension, a hard or soft gelatine, a capsule, a spray, a cream or the like.

According to the invention, a pathological condition is a specific disease or a pathological state. A non-limiting example of pathological condition comprises mild cognitive impairment (MCI), osteoporosis (OP), including post or peri menopausal osteoporosis (PMO), osteoarthritis (OA), cancer.

Without limitation thereto, cancers of major interest such as head and neck cancer, melanoma, breast cancer, bladder and osteosarcoma are included.

Hallmarks of pathological conditions as well as of specific diseases are well-known in the art. The skilled person can easily retrieve in the scientific literature the hallmarks of pathological conditions of interest as well as the biological functions underlying said hallmarks. It evident that the skilled person will select the biological functions underlying a given hallmark taking into account the specific pathological condition of interest.

By way of example, the skilled person can investigate the patho-physiological state-of-the-art of the disease of interest using different prior art sources.

The skilled person wishing to define hallmarks of a disease of interest will be able to retrieve the desired information from the scientific literature. By way of example, non-limiting example of sources that can be used Robbins & Cotran Pathologic Basis of Disease (Robbins Pathology) 10th Edition; https://calgaryguide.ucalgary.ca/; Biomedical literature from PubMed Central (https://pubmed.ncbi.nlm.nih.gov/) and the like.

For each of said hallmarks a number of biological functions underlying them are also known in the art, the skilled person can select said functions from the ones disclosed in the art. When more biological functions are ascribed in the art to a given hallmark of a given pathology in the method of the invention, preferably at least two, at least three or more of said functions are selected.

When wishing to use specific software available for easily carrying out certain steps of the method of the invention such as finding biological functions underlying a hallmark of a disease, the skilled person may wish to adapt the retrieved hallmarks adapting their definitions in order to better interrogate the software used. By way of example, in case the software used is Qiagen IPA (IPA version 94302991 Qiagen), the information found in the aforementioned resources can be used, if necessary, to redefine said hallmarks to interrogate IPA. In order to rapidly identify the biological functions underlying a hallmark of a disease, when IPA is used, the following procedure can be followed:

Hallmarks can be written, one by one, in the "disease and functions" query box and the search is then launched.

The obtained resuming table allows the skilled person to filter disease/function that come from many lines of evidence. By way of example, the source for the relationship can be the Ingenuity Knowledge Base, including curation from journal articles, OMIM, JAX and ClinicalTrials.gov.

The tool is therefore able to associate with each biological function a defined number of genes whose regulation is able to influence the modulation of the biological function itself.

Examples of known hallmarks associated with pathological conditions are shown in FIGS. 1-4, 8-12.

Merely by way of example, hallmarks of OA known in the art comprise: Proliferation (Skeletal and muscular system development and function such as articular dysfunction and joint space); Inflammation; Anatomical damage. Still by way of example, suitable biological functions underlying the OA hallmarks above can comprise the following:

- Proliferation: the biological functions interested being skeletal and muscular system development and function such as articular dysfunction and joint space, articular disfunction, joint space and formation of the cartilage tissue,
- Inflammation: the biological functions interested being inflammatory disease, inflammation and nociception, inflammation of the joint,
- Protection from anatomical damage: the biological functions interested being organismal injury and abnormalities such as joint inflammation and swelling, difficulty moving a joint: osteoarthritis.

Possible state of the art keywords defining said functions are indicated in FIGS. 1-4.

Further, by way of example, known hallmarks of MCI may comprise Cognition (impairment), activation and viability (neuronal, decrease), Myelination and branching (decrease), Inflammation (increase), Skeletal and muscular system function (decrease).

- Cognition: the biological function interested being cognition and learning;
- Activation and viability: the biological function interested being development, differentiation of neurons, proliferation of neuronal cells;
- Myelination and branching: the biological function interested being branching of neurons, neuronal sprouting;
- Inflammation: the biological function interested being chronic inflammatory disorder;
- Skeletal and muscular system function: the biological function interested being proliferation of muscle cells and necrosis of muscle.

Possible state of the art keywords defining said functions are indicated in FIGS. 8 and 9.

Still by way of example, known hallmarks of OP, including PMO may comprise mineralisation, Inflammation (increase), bone adipose tissue (increase), remodelling of bone, osteoporosis, differentiation of osteoblasts (decrease).

- Mineralisation: the biological function interested being mineralisation of bone cell lines and osteoblasts, formation of bone;
- Inflammation: the biological function interested being inflammation of adipose, connective and white adipose tissue;
- Bone adipose tissue: the biological function interested being weight gain, transdifferentiation, differentiation of adipocytes;
- Remodelling of bone: the biological function interested being remodelling and resorption of bone;
- Osteoporosis: the biological function interested being osteoporosis itself;
- Differentiation of osteoblasts: the biological function interested being activation of alkaline phosphatase, differentiation of bone cells, differentiation of osteoblasts.

Possible keywords linked to said functions are indicated in FIGS. 9 and 10.

For each of said hallmarks biological functions underlying them are known in the art.

For each of said biological function the modulation causally related to the pathological condition is also known in the art, therefore the opposite modulation can be considered as the modulation concurring to the desired therapeutical effect, consequently, a panel indicating the desired modulation pattern of each of said functions can be designed, said panel being representative of the modulation trend of said functions in a healthy physiological state (see FIGS. 1-4, 8-11). Modulation in the present description is intended as up or down modulation of the given function. Up modulation refers to the modification in the activity, expression, of particular genes, proteins, cellular pathways or cellular components resulting in an enhancement of a given biological function. Downregulation is the opposite of upregulation. It involves a modification in the activity, expression of genes, proteins, cellular pathways or cellular components, leading to a reduction in a given biological function.

An non limiting example of the modulation of the biological functions causally linked to the pathological condition (OA, MCI and OP, including PMO) leading to the pathological condition is depicted in FIGS. 1-4 and 8-12.

Therefore, conversely, the healthy physiological state referred to the pathology of interest can be designed as the inverse modulation of each selected biological function. By way of example but not limited thereto, for OA, MCI and OP, in particular PMO, the modulation leading to the healthy physiological state is depicted in FIGS. 1-4 and 8-12.

When the modulation pattern leading to the healthy physiological state is observed upon treatment with a given product, for each or mostly of the biological functions causally related to the hallmarks of a given disease, then the product can be identified as a product having the desired therapeutic effect. Therefore, a product inducing the modulation of the biological functions causally related to the hallmarks of a given pathological condition in the direction toward the healthy physiological state, can be identified as a product having the desired therapeutic effect on the overall pathological state. When only some of the biological functions causally related to the hallmarks of a disease are in conformity with the physiological standing as defined above, then the product has only a partial therapeutic effect that does not satisfy the overall healthy physiological state.

When gene expression is selected as a marker, the genes and the expression pattern of each of said genes underlying the modification of each biological function causally linked to each selected hallmark of a pathological condition can be retrieved by the skilled person from the state of the art, this work can be facilitated by using ad hoc bioinformatics tools. The same Qiagen IPA indicated above is suitable for a fast sorting out of said information from scientific literature, as it is an aggregator of scientific references that allows to search for information on genes/proteins and the construction of networks that predict the behaviour of biological systems according to their gene expression status.

The patho-physiological features (hallmarks) available in the state-of-the-art for a given pathological condition are used to interrogate IPA via the "IPA Bioprofiler" tool, using them as key words, additional keywords related to said hallmarks can also be added.

The use of "IPA Bioprofiler" allows the skilled person to identify the expressed genes causally linked to each of the identified biological functions and the specific molecular pathway underpinning them. Information concerning the measured gene expression data (by way of example, following the manufacturer's instructions Fold change value cut-off $\leq -2$ and $\geq +2$ and p-value$\leq 0.05$) induced by each batch was then superimposed on the networks obtained, in order to define influenced genes and modulation of the connected biofunction.

Once the most relevant genes and the expression pattern thereof underlying the modification detectable in the pathological condition of interest for each of the selected biological functions are identified, for each of said genes the expression pattern opposite to the one identified is set as the expression pattern indicative of the healthy physiological state of said biological functions.

As stated above, modulation of biological activity is divided in down-modulation or up-modulation depending on the related genes regulation. The resulting expected calculated impact, based on the literature, on the related biofunctions can be determined by "IPA Molecule Activity Predictor" tool (MAP) and resumed in a heatmap visualization using a colour code that can easily be transformed into numeric values by the user.

Step ii) of the Method of the Invention Comprises:

ii) analysing the modulation of each of the markers identified in i) c. induced by a gold standard of said product in said in vitro cell-based assay, determining the quali-quantitative modulation of each of said markers induced by said gold standard and calculating the Z-score value of the modulation of each of said biological functions induced by said gold standard thereby providing the gold standard cut-off Z-score values of the modulation of each of said biological functions indicative of said desired therapeutic effect.

In vitro cell-based assays are well-known laboratory techniques that involve the use of isolated cells to study biological processes or test the effects of drugs, chemicals, or other substances.

According to the invention, cell culture models such as monolayer cultures, or three-dimensional (3D) systems can be used. When appropriate, disease-specific cell lines can be used, depending on the disease of interest (e.g. cancer) also proliferation assays can be used.

A suitable in vitro cell-based assay is an assay designed to mimic a disease e.g. due to the nature of the cells used, or by inducing a diseased phenotype in cells treated with specific compounds i.e. a "disease model assay" or "disease-in-a-dish" model.

Cell Type Selection: a cell line or primary cells relevant to the disease being modelled is selected. By way of example, if studying OA, a suitable and recognised cell-based assay is with chondrocytes that, upon treatment with IL1B, are a disease model of OA acknowledged in the art. Still by way of example, if studying neurodegenerative diseases, neuronal cell lines like SH-SY5Y, primary neurons may be selected or primary cells in which the desired phenotype can be induced by an "insult" with a given compound can be used.

For the study of Osteoporosis, in particular PMO, a suitable cell-based assay can be prepared by using Human, adipocyte-derived, mesenchymal stem cell lines (hADMSC), capable of differentiating into osteoblasts and mineralize the extracellular matrix (ECM) as described in the examples.

For the study of cancers, viability tests can be carried out on suitable (depending on the cancer of interest) cell based assays.

In case, e.g. ROS scavenging activity is a selected biological function, a suitable cell based assay can be carried out with a human fibroblast (HuDe) cell line insulted with a generator of ROS (e.g. AAPH 2,2'-azobis-2-methyl-propanimidamide, dihydrochloride) as known in the art.

For cell-based assays wherein the pathological state has to be induced by an insult, the assay cells can also be directly tested with the product of interest in order to verify that the modulation of the selected biological functions has the same trend of the modulation expected to lead to a healthy physiological state. This is particularly useful for assessing the beneficial (adjuvating homeostasis) effect of a product.

The cell-based assays preferably includes appropriate control groups, such as untreated cells, vehicle-treated cells, and cells treated with compounds known to have no impact on the disease phenotype. These controls help distinguish the specific effects of the tested compounds.

In case the markers and modulation pattern thereof correspond to the genes and the expression pattern thereof underlying the modification detectable in pathological condition for each the selected biological functions is analysed, a transcriptomics analysis on a suitable in vitro cell based assay representing the pathological condition of interest is carried out, and the genes and the expression pattern thereof underlying the modification detectable in the pathological condition for each of the selected biological functions can be identified. In the case in which the disease phenotype is caused by the administration of a specific agent to the cultured cells, the modification representing the pathological condition is the modification insulted cells vs. pre-insulted, untreated cells and the modification induced by the gold standard is the modification insulted cells vs. insulted cells+gold standard.

The transcriptomic analysis can be carried out with any suitable technique known in the art, including next generation sequencing and gene expression microarrays and the transcriptomic expression profile in the basal cells as opposed to the cells treated in order to mimic the pathological condition can be evaluated in order to identify the significantly differentially expressed genes and their expression patterns. According to the method of the invention, once the expression pattern of the significantly differentially expressed genes of the cells representing the disease phenotype vs. the cells before the insult inducing said diseased phenotype is assessed, the opposite expression pattern is considered representative of the healthy physiological state.

When gene expression is the selected marker, for each biological function identified in i) b. the genes and the expression pattern thereof underlying the modification detectable in said pathological condition for each of said biological functions can be identified from the state of the art using appropriate tools.

By way of example, the skilled person can derive this information using any suitable approach including using software specifically designed for this scope such as Ingenuity Pathway Analysis (IPA version 94302991 Qiagen).

The interpretation of high-throughput gene-expression data is greatly facilitated by the consideration of prior biological knowledge. This can been done using statistical gene-set-enrichment methods where differentially expressed genes are intersected with sets of genes that are associated with a particular biological function or pathway (Abatangelo, L. et al. (2009) Comparative study of gene set enrichment methods. BMC Bioinform., 10, 275). One more recent approach involves the application of causal networks that integrate previously observed cause-effect relationships reported in the literature (Chindelevitch, L. et al. (2012a) Causal reasoning on biological networks: interpreting transcriptional changes. Bioinformatics, 28, 1114-1121; Felciano, R. M. et al. (2013) Predictive systems biology approach to broad-spectrum, host-directed drug target discovery in infectious diseases. Pac. Symp. Biocomput., 2013, 17-28; Kumar, R. et al. (2010) Causal reasoning identifies mechanisms of sensitivity for a novel AKT kinase inhibitor, GSK690693. BMC Genom., 11, 419; Martin, F. et al. (2012) Assessment of network perturbation amplitudes by applying high-throughput data to causal networks. BMC Syst. Biol., 6, 54; Pollard, J. Jr. et al. (2005) A computational model to define the molecular causes of type 2 diabetes mellitus. Diabetes Technol. Ther., 7, 323-336). While still depending on statistics, this is more powerful than gene-set enrichment since it leverages knowledge about the direction of effects rather than mere associations.

In a preferred embodiment, the skilled person can follow the protocol provided in the publication by Kramer et al, Bioinformatics vol 30 no 4 2014, pages 523-530 "Causal analysis approaches in Ingenuity Pathway Analysis provides and discuss a suite of algorithms and tools for inferring and scoring regulator networks upstream of gene expression data based on a large-scale causal network derived from the Ingenuity Knowledge Base" or the manufacturer's instructions of (IPA version 94302991 Qiagen). The method and algorithms disclosed in the paper enable the skilled person to predict downstream effects on biological functions and diseases.

In the article, the authors describe causal analysis approaches that have been implemented in Ingenuity Pathway Analysis (IPA) with particular focus on the details of the underlying algorithms, and the application to a number of real-world use cases. In particular, points i) b. and i) c. can be readily carried out by the skilled person by using Ingenuity Pathway Analysis (IPA version 94302991 Qiagen) which is well-known pathway analysis application among the life science research community cited in tens of thousands of articles that allows to understand causal connections between and among diseases, genes and networks of upstream regulators.

Once the desired modulation of the biological function is defined (i.e. the one representing the healthy physiological state) and the desired regulation of the related marker (e.g. ROS scavenging activity, genes, etc.) is identified for the pathological condition of interest according to point i) of the method, an analysis of the selected marker modulation (e.g. for gene expression a transcriptomic analysis) in the same in vitro cell based assay representative of the pathological condition is carried out upon treatment of the cells, with a gold standard of the therapeutic product under examination is carried out. As already clarified previously, the gold standard has a previously assessed therapeutic or beneficial effect. The quali-quantitative modulation of the marker/s (e.g. of the expression of the genes of interest) induced by the gold standard is determined and Z-score values of the modulation of each of the selected biological functions are calculated and subsequently used as gold standard Z-score cut-off value of the modulation of each of said biological functions indicative of said desired therapeutic effect.

The gold standard of the product tested is, as stated above, a batch of the product of interest for which a therapeutic or beneficial effect has been assessed either in vitro or in vivo, preclinically or clinically. In any case it is a batch of the product of interest for which the therapeutic or beneficial effectiveness has been previously verified.

According to the method of the invention, the gold standard Z-scores values of the modulation of each biological function derived from the analysis carried out in ii) are taken as reference Z-score values that are representative of the desired therapeutic or beneficial effect. By way of example, when the desired modulation of the biological activity is an up modulation the cut-off Z-score value will be ≥the gold standard (reference) Z-score value, when the desired modulation of the biological activity is a down modulation the cut-off Z-score value will be ≤the gold standard (reference) Z-score value. The reference Z score values can be adjusted, as explained below, when the cell-based assay is carried out also on one or more reference drugs (i.e. drugs that are known in the art as indicate for the treatment of the pathological condition of interest. Said drugs are expected to modulate with the desired trend at least a part of the selected biological functions although, due to their different mechanism of action (SAR), said drugs are expected to modulate with the desired trend only some of said selected biological functions. Therefore, as explained in more detail below, the adjustment of the reference Z-score values taking into account also the drug Z-score values will be carried out only for said biological functions that are modulated by the tested drug in the same direction of the healthy physiological state.

The Z-score values in step ii) and in step iii) are calculated in order to represent the directionality and magnitude of the modulation for each biological function obtained exerted by a given batch of product. For transcriptomics, the Core analysis of the IPA version 94302991 Qiagen can be used by the skilled person to readily obtain the aforementioned Z-score values following the manufacturer's instructions.

In case the Core analysis does not yield sufficient relevant information, alternative approaches can be employed. An example of an alternative approach is provided below (overlay analysis). Step iii) of the method of the invention comprises:

iii) analysing the modulation pattern of the markers identified in i) c. induced by further different batches of said product in said in vitro cell-based assay and determining the quali-quantitative modulation of each of said markers induced by each of said batches thereby calculating the Z-score value of the modulation of each of said biological functions induced by each of said batches.

Step iii) is carried out as step ii) with different batches of the product of interest. As at least three batches that are compliant and one batch that is not compliant with the gold standard Z-score cut-offs are desired, the skilled person will analyse at least four additional batches of the product of interest.

Step iv) of the method comprises:

iv) comparing the Z-score value of the modulation of each of said biological functions induced by each of said batches calculated in iii) with the corresponding reference cut-off Z-score provided in ii) and selecting at least three positive batches for which each Z-score value of the modulation of each of said biological functions complies with the corresponding reference cut-off Z-score values and at least one negative batch for which at least one Z-score value of the modulation of each of said biological functions calculated in iii) does not comply with the corresponding reference cut-off Z-score values.

The batches of iii) that are considered compliant are batches for which each Z-score value resulting from the analysis of the expression pattern identified in i) c. is ≥the reference cut-off Z-score value when the desired modulation of the biological activity is an up modulation and ≤the reference cut-off Z-score value when the desired modulation of the biological activity is a down modulation, on the contrary, when at least one Z score value calculated in iii) does not fulfil the requirements above, the batch is considered non-compliant and can be used as a reference of not acceptability for the final assessment of the acceptability spectroscopy or spectrophotometry ranges or cut-offs.

According to a preferred embodiment of the invention, additional different batches of the product of interest can be analysed. In particular, when a batch X of the product of interest does not fall within the acceptability ranges or cut-offs defined with the method of the invention in the process of batch-to-batch validation of the invention, step iii) can be carried out for said batch and, in case it complies with the reference Z-score cut-offs defined in ii) batch X is considered compliant and the ranges or cut-offs of acceptability obtained with the method of the invention can be adjusted by considering compliant also batch X in the subsequent steps iv) v) and vi).

Additionally, if desired, step ii) of the method above may further comprise analysing the expression pattern of the markers identified in i) c. induced by one or more reference drug for the treatment of said pathological condition in said in vitro cell-based assay and determining the quali-quantitative modulation of the expression of each of markers induced each drug and calculating the drug Z-score value of the modulation of each of said biological functions induced by each of said drug. For each biological function modified also by said one or more drug in the direction of the healthy physiological state, the reference Z-score value can be adjusted by comparing the drug Z-score value and the gold standard Z-score value, and selecting as reference cut-off-Z score value the Z-score value associated to the weakest performance.

As conventional drugs are expected to modulate in the desired direction only part of the selected biological functions due to their mechanism of action (SAR), only the Z-scores values related to the functions that are modulated in the same direction of the healthy physiological state will be taken into account.

As known by the skilled person, reference drugs for the treatment of a pathological condition may be known a priori to provide a therapeutic effect only on one or few hallmarks of the disease. In this case, the information that will be integrated in the method of the invention will relate only to the interested hallmarks and related biological functions.

In a not limiting embodiment of the invention steps i) to iv) can be carried with the aid of IPA version 94302991 Qiagen out as follows:

i) a. to c.

Definition of patho-physiological state of the art of the disease and of the patho-physiological hallmarks of the disease with which to interrogate IPA The patho-physiological state-of-the-art of the disease of interest is investigated using different specific sources:

- Robbins & Cotran Pathologic Basis of Disease (Robbins Pathology) 10th Edition
- https://calgaryguide.ucalgary.ca/
- Biomedical literature from PubMed Central (https://pubmed.ncbi.nlm.nih.gov/) The information found in the aforementioned resources are used to identify hallmarks to interrogate IPA by the following procedure:
- Hallmarks are written, one by one, in the "disease and functions" query box and the search is then launched.
- The obtained resuming table allows you to filter disease/function that come from many lines of evidence. The source for the relationship is the Ingenuity Knowledge Base, including curation from journal articles, OMIM, JAX and ClinicalTrials.gov.

In silico model will be limited to genes and mRNAs.

The tool is therefore able to associate with each biological function a defined number of genes whose modulation is able to influence the modulation of the biological function itself.

ii) and iii)

The following applies to any step of the method of the invention in any embodiment herein described, wherein an in vitro cell based assay is carried out treating the cells with the disease phenotype with a given compound, be it the golden standard, a different batch of the product of interest, a reference drug and the like.

Transcriptome Raw Data Analysis

Whole transcriptome expression profile is evaluated in the in vitro cellular model representing the disease for control cells and for model cells. A Human Clariom™ S Pico Assay HT (Applied Biosystems, ThermoFisher Scientific) on a GeneTitan MC Instrument (Applied Biosystems, ThermoFisher Scientific), can be used following the manufacturer's instructions. CEL Intensity files can be generated by Affymetrix GeneChip Command Console Software (AGCC, ThermoFisher Scientific). Data analyses can be performed using Transcriptomic Analysis Console Software (TAC, ThermoFisher Scientific) that provides quality control analysis, performs normalization and summarization, based on the Signal Space Transformation-Robust Multi-Chip Analysis (SST-RMA) analysis algorithm, and provides a list of differentially expressed genes (Limma Bioconductor package). This phase allows the user to obtain a list of differentially expressed genes (DEGs), identified based on their expression fold changes with respect to a relevant control experimental condition, in this case one that reproduces the pathological state in vitro.

The transcriptional modifications profile thus obtained is subjected to a functional pathway enrichment analysis. One of the commercial tools that can be used is Ingenuity Pathway Analysis (IPA version 94302991, Qiagen) [Krämer et al. (2014)]. The use of IPA allows the user to estimate how and to what extent the modulation of gene expression in the cellular system (cell based assay) influences the biological functions related to the pathology of interest.

IPA Pre-Analysis Filtering (Contextual Data Analysis) of Transcriptional Profile In preparation for subsequent analyses, transcriptomic profiles undergo a filtration process to identify relevant genes and their corresponding measurement values. This filtration aims to select only significantly perturbed genes, as indicated by their fold change compared to the pathological condition. Typically (e.g. as according to the manufacturer's instructions), the fold change threshold is set to encompass values $\leq -2$ and $\geq +2$, accompanied by a statistical significance denoted by a p-value of $\leq 0.05$. However, the skilled operator has the flexibility to adjust the cut-off based on their expertise, considering the successful performance of negative controls (a sample representing the pathological state) or reference standard known to be able to counteract fully or partially the pathological state.

The possible methodological approaches to extract biological meaningfulness from a list of modifications of gene expression profiles through IPA can be of two types: "Core analysis" and "Overlay analysis of in silico model of patho-physiological state" (abbreviated as overlay analysis).

At this stage of the procedure, hence, two different, alternative, options can be pursued.

Core Analysis

The list of Differentially expressed genes (DEGs) after administration of the gold standard or of any other product batch/reference drug or other, and corresponding data measurement values (fold change with respect to pathological state) identified in the different experimental conditions are uploaded into the application. Available identifiers are mapped to their corresponding entity in QIAGEN's Knowledge Base.

By launching a "Core Analysis", significantly perturbed DEGs, called Network Eligible molecules, are overlaid onto a global molecular network developed from information contained in the QIAGEN Knowledge Base. Networks of Network Eligible Molecules are then algorithmically generated based on their connectivity.

The core analysis provides a comprehensive list of approximately top 500 biological functions derived from the generated networks. The associations Biological functions-genes are always supported by annotations corresponding to scientific peer review publications that substantiate, through the automatic association of a Z-score [Krämer et al. (2014)], the calculated directionality and magnitude of modulation of the biological functions. In essence, this value represents a statistical metric that assesses the similarity between the observed pattern of Differentially Expressed Genes (DEGs) and the expected pattern based on existing literature for a given annotation. It is the responsibility of the proficient operator to carefully choose the biological functions that are relevant to the specific pathology under investigation. The selection of biological functions will be structured based on the identified hallmarks of the pathology of interest.

The associated Z-score values will then be used to indicate the directionality and magnitude of modulation for each biological function.

Overlay Analysis

If the core analysis does not yield sufficient relevant information, an alternative approach called "Overlay analysis" can be employed. This analysis focuses on the biological functions identified by the "in silico model of the patho-physiological state". The selection of biological functions is structured based on the identified hallmarks of the pathology of interest.

The "Overlay analysis" is structured by establishing relationship between patterns of differentially expressed genes and selected biological functions (always supported by annotations corresponding to scientific peer review publications that substantiate the directionality and magnitude of modulation of the biological functions) using the following procedure:

- Import the set of biological functions selected from the in silico model of the patho-physiological state into a new sheet called "my pathway."
- Utilize the "Build tool" and "Grow tool" to identify Differentially Expressed Genes (DEGs) belonging to the transcriptomic profile under investigation and are linked to regulation of the biological functions selected in the previous step.
- Modulation of the identified DEGs is represented using green colour (indicating down-modulation) and red colour (indicating up-modulation).
- To determine the expected calculated impact of such experimentally observed modulations of gene expression on biological functions activity, the "Overlay" and "Molecule Activity Predictor" tool (MAP) are employed. The "Prediction" function is activated within MAP tool to calculate the resulting expected modulation of biological functions. Colour coding is thus established:

orange: increase in activity
blue: decrease in activity
white: not achievable/not predictable As the "Overlay analysis" does not directly calculate the Z-score for each biological function but provides results in terms of colours indicating the direction of the modification and intensity of the colour signal proportional to the magnitude of the modulation of interest, it is necessary to translate the intensity of the modulation signal (graphically represented in the "my pathway" tab) into a numerical value. This is achieved by converting the colour intensity obtained for each biological function into a Z-score.

One of the possible tools that can be used for this purpose is "IPAmap_Parser" app, a web port app of Pipeline Pilot that aims to assign a score, called z-score, to genes and biofunctions based on their coloration within a biological pathway generated by QIAGEN's Ingenuity Pathway Analysis software. The key step of the algorithm is the conversion from the RGB colour model to the LAB model (https://www.xrite.com/it-it/blog/lab-color-space posted on October 2018 by Tim Mouw), a colorimetric coding that also allows the intensity of the colour to be recorded and not just the RGB composition. This conversion occurs within a Pipeline Pilot "component" that uses a procedure written using R software that is based on specific features of the colorspace package (https://cran.r-project.org/web/packages/colorspace/index.html, details can be found on Zeileis et al 2020journal of statistical software, doi: 10.18637/jss.v096.i01). The Z-score allows for an objective comparison of the impacts of different treatments.

When the above protocol is carried out with the gold standard, and optionally with one or more reference drug, the Z-score values obtained for each biological function modulation as disclosed above are considered the reference cut-off Z-score values for the desired modulation of said function, therefore, when the desired modulation is an up modulation the cut-off Z-score value will correspond to ≥the reference Z-score value obtained according to the present description, when the desired modulation is a down modulation the cut-off Z-score value will correspond to ≤the reference Z-score value obtained according to the present description.

In case one or more reference drug is also tested in the selected in vitro cell based assay, the modulation Z-score values observed for the biological functions that are known to be modulated by said reference drug, can be taken into account in order to establish the compliance criteria, i.e. the cut-off Z-score values to be used in iv).

A reference drug is a drug recommended by the clinical guidelines for treating the pathology or the hallmark of interest.

When a reference drug modulates one or more biological function associated with hallmarks of the pathological condition of interest is also tested in the in vitro cell based assay, both the Z-score obtained with the gold standard and with the reference drug are considered effective for said one or more biological function, therefore, the value associated to the weakest performance is assumed as to identify the lower limit of compliance for each of said one or more biological function and will be considered the cut-off Z-score to refer to in point iv).

Step v) of the Method Comprises:

v) carrying out a spectroscopy or spectrophotometry analysis of said gold standard and of the batches selected in iv)

A non-limiting example of spectroscopy analysis according to the invention is Near InfraRed Spectroscopy (NIR), Fourier Transformed InfraRed (FTIR), Raman Spectroscopy, Spectrophotometry, such as, e.g. UV-VIS (UV-Visible), fluorescence spectroscopy, light scattering.

According to a preferred embodiment of the invention said spectroscopy analysis is carried out by NIR. Indeed, as the skilled person knows, NIR spectroscopy is a vibrational spectroscopy technique that provides qualitative information about the chemical species present in the material analysed together with information about its physical state. Performing NIR analysis means subjecting the material to light of different wavelengths and measuring the vibration of the material at each wavelength. The vibrations detected depend on the composition and on the interactions between the components, which affect the vibrational capabilities of each component placed within the matrix. This analysis generates a vibrational footprint specific to that material.

The analysis of the NIR Fingerprint allows the reconstruction of a chemical-physical profile characteristic of the molecular composition of each analysed sample that is influenced by the chemical surroundings. Indeed, the molecules within the sample can form bonds between them, in particular hydrogen bonds, both intermolecular and intramolecular. This leads to an alteration of the vibration frequencies of both stretching and bending of the hydrogen atom and result in a shift in vibrational frequencies with respect to the single isolated molecule. For this reason, NIR spectrometry can be an excellent means of characterizing complex matrices. This technique, is therefore particularly suitable for the analysis of natural matrices as it provides a fingerprint of the whole matrix network and of the interactions between the components of the matrix.

An example of the NIR spectral profiles is shown FIG. 6.

Step vi) of the Method Comprises:

vi) defining as acceptable the variability spectroscopy or spectrophotometry ranges resulting by the considering each the results obtained in v) as acceptable thereby providing said acceptability spectroscopy or spectrophotometry ranges.

The ranges obtained will depend on the spectroscopy or spectrophotometry technique used and on the product tested.

Independently of the spectroscopy or spectrophotometry techniques used, the common feature is that each of the batches selected in iv) and the gold standard are set a priori as valid and acceptable products due to their assessed effect on the selected biological functions.

When NIR is used the acceptability cut-off obtained with the method of the invention are suitable for use in NIR conformity tests for batch-to-batch compliance (i.e. validation of the batch for production).

It is evident that the conformity tests have to be carried out with the same spectroscopy or spectrophotometry technique used for the assessment of the acceptability ranges or cut-offs.

In order to define the acceptability cut-off, the complete NIR spectrum of all the samples selected in iv) and of the gold standard is acquired, the spectra are aligned and normalised (Standard Normal Variate) and the wavelength (λ) regions of interest of the spectra are hence defined and the average spectrum of the spectra of all the compliant (positive) samples+gold standard is generated.

The average spectrum obtained will be the reference spectrum over the whole procedure.

In the execution of a NIR conformity test for pharmaceutical API-based products, pre-processing comprises (SNV) as indicated above, definition of the λ regions of interest, and the Max Conformity Index Value is normally used in the conformity tests and is conventionally imposed as 3.5 which means that the highest value of standard deviations accepted for pharmaceutical products in any point of the spectrum is normally 3.5.

In the method disclosed herein the acceptability ranges or cut-offs are not based on the quali-quantitative analysis of specific chemical substances in said product but on the modulation activity exerted by said product on selected biological functions, therefore, the Max Conformity Index (MCI) Value conventionally imposed in the quality controls for classical APIs, which is related to the quali-quantitative chemical composition, cannot be considered as a priori acceptable and the value is hence assigned based on the spectra of the batches selected in iv) and the gold standard.

In addition, Sum 2 (which derives from CI but also takes into account NIR spectra of one or more undesired samples), which is more suitable for heterogeneous samples, is preferably used as acceptability parameter according to the present invention.

According to this embodiment of the invention, the CI (Conformity Index) limit to which the conformity test will be pre-processed, corresponds to the maximum value of CI MAX (also defined herein as CI limit) defined by the spectra of the batches selected in iv) and the gold standard.

Therefore, according to the present invention the acceptability ranges or cut-offs of the spectroscopy or spectrophotometry analysis are defined on the basis of the modulation activity on each selected biological function exerted by the gold standard and batches of the product that are compliant with the gold standard in said modulation.

In the case of a NIR spectroscopy, hence, the CI limit i.e. the acceptability cut-off is calculated according to the following formula:

$$CI = (A_{reference,i} - A_{sample,i})/s_{reference,i}$$

Where $A_{reference,\ i}$=average absorbance at a given wavelength(i) of the reference (average spectrum)

$A_{sample,\ i}$=absorbance at a given wavelength(i) of the test sample $s_{reference,\ i}$=standard deviation at a given wavelength(i) of the reference (average spectrum)

In conformity tests related to heterogeneous samples, as indicated above, the Sum2 parameter is more suitable.

$$\text{Sum 2} = (\text{Sum of All } CIs > CI \text{ limit} - CI \text{ limit})/ \\ (\text{Sum of the number of points in the spectrum with } CI > CI \text{ limit})$$

Selecting the appropriate parameter in a conformity test depends on the user-specific control problem that can be easily addressed by the skilled person, in the case of products comprising or consisting of one or more natural matrix, i.e. extremely heterogeneous samples, Sum 2 is a suitable parameter.

In one embodiment of the invention, Sum2 parameter is selected for determining the acceptability cut-off of the conformity test.

Depending on the spectroscopy or spectrophotometry used, the acceptability ranges or cut-offs are calculated mutatis mutandis, with the same ratio used for NIR spectroscopy, i.e. by defining acceptable the values obtained from the batches selected in iv) and the gold standard.

When carrying out the process for the compliance validation process of one or more batches of a product (conformity test) comprising complex natural systems for the treatment of a pathological condition, according to the present invention, a batch may result, in a first analysis, not compliant.

In that case, it may be of interest to verify whether the non-compliance result is caused by an effective non-compliance of the batch with the desired modulation of the biological functions (i.e. the therapeutic effect) or is due to acceptability parameters that can be broadened and therefore an adjustment of said parameters can be made.

According to the method of the invention, step iii) can be repeated for said batch and, if the Z-score value of the modulation of each of said biological functions complies with the corresponding cut-off Z-score values, the acceptability ranges or cut-offs are corrected by defining the previously resulting non-compliant batch as compliant (re-calculating the acceptability ranges or cut-offs).

The highest is the number of compliant batches identified in step iv), the more accurate the acceptability ranges or cut-offs obtained with the method of the invention will be. Therefore, in an embodiment, according to the method of the invention, iii) is carried out on one or more additional different batch of said product (e.g. or more batch resulting at a first screening with a non-acceptable spectroscopy or spectrophotometry or merely additional batches in order to increase the number of acceptable batches according to step iv) of the method) and the one or more additional batch for which the Z-score value of the modulation of each of said biological functions complies with said corresponding cut-off Z-score values is subjected to the same spectroscopy or spectrophotometry analysis carried out in v) and the acceptability ranges or cut-offs defined in vi) are recalculated by defining also each of said batches as acceptable.

Furthermore, the method may also comprise, in any of the embodiments herein disclosed, further steps comprising:

vii) carrying out a spectroscopy or spectrophotometry analysis of one or more a priori undesired batch of said product and verifying that said one or more undesired batch does not result within the acceptability ranges or cut-offs defined in iv), and, in the negative (i.e. when the batch results within the acceptability ranges of cut-off defined in iv))

viii) defining new, narrower, variability spectroscopy or spectrophotometry ranges or cut-offs resulting by considering each the results obtained in vii) as non-acceptable.

The addition of the steps above can be desired by the product manufacturer in order to make sure that batches that may result from a formulation error expectable from the production chain, such as the absence of an ingredient or the like are excluded a priori from the acceptability ranges or cut-offs.

The invention also provides a method for assessing a gold standard of a product for use in the treatment of a pathological condition, comprising one or more natural matrix, comprising the following steps:

i)

d. retrieving from the state of the art a list of the hallmarks of said pathological condition and one or more reference drug for the treatment of said pathological condition;

e. identifying for each of said hallmarks a set of biological functions modifications detectable in said pathological condition and determining the modulation of each of said functions concurring to the desired therapeutic effect thereby designing the modulation pattern of each of said functions representing a healthy physiological state;

f. identifying the markers and the modulation pattern thereof underlying the modification detectable in said pathological condition for each of said biological functions and setting for each of said markers the modulation pattern opposite to the one identified as the modulation pattern indicative of said healthy physiological state;

ii')

analysing the modulation pattern of each of the markers identified in i') c. induced by said one or more reference drug in said in vitro cell-based assay, determining the quali-quantitative modulation of the expression of each of said genes induced by said one or more drug with respect to the pathophysiological state control of said in vitro cell based assay, and calculating the Z-score value of the modulation of each of said biological functions induced by said one or more drug providing the reference cut-off Z-score values of the modulation of each of said biological functions indicative of said desired therapeutic effect, iii') analysing the modulation pattern of the markers identified in i') c. induced by more than one different batch of said product in said in vitro cell-based assay and determining the quali-quantitative modulation of the expression of each of said genes induced by each of said batches thereby calculating the Z-score value of the modulation of each of said biological functions induced by each of said batches iv') comparing the Z-score value of the modulation of each of said biological functions induced by each of said batches calculated in iii') with the corresponding reference cut-off Z-score values and selecting as gold standard the batch for which each Z-score value of the modulation of each of said biological functions provides the best performance Z-score value with respect to the corresponding reference cut-off Z-score values.

Steps i') a to c are carried out, mutatis mutandis, as steps a') a to c as described above and in the examples.

Also steps ii') iii') and iv') are carried out, mutatis mutandis, as steps ii), iii) and iv) of the method described above and in the examples.

The markers and modulation patterns thereof as described above for the method for defining the acceptability ranges or cut-offs of a spectroscopy or spectrophotometry analysis for the validation of one or more batches of a product apply mutatis mutandis to the method for defining a gold standard. Hence, in an embodiment, said markers are genes and the modulation thereof is their expression pattern.

Finally, the invention provides a process for the compliance validation (i.e. quality control, compliance) of one or more batches of a product for the treatment of a pathological condition, said product comprising one or more natural matrix (as defined above), comprising the following steps:

a. carrying out a spectroscopy or spectrophotometry (as defined above) analysis of each batch of interest b. validating as compliant each batch for which the obtained spectrum satisfies the acceptability ranges or cut-offs identified according to the method described above and in claims 1 to 10, using the same spectroscopy analysis technique used for the definition of said acceptability ranges of cut-offs.

Given the fact that the method of the invention provides reliable parameters for use in the batch to batch validation for the compliance of products comprising or consisting of one or more natural matrix, the skilled person will readily understand that the method of the invention can also be applied, mutatis mutandis, for defining the acceptability ranges or cut-offs of a spectroscopy or spectrophotometry analysis for the validation of one or more batches of a product adjuvating the homeostasis of a subject's system, organ or apparatus comprising or consisting of one or more natural matrix; comprising a step in which said acceptability ranges or cut-offs are calculated on a spectroscopy or spectrophotometry spectra of a gold standard of said product, said gold standard having an ascertained homeostatic adjuvant effect in the maintenance of a healthy physiological state of said system organ or apparatus, and one or more different batches of said product; wherein said spectra are defined as acceptable on the basis of the biological activity exerted in a cellular-based assay by said gold standard and said one or more different batches of said product on one or more biological functions underlying said healthy physiological state.

In this case, the desired adjuvation of homeostasis in a specific system, district, apparatus or organ can be assessed by carrying out points 1 a to c of the method described above, thereby assessing the healthy physiological state of a given system, district, apparatus or organ and using the gold standard of a product that modulates the selected biological function with the same trend of the healthy physiological state. In any part of the description and of the claims the term "comprising" can be replaced by "consisting of".

The examples below are not intended as limiting the present invention.

EXAMPLES

1. Tested Products Composition

| | Arté GX (FIGS. 2-6) |
|---|---|
| Centella Asiatica dry Leaves | 90% w/w |
| Echinacea purpurea dry Flowers | 10% w/w |
| Coextracted in water | |

| | Product B (FIG. 10) |
|---|---|
| Melissa officinalis leaves dry extract | 1% w/w |
| Royal jelly lyophilised | 1% w/w |
| Blueberry dry extract | 0.29% w/w |
| Concentrated blueberry juice | 5% w/w |
| Concentrated apple juice | 47% w/w |
| Clarified lemon juice | 0.5% w/w |
| Honey | 35% w/w |
| Deionised water | 6% w/w |
| Malpighia emarginata juice | 1% w/w |
| Sambucus nigrum juice | 2% w/w |

| | Product C |
|---|---|
| Coral calcium powder | 19.35% w/w |
| Egg shell calcium powder | 19.35% w/w |
| Coral calcium citrate powder | 9.40% w/w |
| champignon mushroom dry extract | 0.05% w/w |
| Equisetum arvense dry aqueous extract | 1.37% w/w |
| Malpighia emarginata dry extract | 1.50% w/w |
| Cane sugar impalpable powder | 48.95% w/w |

2. In Vitro Cell Assay Representative of Osteoarthritis

An in vitro cellular model capable of recapitulating features of osteoarthritis [1-3] was established by exposing primary human chondrocytes (HC, Cell Application INC 402K-05) to IL1B [5 ng/ml] for 6 hours followed by 24 hours of exposure to five different batches of "Arté-GX" [1.4 mg/ml]:

Batch 20B1955 (gold standard)
Batch 2011279
Batch 20J1770
Batch 20B0596
in a successive moment, Batch 21E1640 as well as an aliquot of said batch that was treated in order to induce destabilisation of the product, herein referred as Batch DEST 21E1640, were also analysed (see FIGS. 3 and 4).

Each time one of the batch solutions was added, fresh IL1B [5 ng/ml] was also added to the medium.

2.1.1. Time Schedule on Chondrocyte Experiment

The time schedule used for experimental setting is as follows:

1. IL1B pre-treatment (5 ng/ml) for 6 hours, followed by treatment administration with IL1B (5 ng/ml) for 24 hours, followed by gene expression analysis;
2. IL1B pre-treatment (5 ng/ml) for 6 hours, followed by vehicle administration with IL1B (5 ng/ml) for 24 hours, followed by gene expression analysis.

2.1.2. Gene Expression Analysis

At the end of described treatment periods, cells were washed with 100 μl PBS and lysed and collected in RLT buffer (Qiagen, 1053393) added with β-mercaptoethanol (Sigma, M3148) and DX reagent (Qiagen, 19088) for gene expression analysis experiments. Total RNA was extracted from cells lysates using an QIAsymphony RNA Kit (Qiagen) with the QIAsymphony SP instrument (Qiagen).

The quality and quantity of RNA was determined by A230, A260, A280 and A320 measurements on Varioskan™ LUX multimode microplate reader (Thermo Scientific™). Integrity of RNA was checked using a 2100 expert_Eukaryote Total RNA Nano Kit (Agilent). Whole transcriptome expression profile was evaluated using a Human Clariom™ S Pico Assay HT (Applied Biosystems, ThermoFisher Scientific) on a GeneTitan MC Instrument (Applied Biosystems, ThermoFisher Scientific), following the manufacturer's instructions. Briefly, 6 ng of total RNA was used to generate cDNA, then fragmented and labelled cDNA was hybridized to a Human Clariom S 96-array plate for 17 h at 45° C. Arrays were washed, stained and then scanned using the GeneTitan MC Instrument (Applied Biosystems, ThermoFisher Scientific) and CEL Intensity files were generated by Affymetrix GeneChip Command Console Software (AGCC, ThermoFisher Scientific).

2.1.3. Transcriptomics Data Analysis

Data analysis was performed using Transcriptomic Analysis Console Software (TAC, ThermoFisher Scientific) that provides quality control analysis, performs normalization and summarization, based on the Signal Space Transformation-Robust Multi-Chip Analysis (SST-RMA) analysis algorithm, and provides a list of differentially expressed genes (Limma Bioconductor package, p-value≤0.05).

2.1.4. Bioinformatic Modelling of Experimentally Observed Transcriptomics Data

Ingenuity Pathways Analysis (IPA) (QIAGEN \Inc., https://www.qiagenbioinformatics.com/products/ingenuitypathway-analysis) [4] was used, for each investigated batch to evaluate modulations of gene expression relevant for effects of interest.

IPA is an aggregator of scientific references that allows to search for information on genes/proteins and the construction of networks that predict the behaviour of biological systems according to their gene expression status.

The patho-physiological features of state-of-the-art "Osteoarthritis condition" were considered with particular attention to the following areas involved:

| Keywords used to interrogate IPA | Chosen biological function |
|---|---|
| Osteoarthritis [osteoarthrosis] Arthralgia/arthritis arthropathy | Non-traumatic arthropathy; Osteoarthritis |
| Damage of cartilage tissue cartilage tissue | Formation of cartilage tissue |
| Inflammation of joint Pain of joint | Inflammation of joint |

This knowledge was used to interrogate IPA via the "IPA Bioprofiler" tool, using the following key words: osteoarthritis, arthropathy, formation of cartilage tissue, destruction of cartilage tissue, damage of cartilage, connective tissue disorder, inflammation of joint, immune cell trafficking, oxidative stress and hyaluronic acid. The use of "IPA Bioprofiler" allowed to identify clusters of expressed genes causally linked to each of the identified biological functions and the specific molecular pathway underpinning them. Information concerning the measured gene expression data (Fold change value cut-off ≤−2 and ≥+2 and p-value≤0.05) induced by each batch was then superimposed on the networks obtained, in order to define influenced genes and modulation of the connected biofunction.

Modulation of expressed genes were shown in different intensities of blue (signifying down-modulation) or red (signifying up-modulation). The resulting expected calculated impact, based on the literature, on the related biofunctions was determined by "IPA Molecule Activity Predictor" tool (MAP) and resumed in a heatmap visualization.

The colour and intensity thereof were transformed into numerical values.

2.1.5. Results

The results of these tests yielded a comparative study of the performance and of the mechanism of action of five different batches of Arté GX. The analysis revealed that while all batches were capable of returning reproducible biological effects, it was also possible to identify batch-specific fluctuations in the induced transcriptional pattern. Evidently the induction of slightly different transcriptional patterns still results in the same desirable regulation of biological functions. This is due to a functional redundancy in the interactions between the components of the product and the body, whereby, by virtue of the multifocal mechanism of action, slightly different compositions elicit the same effect (FIGS. 3 and 4).

The five batches are therefore considered as having equivalent biological outputs since the induction and repression patterns are conserved.

The different transcriptional patterns and relative biological effects of different batches is to be intended as the hallmark of the inherent variability present in a preparation constituted of biological material. From the results summarised in FIG. 4 it is evident that the observed transcriptional patterns of the five different batches elicit a very reproducible biological effect leading to a general modification of the pathological processes and of the overall pathological state equivalence for all the batches reported in FIG. 4.

3.1. Targeted Metabolomics

In order to appreciate whether the final matrix constituting "Arté GX" is characterized by the matrix effect, a series of analyses in order to grasp the product's features on different aspects was carried out on the batches reported above. A targeted metabolomics analysis capable of identifying the vast majority of such molecular components, was carried out together with the other analysis reported herein.

The products, as described above, consist of two vegetal matrices assembled and resulting in a final new vegetal matrix. Several analytical techniques have been used to identify and quantify compounds belonging to the main classes present in plants. Although metabolomic analysis does not allow to appreciate the dynamic changes within the component of the matrix, it allows a "picture" of the composition in the moment the analysis is carried out.

In the following analysis each individual component (plant metabolite) is specifically researched, for this reason the analysis is called "targeted metabolomics". This analysis allows to capture a frame on the qualitative data, by determining the chemical compounds present in the material, and quantitative data, by defining the concentrations of each compound in the material.

For Arté GX, a qualitative and quantitative characterization of as many primary and secondary metabolites as possible was carried out using an "omic" approach, the targeted metabolomics analysis, based on the use of multiple analytical methodologies. The analytical methods used for the chemical characterization of each batch are described below. The most appropriate analytical techniques have been adopted based on the chemical nature of the classes of compounds present. The analysis with chromatographic methods combined with different detection techniques (e.g. GC and LC each combined with a suitable detector), made it possible to identify and quantify, as appropriate, the organic compounds. The inductively coupled plasma analysis using a single quadrupole mass spectrometer (ICP-MS) or an optical emission spectrometer (ICP-OES) made it possible to establish the levels of elements present, while the anions were determined by ion chromatography and conductivity detector. Other gravimetric methods were used for the determination of classes of substances non-quantifiable by means of chromatographic methods.

The table below summarizes all the methods used.

| Class of Compounds | Characteristics | Type of Method | Short description |
|---|---|---|---|
| Fibres | Insoluble Fibers | Gravimetric | Method AOAC 991.42 (A1) |
| | Soluble fibres | Gravimetric | Method AOAC 993.19 (A2) |
| | FOS, Fructans | HPAEC-PAD | Extraction of FOS and Fructans followed by enzymatic digestion; analysis by ion chromatograph equipped with a pulsed amperometric detector. (A3) |
| Polysaccharides | Polysaccharides ≥ 20.000 Dalton | HPLC-RID | Extraction of water-soluble polysaccharides and analysis by HPLC equipped with molecular exclusion column and refractive index detector. (B) |

-continued

| Class of Compounds | Characteristics | Type of Method | Short description |
|---|---|---|---|
| Water | Loss on drying | Gravimetric | Method ISTISAN 1996/34 (pag 7-10). (C) |
| Phenols | Phenols polar | UHPLC-qToF | Sample extraction and reverse phase chromatography analysis by UHPLC coupled to a quadrupole-time-of-flight mass spectrometer. (D1) |
| | | HPLC-UV | Sample extraction and reverse phase chromatography analysis by HPLC coupled to UV-VIS detector. (D2) |
| Terpenes | Terpenes polar | UHPLC-qToF HPLC-UV | Sample extraction and reverse phase chromatography analysis by UHPLC coupled to a quadrupole-time-of-flight mass spectrometer. (E1) Sample extraction and reverse phase chromatography analysis by HPLC coupled to UV-VIS detector. (E2) |
| | Terpenes apolar | GC-TQ | Headspace analysis of the sample by gas chromatograph coupled to a triple quadrupole mass spectrometer. (E3) |
| | Sterols | GC-FID | Analysis of the sample by gas chromatograph coupled to a flame ionization detector, after derivatization and transformation into trimethylsilyl ethers. (E4) |
| Organic acids | Organic acids mono-, di-, tri-carboxylic | HPLC-UV | Sample extraction and analysis by HPLC coupled to UV detector. (F) |
| NITROGEN Compounds | Nitrogen-containing substances, total | Kjeldahl | Method AOAC 920.53. (G) |
| Lipids | Fats, total | Gravimetric | Method ISTISAN 1996/34 (pag 39-40). (H1) |
| | Fatty acids derivatives | GC-TQ | Headspace analysis of the sample by gas chromatograph coupled to a triple quadrupole mass spectrometer. (H2) |
| | Fatty acids | HPLC-UV | Sample extraction and analysis by HPLC coupled to UV detector. (H3) |
| | Fatty acids | GC-FID | Analysis of the sample by gas chromatograph coupled to a flame ionization detector, after derivatization. (H4) |
| Sugars and Derivatives | Monosaccharides | IC-PAD | Sample extraction and analysis by ion chromatograph coupled to pulsed amperometric detector. (I) |
| | Disaccharides | IC-PAD | Sample extraction and analysis by ion chromatograph coupled to pulsed amperometric detector. (I) |
| Other Organic Compounds | Other organic compounds, apolar | GC-TQ | Headspace analysis of the sample by gas chromatograph coupled to a triple quadrupole mass spectrometer. (L) |
| Inorganic Compounds | Elements | ICP-MS, ICP-OES | Acid mineralization of the sample in a microwave oven and analysis of the conductively induced plasma by means of a single quadrupole mass spectrometer, or optical emission spectrometer. (M1) |
| | | IC-CD | Sample extraction and analysis by ion chromatograph coupled to conductometric detector. (M2) |
| | Anions | IC-CD | Sample extraction and analysis by ion chromatograph coupled to conductometric detector. (M2) |
| Total RNA | Nucleosides | UHPLC-qToF | After extraction and digestion of RNA from the sample a reverse phase chromatography analysis was applied by UHPLC coupled to a quadrupole-time-of-flight mass spectrometer. (N) |

The results, that are summarised in the table below, show an appreciable composition variability of each batch and underline the impossibility to recapitulate the properties of the matrix as the sum of its single components. The work performed and reported herein (see cell based assay results) together with the data below, demonstrates that the biological effect elicited by product cannot be recapitulated by the sum of the effects elicited by the single molecular components but is the result of interconnections and interactions among the components: the matrix effect. This translates into the impossibility to formally define a structure-activity relationship (SAR) according to the principles canonically applied to APIs.

| Method | COMPOUNDS | 21E1640 (%) | 20B1955 (%) | 20I1279 (%) | 20J1770 (%) | 20B0596 (%) | 21E1640 (d %) | 20I1279 (d %) | 20J1770 (d %) | 20B0596 (d %) |
|---|---|---|---|---|---|---|---|---|---|---|
| G | NITROGEN-CONTAINING SUBSTANCES, Total | 5.1 | 5.1 | 5 | 4.7 | 0.76 | 0.00 | 1.96 | 7.84 | 85.10 |
| | FIBERS, Total | 5.4 | 2.3 | 1.5 | 1.7 | 1.8 | 134.78 | 34.78 | 26.09 | 22.26 |
| A2 | SOLUBLE FIBERS, Total | 5.4 | 2.3 | 1.5 | 1.1 | 1.5 | 134.78 | 34.78 | 52.17 | 34.78 |
| A3 | FRUCTOLIGO-SACCHARIDES, Total | <LdQ | <LdQ | <LdQ | 0.6 | 0.2880 | / | / | / | / |
| A1 | INSOLUBLE FIBERS, Total | <LdQ | <LdQ | <LdQ | <LdQ | <LdQ | / | / | / | / |
| B | MACRO-MOLECULES > 20000 (POLY-SACCHARIDES), Total | <LdQ | <LdQ | <LdQ | <LdQ | <LdQ | / | / | / | / |
| C | WATER, Total | 3.4 | 5.4 | 4 | 4.10 | 4.50 | 37.04 | 25.93 | 24.07 | 16.67 |
| | PHENOLS, Total | 4.57 | 3.45 | 3.20 | 3.33 | 2.97 | 32.30 | 7.37 | 3.48 | 13.95 |
| | FLAVONOIDS, Total | 1.80 | 1.49 | 1.49 | 1.74 | 1.18 | 20.48 | 0.47 | 16.39 | 20.81 |
| D1 | Rottlerin | <LdQ | <LdQ | <LdQ | <LdQ | / | / | / | / | / |
| D1 | Phloridzin | nq | nq | nq | / | / | / | / | / | / |
| | FLAVANONES, Total | 0.01 | 0.0052 | 0.0096 | nq | nq | 92.31 | 84.62 | / | / |
| D1 | Flavanomarein | 0.01 | 0.0052 | 0.0096 | nq | nq | 92.31 | 84.62 | / | / |
| | FLAVONES, Total | 0.0258 | 0.02 | 0.0297 | 0.023858 | 0.0134 | 29.00 | 48.50 | 19.29 | 33.00 |
| D1 | 3',4',5,5',6,7-Hexamethoxy-flavone | <LdQ | 0.0002 | 0.0002 | 0.000119 | 0.0002 | / | 0.00 | 40.55 | 5.52 |
| D1 | Diosmin | nd | <LdQ | <LdQ | <LdQ | / | / | / | / | / |
| D1 | Homoorientin | 0.009 | 0.0063 | 0.0128 | 0.003715 | 0.0037 | 42.86 | 103.17 | 41.03 | 41.65 |
| D1 | Isoschaftoside | 0.0008 | 0.001 | 0.0009 | 0.004852 | 0.0022 | 20.00 | 10.00 | 385.20 | 124.34 |
| D1 | Isovitexin | 0.0012 | 0.001 | 0.0011 | 0.000779 | 0.0006 | 20.00 | 10.00 | 22.10 | 40.89 |
| D1 | Linarin | nd | nd | nd | <LdQ | / | / | / | / | / |
| D1 | Luteolin-7-O-beta-D-glucoside (Cynaroside) | nd | nd | nd | <LdQ | / | / | / | / | / |
| D1 | Luteolin-7-O-glucuronide | nd | nd | nd | <LdQ | <LdQ | / | / | / | / |
| D1 | Nobiletin | <LdQ | <LdQ | <LdQ | <LdQ | <LdQ | / | / | / | / |
| D1 | Orientin | 0.0025 | 0.0026 | 0.0018 | nq | nq | 3.85 | 30.77 | / | / |
| D1 | Schaftoside | 0.0067 | 0.0044 | 0.0081 | 0.008796 | 0.0036 | 52.27 | 84.09 | 99.91 | 19.06 |
| D1 | Vicenin-2 | 0.0038 | 0.0032 | 0.0029 | 0.004069 | 0.0021 | 18.75 | 9.38 | 27.16 | 33.32 |
| D1 | Vitexin | 0.0018 | 0.0013 | 0.0019 | 0.001528 | 0.0010 | 38.46 | 46.15 | 17.55 | 25.67 |

-continued

| Method | COMPOUNDS | 21E1640 (%) | 20B1955 (%) | 20I1279 (%) | 20J1770 (%) | 20B0596 (%) | 21E1640 (d %) | 20I1279 (d %) | 20J1770 (d %) | 20B0596 (d %) |
|---|---|---|---|---|---|---|---|---|---|---|
| | FLAVONOLS, Total | 1.7619 | 1.4669 | 1.4458 | 1.707743 | 1.1682 | 20.11 | 1.44 | 16.42 | 20.36 |
| D1 | Isorhamnetin-3-O-glucoside | 0.0022 | 0.0018 | 0.002 | 0.001514 | 0.0016 | 22.22 | 11.11 | 15.92 | 11.28 |
| D1 | Isorhamnetin-3-O-rutinoside | <LdQ | <LdQ | <LdQ | <LdQ | / | / | / | / | / |
| D1 | Kaempferol | 0.0062 | 0.0136 | 0.0104 | 0.002918 | 0.0030 | 54.41 | 23.53 | 78.54 | 77.76 |
| D1 | Kaempferol-3-O-glucoside | 0.0342 | 0.1187 | 0.0743 | 0.032471 | 0.0729 | 71.19 | 37.41 | 72.64 | 38.56 |
| D1 | Kaempferol-3-O-glucuronide | 0.3409 | 0.2751 | 0.2855 | 0.618309 | 0.5180 | 23.92 | 3.78 | 124.76 | 88.31 |
| D1 | Kaempferol-3-O-rutinoside | 0.0076 | 0.0119 | 0.0092 | 0.00195 | 0.0035 | 36.13 | 22.69 | 83.61 | 70.69 |
| D1 | Quercetin | 0.0201 | 0.0352 | 0.0159 | 0.012575 | 0.0192 | 42.90 | 54.83 | 64.27 | 45.36 |
| D1 | Quercetin-3-O-glucopyranoside (Isoquercetin) | 0.0694 | 0.0871 | 0.0694 | 0.025885 | 0.0598 | 20.32 | 20.32 | 70.28 | 31.36 |
| D1 | Quercetin-3-O-glucuronide | 1.2456 | 0.8651 | 0.9198 | 0.985214 | 0.4558 | 43.98 | 6.32 | 13.88 | 47.31 |
| D1 | Rutin | 0.0357 | 0.0584 | 0.0593 | 0.026907 | 0.0313 | 38.87 | 1.54 | 53.93 | 46.34 |
| | ISOFLAVONES, Total | <LdQ | <LdQ | <LdQ | <LdQ | <LdQ | / | / | / | / |
| D1 | Genistin | <LdQ | <LdQ | <LdQ | <LdQ | <LdQ | / | / | / | / |
| | PHENOLIC ACIDS, Total | 0.0745 | 0.0707 | 0.0923 | 0.077983 | 0.1091 | 5.37 | 30.55 | 10.30 | 54.35 |
| D1 | Protocatechuic acid | 0.0745 | 0.0707 | 0.0923 | 0.077983 | 0.1091 | 5.37 | 30.55 | 10.30 | 54.35 |
| D1 | Vanillic acid | nd | nd | nd | <LdQ | / | / | / | / | / |
| | PHENYL-PROPANOIDS, Total | 2.682 | 1.872 | 1.606 | 1.490576 | 0.929 | 43.25 | 14.23 | 20.39 | 50.38 |
| | COUMARINS, Total | 0.0149 | 0.0168 | 0.0164 | 0.007515 | 0.0022 | 11.31 | 2.38 | 55.27 | 86.90 |
| D1 | Aesculin | 0.0051 | 0.0043 | 0.0112 | 0.006231 | 0.0047 | 18.60 | 160.47 | 44.90 | 8.63 |
| D1 | Esculetin | 0.0098 | 0.0125 | 0.0052 | 0.001284 | 0.0053 | 21.60 | 58.40 | 89.73 | 57.65 |
| D1 | Fraxin | <LdQ | <LdQ | <LdQ | / | <LdQ | / | / | / | / |
| | HYDROXY-CINNAMIC ACIDS, Total | 2.667 | 1.856 | 1.590 | 1.442046 | 0.9068 | 43.75 | 14.33 | 22.29 | 51.13 |
| D1 | 3,5-Dicaffeoylquinic acid | 1.043 | 0.5573 | 0.516 | 0.4833 | 0.2254 | 87.15 | 7.41 | 13.28 | 59.56 |
| D1 | 4,5-Dicaffeoylquinic acid | 0.1822 | 0.1601 | 0.1568 | 0.058033 | 0.0547 | 13.80 | 2.06 | 63.75 | 65.85 |
| D1 | Caffeic acid | 0.0219 | 0.0168 | 0.0274 | 0.008865 | 0.0089 | 30.36 | 63.10 | 47.23 | 47.04 |
| D2 | Caftaric acid | 0.2338 | 0.2825 | 0.2005 | 0.1949 | 0.2198 | 17.24 | 29.03 | 31.01 | 22.19 |
| D2 | Chicoric acid | 0.282 | 0.2948 | 0.17 | 0.1748 | 0.2142 | 4.34 | 42.33 | 40.71 | 27.34 |
| D2 | Chlorogenic acid | 0.8213 | 0.4702 | 0.4644 | 0.4276 | 0.2931 | 74.67 | 1.23 | 9.06 | 37.66 |

-continued

| Method | COMPOUNDS | 21E1640 (%) | 20B1955 (%) | 20I1279 (%) | 20J1770 (%) | 20B0596 (%) | 21E1640 (d %) | 20I1279 (d %) | 20J1770 (d %) | 20B0596 (d %) |
|---|---|---|---|---|---|---|---|---|---|---|
| D2 | Echinacoside | <LdQ | <LdQ | <LdQ | / | / | / | / | / | / |
| D1 | Ferulic acid | 0.0081 | 0.0047 | 0.0055 | 0.003602 | nq | 72.34 | 17.02 | 23.36 | / |
| D1 | Neochlorogenic acid | 0.0626 | 0.0658 | 0.0445 | 0.090946 | 0.0598 | 4.86 | 32.37 | 38.22 | 9.18 |
| D1 | Rosmarinic acid | 0.0082 | 0.0034 | 0.0026 | nq | / | 141.18 | 23.53 | / | / |
| D1 | Verbascoside | 0.0043 | <LdQ | 0.0019 | / | nq | / | / | / | / |
| | PHLORO-GLUCINOLS, Total | nq | nq | nq | <LdQ | / | / | / | / | / |
| D1 | Phloroglucinol carboxylic acid | nq | nq | nq | <LdQ | / | / | / | / | / |
| | SALICYLATES, Total | 0.0118 | 0.0162 | 0.0136 | 0.0145 | 0.006522 | 27.16 | 16.05 | 10.50 | 59.74 |
| D1 | Salicylic acid | 0.0118 | 0.0162 | 0.0136 | 0.0145 | 0.006522 | 27.16 | 16.05 | 10.50 | 59.74 |
| | TERPENES, Total | 13.63 | 15.80 | 16.59 | 14.92 | 14.93 | 13.74 | 5.02 | 5.57 | 5.49 |
| | MONO-TERPENES, Total | 0.000408 | 0.000329 | 0.00042 | 0.000305 | 0.0008 | 23.96 | 29.09 | 7.15 | 143.18 |
| | MONO-TERPENE ALCOHOLS, Total | 0.000355 | 0.00028 | 0.00037 | 0.000278 | 0.000309 | 26.59 | 32.76 | 0.95 | 10.17 |
| E3 | alpha-Terpineol | <LdQ | <LdQ | <LdQ | <LdQ | <LdQ | / | / | / | / |
| E3 | Carvacrol | 4.49E−05 | 5.08E−05 | 5.1E−05 | 2.61E−05 | 9.34E−05 | 11.67 | 0.85 | 48.61 | 83.83 |
| E3 | Eucalyptol | <LdQ | nd | nd | <LdQ | <LdQ | / | / | / | / |
| E3 | Linalool | 0.00031 | 0.00023 | 0.00032 | 0.000252 | 0.000216 | 35.06 | 39.82 | 9.59 | 6.13 |
| | MONO-TERPENE HYDRO-CARBONS, Total | 5.27E−05 | 4.85E−05 | 5.2E−05 | 2.77E−05 | <LdQ | 8.70 | 7.90 | 42.97 | / |
| E3 | 4-Cymene | 5.27E−05 | 4.85E−05 | 5.2E−05 | 2.77E−05 | <LdQ | 8.70 | 7.90 | 42.97 | / |
| E3 | alpha-Pinene | nd | nd | <LdQ | <LdQ | <LdQ | / | / | / | / |
| E3 | alpha-Terpinene | <LdQ | <LdQ | <LdQ | <LdQ | <LdQ | / | / | / | / |
| E3 | beta-Pinene | <LdQ | <LdQ | <LdQ | <LdQ | <LdQ | / | / | / | / |
| E3 | Camphene | <LdQ | <LdQ | <LdQ | <LdQ | <LdQ | / | / | / | / |
| E3 | gamma-Terpinene | <LdQ | <LdQ | <LdQ | <LdQ | <LdQ | / | / | / | / |
| E3 | Myrcene | <LdQ | <LdQ | <LdQ | <LdQ | <LdQ | / | / | / | / |
| E3 | Sabinene | <LdQ | nd | <LdQ | <LdQ | <LdQ | / | / | / | / |
| E3 | Terpinolene | <LdQ | <LdQ | <LdQ | <LdQ | <LdQ | / | / | / | / |
| | TRITERPENES, Total | 13.627 | 15.799 | 16.592 | 14.919 | 14.9314 | 13.74 | 5.02 | 5.57 | 5.49 |
| | PHYTO-STEROLS, Total | 0.001141 | 0.001289 | <LdQ | / | / | 11.45 | / | / | / |
| E4 | 24-Methylene-cholesterol | 0.000056 | <LdQ | <LdQ | / | / | / | / | / | / |

-continued

| Method | COMPOUNDS | 21E1640 (%) | 20B1955 (%) | 20I1279 (%) | 20J1770 (%) | 20B0596 (%) | 21E1640 (d %) | 20I1279 (d %) | 20J1770 (d %) | 20B0596 (d %) |
|---|---|---|---|---|---|---|---|---|---|---|
| E4 | 7-Dehydro-cholesterol | <LdQ | <LdQ | <LdQ | / | / | / | / | / | / |
| E4 | beta-Sitosterol | 0.000435 | 0.000578 | <LdQ | / | / | 24.65 | / | / | / |
| E4 | Brassicasterol | <LdQ | <LdQ | <LdQ | / | / | / | / | / | / |
| E4 | Campestanol | 0.000181 | 6.19E−05 | <LdQ | / | / | 192.73 | / | / | / |
| E4 | Campesterol | 0.000149 | 0.000125 | <LdQ | / | / | 19.35 | / | / | / |
| E4 | Cholesterol | 8.78E−05 | 0.000075 | <LdQ | / | / | 17.32 | / | / | / |
| E4 | Clerosterol | <LdQ | <LdQ | <LdQ | / | / | / | / | / | / |
| E4 | delta-5-Avenasterol | <LdQ | 7.1E−05 | <LdQ | / | / | / | / | / | / |
| E4 | delta-5,23-Stigmastadienol | <LdQ | <LdQ | <LdQ | / | / | / | / | / | / |
| E4 | delta-5,24-Stigmastadienol | <LdQ | <LdQ | <LdQ | / | / | / | / | / | / |
| E4 | delta-7-Avenasterol | <LdQ | <LdQ | <LdQ | / | / | / | / | / | / |
| E4 | delta-7-Campesterol | <LdQ | <LdQ | <LdQ | / | / | / | / | / | / |
| E4 | delta-7-Stigmastenol | 0.000074 | 0.000107 | <LdQ | / | / | 30.79 | / | / | / |
| E4 | delta-7,9(11)-Stigmastadienol | <LdQ | <LdQ | <LdQ | / | / | / | / | / | / |
| E4 | Sitostanol | 0.000041 | 9.55E−05 | <LdQ | / | / | 57.01 | / | / | / |
| E4 | Stigmasterol | 0.000116 | 0.000175 | <LdQ | / | / | 33.72 | / | / | / |
| | SAPOGENINS, Total | 0.0091 | 0.0154 | 0.0176 | <LdQ | 0.0054 | 40.91 | 14.29 | / | 64.94 |
| E1 | Asiatic acid | 0.001 | 0.0033 | 0.0024 | <LdQ | <LdQ | 69.70 | 27.27 | / | / |
| E1 | Madecassic acid | 0.0081 | 0.0121 | 0.0152 | <LdQ | 0.005364 | 33.06 | 25.62 | / | 55.67 |
| | SAPONINS, Total | 13.617 | 15.782 | 16.574 | 14.919 | 14.926 | 13.72 | 5.02 | 5.47 | 5.42 |
| E2 | Asiaticoside | 5.526 | 7.121 | 6.935 | 6.143 | 6.801 | 22.40 | 2.61 | 13.73 | 4.49 |
| E2 | Madecassoside | 8.091 | 8.661 | 9.639 | 8.776 | 8.125 | 6.58 | 11.29 | 1.33 | 6.19 |
| | SESQUITER-PENES Total | <LdQ | nd | <LdQ | <LdQ | nd | / | / | / | / |
| E3 | Farnesol | <LdQ | nd | <LdQ | / | / | / | / | / | / |
| | ORGANIC ACIDS, Total | 10.37 | 14.48 | 9.94 | 9.03 | 15.07 | 28.38 | 31.31 | 37.66 | 4.07 |
| | MONO-CARBOXYLIC ACIDS, Total | <LdQ | 2.03 | <LdQ | 1.431 | 1.627 | / | / | 29.51 | 19.85 |
| F | Acetic acid | <LdQ | 1.07 | <LdQ | 0.151 | 0.177 | / | / | 85.89 | 83.46 |
| F | Formic acid | <LdQ | <LdQ | <LdQ | <LdQ | <LoQ | / | / | / | / |
| F | Lactic acid | <LdQ | 0.96 | <LdQ | 1.28 | 1.45 | / | / | 33.33 | 51.04 |
| | DI-CARBOXYLIC ACIDS, Total | 8.2088 | 10.4075 | 7.6748 | 4.7048 | 10.05 | 21.13 | 26.26 | 54.79 | 3.44 |

-continued

| Method | COMPOUNDS | 21E1640 (%) | 20B1955 (%) | 20I1279 (%) | 20J1770 (%) | 20B0596 (%) | 21E1640 (d %) | 20I1279 (d %) | 20J1770 (d %) | 20B0596 (d %) |
|---|---|---|---|---|---|---|---|---|---|---|
| F | Fumaric acid | 0.067 | 0.0446 | 0.067 | 0.13 | 0.136 | 50.22 | 50.22 | 191.48 | 204.93 |
| F | Malic acid | 8.08 | 2.2 | 7.54 | 4.55 | 5.75 | 267.27 | 242.73 | 106.82 | 161.36 |
| F | Succinic acid | <LdQ | 8.14 | <LdQ | <LdQ | 4.13 | / | / | / | 49.26 |
| F | Tartaric acid | 0.0618 | 0.0229 | 0.0678 | 0.0248 | 0.034 | 169.87 | 196.07 | 8.30 | 48.47 |
| | TRI-CARBOXYLIC ACIDS, Total | 2.16 | 2.04 | 2.27 | 2.89 | 3.39 | 5.88 | 11.27 | 41.67 | 66.18 |
| F | Citric acid | 2.16 | 2.04 | 2.27 | 2.89 | 3.39 | 5.88 | 11.27 | 41.67 | 66.18 |
| | SUGARS AND DERIVATIVES, Total | 11.42 | 1.85 | 10.78 | 13.34 | 7.46 | 516.13 | 481.66 | 619.61 | 302.37 |
| | MONO-SACCHARIDES, Total | 11.423 | 1.854 | 10.784 | 10.0247 | 7.16 | 516.13 | 481.66 | 440.71 | 286.19 |
| I | Fructose | 5.707 | 1.854 | 5.38 | 6.20591 | 4.5300 | 207.82 | 190.18 | 234.73 | 144.34 |
| I | Galactose | 1.369 | <LdQ | 1.315 | 1.30558 | 1.1000 | / | / | / | / |
| I | Glucose | 4.347 | <LdQ | 4.089 | 2.51321 | 1.2900 | / | / | / | |
| | DISAC-CHARIDES, Total | <Ldq | <Ldq | <Ldq | 3.31694 | 0.30 | / | / | / | / |
| I | Lactose | <Ldq | <Ldq | <Ldq | <LdQ | / | / | / | / | / |
| I | Maltose | <Ldq | <Ldq | <Ldq | 1.54 | / | / | / | / | / |
| I | Sucrose | nq | nq | nq | 1.77694 | 0.30 | / | / | / | / |
| | LIPIDS, Total | 0.200 | 0.170 | 0.190 | 4.03E−05 | 5.88E−05 | 17.64 | 11.76 | 99.98 | 99.97 |
| | FATTY ACIDS, Total | 0.2 | 0.17 | 0.19 | <LdQ | 5.88E−05 | 17.65 | 11.76 | / | 99.97 |
| H4 | Decanoic acid | nd | nd | 0.01 | / | / | / | / | / | / |
| H4 | Dodecanoic acid | 0.02 | nd | nd | / | / | / | / | / | / |
| H4 | Linoleic acid | nd | nd | nd | / | / | / | / | / | / |
| H4 | Linolenic acid | nd | nd | nd | / | / | / | / | / | / |
| H4 | Myristic acid | nd | nd | nd | / | / | / | / | / | / |
| H4 | Octanoic acid | nd | nd | 0.01 | / | / | / | / | / | / |
| H4 | Oleic acid | nd | nd | nd | / | / | / | / | | / |
| H4 | Palmitic acid | 0.1 | 0.1 | 0.09 | / | / | 0.00 | 10.00 | / | / |
| H3 | Propionic acid | <LdQ | <LdQ | <LdQ | / | / | / | / | / | / |
| H4 | Stearic acid | 0.08 | 0.07 | 0.08 | / | / | 14.29 | 14.29 | / | / |
| | FATTY ACID DERIVATIVES, Total | 9.38E−05 | 9.37E−05 | 9.5E−05 | 4.03E−05 | 5.88E−05 | 0.09 | 1.20 | 57.05 | 37.24 |
| | FATTY ACID ESTERS, Total | 9.38E−05 | 9.37E−05 | 9.5E−05 | 4.03E−05 | 5.88E−05 | 0.09 | 1.20 | 57.05 | 37.24 |
| H2 | Ethyl palmitate | 9.38E−05 | 9.37E−05 | 9.5E−05 | 4.03E−05 | 5.88E−05 | 0.09 | 1.20 | 57.05 | 37.24 |
| | OTHER ORGANIC COMPOUNDS, Total | 0.00069 | 0.00048 | 0.00069 | 0.00064 | 0.000361 | 44.12 | 44.78 | 33.41 | 24.64 |
| | AROMATIC COMPOUNDS, Total | 0.000691 | 0.00048 | 0.00069 | 0.00064 | 0.000361 | 44.12 | 44.78 | 33.41 | 24.64 |

-continued

| Method | COMPOUNDS | 21E1640 (%) | 20B1955 (%) | 20I1279 (%) | 20J1770 (%) | 20B0596 (%) | 21E1640 (d %) | 20I1279 (d %) | 20J1770 (d %) | 20B0596 (d %) |
|---|---|---|---|---|---|---|---|---|---|---|
| | AROMATIC ALCOHOLS, Total | 0.000665 | / | 0.00067 | 0.000622 | 0.000361 | / | / | / | / |
| L | para,alpha,alpha-Trimethylbenzyl alcohol | 0.000665 | 0.000466 | 0.00067 | 0.000622 | 0.000361 | 42.67 | 44.25 | −33.35 | 22.46 |
| L | Benzaldehyde | <LdQ | <LdQ | <LdQ | <LdQ | <LdQ | / | / | / | / |
| | STYRENES, Total | 2.62E−05 | 1.35E−05 | 2.2E−05 | 1.82E−05 | <LdQ | 94.07 | 62.94 | 35.28 | / |
| L | Dimethylstyrene | 2.62E−05 | 1.35E−05 | 2.2E−05 | 1.82E−05 | <LdQ | 94.07 | 62.94 | 35.28 | / |
| | INORGANIC COMPOUNDS, Total | 21.85 | 26.21 | 21.45 | 22.98 | 27.44 | 16.63 | 18.18 | 12.34 | 4.68 |
| | ANIONS, Total | 4.6313 | 6.34 | 4.4114 | 5.463733 | 5.53 | 26.95 | 30.42 | 13.82 | 12.78 |
| M2 | Nitrate | 0.0013 | <LdQ | 0.0014 | 0.092379 | <IdQ | / | / | / | / |
| M2 | Nitrite | <LdQ | <LdQ | <LdQ | <LdQ | <IdQ | / | / | / | / |
| M2 | Phosphate | 1.63 | 1.74 | 1.55 | 1.529767 | 1.4700 | 6.32 | 10.92 | 12.08 | 15.52 |
| M2 | Sulfate | 3 | 4.6 | 2.86 | 3.841587 | 4.0600 | 34.78 | 37.83 | 16.49 | 11.74 |
| | MACRO-ELEMENTS, Total | 17.05 | 19.66 | 16.87 | 17.32551 | 21.9985 | 13.28 | 14.18 | 11.88 | 11.89 |
| M1 | Calcium | 1.745388 | 2.544027 | 1.75523 | 1.847967 | 2.8998 | 31.39 | 31.01 | 27.36 | 13.98 |
| M2 | Chloride | 4.67 | 5.32 | 4.36 | 5.496178 | 4.8700 | 12.22 | 18.05 | 3.31 | 8.46 |
| M1 | Magnesium | 1.270564 | 1.533499 | 1.25715 | 1.233837 | 1.6827 | 17.15 | 18.02 | 19.54 | 9.73 |
| M1 | Phosphorus | 0.624007 | 0.619255 | 0.60815 | 0.579524 | 0.7223 | 0.77 | 1.79 | 6.42 | 16.64 |
| M1 | Potassium | 5.728856 | 6.134733 | 5.80766 | 5.657116 | 7.6743 | 6.62 | 5.33 | 7.79 | 25.10 |
| M1 | Sodium | 2.326488 | 2.741546 | 2.40561 | 2.510884 | 3.8194 | 15.14 | 12.25 | 8.41 | 39.31 |
| M1 | Sulfur | 0.683772 | 0.767168 | 0.6784 | 1.56 | <LdQ | 10.87 | 11.57 | 103.35 | / |
| | MICRO-ELEMENTS, Total | 0.137432 | 0.165006 | 0.12715 | 0.134181 | 0.1918 | 16.71 | 22.94 | 18.68 | 16.24 |
| M1 | Chromium | 3.09E−05 | 0.000102 | 0.00011 | 8.77E−05 | 0.0007 | 69.77 | 9.86 | 14.21 | 567.60 |
| M1 | Cobalt | 0.000127 | 0.000122 | 0.00013 | 0.000149 | 0.0001 | 4.08 | 8.87 | 22.19 | 7.45 |
| M1 | Copper | 0.000718 | 0.000226 | 0.00091 | 0.000945 | 0.0009 | 217.47 | 303.07 | 317.91 | 287.93 |
| M2 | Fluoride | NQ | NQ | NQ | <Ldq | nq | / | / | / | / |
| M1 | Iron | 0.000372 | 0.000777 | 0.00326 | 0.002209 | 0.0027 | 52.15 | 319.33 | 184.10 | 243.53 |
| M1 | Manganese | 0.128456 | 0.156247 | 0.11479 | 0.121585 | 0.1722 | 17.79 | 26.53 | 22.18 | 10.20 |
| M1 | Molybdenum | <LdQ | <LdQ | <LdQ | <LdQ | <LdQ | / | / | / | / |
| M1 | Nickel | 0.000873 | 0.000727 | 0.00106 | 0.00111 | 0.0008 | 20.11 | 45.89 | 52.65 | 3.32 |
| M1 | Selenium | <LdQ | <LdQ | <LdQ | <LdQ | <LdQ | / | 1 | / | / |
| M1 | Tin | <LdQ | <LdQ | <LdQ | <LdQ | <LdQ | / | / | / | / |
| M1 | Vanadium | <LdQ | <LdQ | <LdQ | <LdQ | <LdQ | / | / | / | / |
| M1 | Zinc | 0.006855 | 0.006804 | 0.00688 | 0.008096 | 0.0145 | 0.75 | 1.09 | 18.99 | 112.71 |
| | OTHER ELEMENTS, Total | 0.035826 | 0.049164 | 0.03758 | 0.056604 | 0.0508 | 27.13 | 23.57 | 15.13 | 3.33 |
| M1 | Aluminum | 0.00085 | 0.001453 | 0.00176 | <LdQ | 0.0021 | 41.48 | 20.92 | / | 45.49 |
| M1 | Antimony | <LdQ | <LdQ | <LdQ | <LdQ | <LdQ | / | / | / | / |
| M1 | Arsenic | <LdQ | <LdQ | <LdQ | <LdQ | <LdQ | / | / | / | / |
| M1 | Barium | 0.00455 | 0.005308 | 0.00493 | 0.005361 | 0.0055 | 14.29 | 7.16 | 0.98 | 4.28 |

-continued

| Method | COMPOUNDS | 21E1640 (%) | 20B1955 (%) | 20I1279 (%) | 20J1770 (%) | 20B0596 (%) | 21E1640 (d %) | 20I1279 (d %) | 20J1770 (d %) | 20B0596 (d %) |
|---|---|---|---|---|---|---|---|---|---|---|
| M1 | Boron | 0.002366 | 0.002735 | 0.00244 | 0.002466 | 0.0028 | 13.49 | 10.73 | 9.84 | 3.87 |
| M3 | Bromide | 0.00019 | 0.00027 | 0.00018 | 0.016442 | / | 29.63 | 33.33 | 5989.72 | / |
| M1 | Cadmium | <LdQ | <LdQ | <LdQ | <LdQ | <LdQ | / | / | / | / |
| M1 | Gadolinium | <LdQ | <LdQ | <LdQ | <LdQ | <LdQ | / | / | / | / |
| M1 | Gallium | <LdQ | <LdQ | <LdQ | <LdQ | <LdQ | / | / | / | / |
| M1 | Gold | <LdQ | <LdQ | <LdQ | <LdQ | <LdQ | / | / | / | / |
| M1 | Iridium | <LdQ | <LdQ | <LdQ | <LdQ | <LdQ | / | / | / | / |
| M1 | Lead | <LdQ | <LdQ | <LdQ | <LdQ | nd | / | / | / | / |
| M1 | Lithium | 2.79E−05 | 4.26E−05 | 3.6E−05 | 3.27E−05 | 0.0000 | 34.59 | 16.02 | 23.32 | 12.05 |
| M1 | Lutetium | <LdQ | <LdQ | <LdQ | <LdQ | <LdQ | / | / | / | / |
| M1 | Mercury | <LdQ | <LdQ | <LdQ | <LdQ | <LdQ | / | / | / | / |
| M1 | Rubidium | 0.016844 | 0.022168 | 0.01703 | 0.019779 | 0.0230 | 24.02 | 23.20 | 10.78 | 3.70 |
| M1 | Silver | <LdQ | <LdQ | <LdQ | <LdQ | <LdQ | / | / | / | / |
| M1 | Strontium | 0.008375 | 0.013771 | 0.00873 | 0.01 | 0.0125 | 39.19 | 36.62 | 27.38 | 9.23 |
| M1 | Tellurium | <LdQ | <LdQ | <LdQ | <LdQ | <LdQ | / | / | / | / |
| M1 | Thallium | <LdQ | <LdQ | <LdQ | <LdQ | <LdQ | / | / | / | / |
| M1 | Thorium | <LdQ | <LdQ | <LdQ | <LdQ | <LdQ | / | / | / | / |
| M1 | Titanium | 0.002622 | 0.003414 | 0.00248 | 0.002523 | 0.0047 | 23.20 | 27.35 | 26.09 | 39.02 |
| M1 | Tungsten | <LdQ | <LdQ | <LdQ | <LdQ | <LdQ | / | / | / | / |
| M1 | Uranium | <LdQ | <LdQ | <LdQ | <LdQ | <LdQ | / | / | / | / |
| M1 | Ytterbium | <LdQ | <LdQ | <LdQ | <LdQ | <LdQ | / | / | / | / |

Note 1.
Gray boxes indicate chemical macro classes.
Note 2.
% = compound concentration expressed as percentage.
Note 3.
(d %) = percentage deviation: (|Gold (%)-Test (%)|/(Gold (%)) × 100).
Note 4.
The term "Total" refers to the sum of the value of the various compounds which forms the corresponding group.
Note 5.
<LoQ = below the limit of quantification.
Note 6.
nd = compound not detected
Note 7.
nq = compound not quantifiable.
Note 8.
/ = compound not reported.

The results show that there are more or less marked quantitative fluctuations of the individual chemical classes in the five batches of co-extract. These fluctuations, if taken as the reference parameter, would lead to an a priori view that these batches have different biological activity and to the rejection of the batches that are not comparable to the gold standard, if the criteria applied were those valid for an API acting via the keylock paradigm thanks to the presence of an evident SAR. The analysis here reported argues the fact that, despite the biological activity is maintained across all of the different batches assessed, none of the single molecular components identified would respect the criteria set for a single API, thus demonstrating that the matrix should not be considered as a compilation of APIs.

As seen above, the biological activity is preserved in every batch.

Thus, FIG. 5 shows that it is not representative and therefore not correct to entrust the estimation of the reproducibility of the activity profile of a complex matrix purely on the quantitative analysis of the individual constituents. In fact, given the very nature of a complex matrix, quali quantitatively different chemical profiles, which, on a chemical standpoint should be considered different, evoke instead, in biological systems, the same reaction relevant for the intended use. This should not be a surprising observation but another demonstration that biological activity of a complex matrix cannot be traced back to the sum of the activity of each single molecule within the matrix itself (i.e. the chemical standpoint). Therefore, the activity of the matrix does not exclusively depend on the identity and on the quantity of the molecules which constitute it.

This also highlights the fact that there are both structural and functional redundancy mechanisms that give the matrix particular resilience, i.e., as shown above, the ability to mediate the same activity against different quali quantitative compositions. In other words, the study of a matrix from an exclusively molecular point of view is not correct because the identity of its individual components do not reflect its features. This confirms the need for methods capable of describing the intrinsic characteristics of the matrix rather than looking exclusively at its molecular components. Those methods, as the one provided in the present invention, should monitor the preservation of those parameters on which the maintenance of biological activity is really dependent.

3.2. Near Infrared Spectroscopy (NIR)

3.2.1. Introduction

To create the control chart and provide the NIR acceptability cut-offs, four batches (comprising the gold standard) of Arté GX made on a prototype and industrial scale selected as positive batches according to the method of the invention, steps i) to iv), were analysed and formed the library of good quality samples (training set). The batches used to build the training set were selected after passing the conformity test performed through the biological assay of the invention (see also examples above).

Once the library was defined, a batch of Arté GX DEGR 21E1640 selected as negative batch according to the method of the invention, steps i) to iv), was also analysed. The five batches were used to set the NIR acceptability parameters.

Once the acceptability parameters were defined, two poor formulative qualities as defined above (R19L4299 and R19L4298) as well as an unknown Arté GX batch (21E1640) as test samples were analysed using the same operating methods. Following the result obtained after analysis with conformity tests, the test samples are confirmed as being of good quality or not depending on whether they have passed the conformity test performed via a biological assay in order to confirm or, possibly, modify the acceptability criteria identified by the control card.

The aim of this study was to build a control map of NIR spectra, defined a priori through evaluation of conformity in biological activity of the batches that are part of it, as a fingerprint to be used to discriminate valid conformity batches of Arté GX from samples of poor biological and/or formulation quality.

Below is the list of the four batches used for the creation of the NIR library and the list of samples analysed as tests:

4 batches Arte GX for the construction of the library (Tab. 1) freeze dried 1 poor quality batch of Arté GX (poor biological activity quality)

1 batch of Arté GX as library test (Tab. 2) freeze dried 2 poor formulative qualities (Tab2)

TABLE 1

(Training set).

| Product | Batch |
|---|---|
| Arté GX Gold Standard | 20B1955 |
| Arté GX | 20I1279 |
| Arté GX | 20J1770 |
| Arté GX | 20B0596 |
| Arté GX | DEGR 21E1640 |

TABLE 2

(Test set).

| Product | Batch |
|---|---|
| Arté GX | 21E1640 |
| Water extract Centella Asiatica leaves | R19L4299 |
| Water extract Echinacea Purpurea leaves | R19L4298 |

3.2.2. Instruments

Bruker NIR spectrometers, model MPA (Multi-Purpose Analyzer):

Resolution: 16 cm−1

Wavenumber Reproducibility: Better than 0.04 cm−1

Wavenumber Accuracy: Better than 0.1 cm−1

Photometric Accuracy: 0.1% T

Wavenumber range: from 4000 to 12500 cm−1

Background scans: 64

Scans for sample acquisition: 64

3.3. Statistics Tests

Conformity Test (Compliance Testing)

Compliance testing is a simple method for testing deviations of measured NIR spectra within certain limits. To set these limits (acceptability cut-off), samples of good and bad quality belong to at least one batch or production cycle of the final product to be identified as reference spectra are needed that. According to the present invention, the reference samples are identified through a biological assay deemed appropriate (cell-based assay) (steps i) to iv) of the method of the invention) and are studied via NIR, in order to assess the minimum range of specifications such as to include the batches themselves. According to the invention, this range is imposed as acceptable in order to recognize whether a batch of unknown conformity is compliant or not. The NIR spectra of these samples reflect the different variations of the sample capable of achieving compliant and non-compliant performance in terms of biological activity and form a confidence band in the spectral range. In order to pass the NIR conformity test, the spectrum of a new sample must fall within this confidence band. First, the mean and standard deviation of the absorbance values for each wavelength (i) has to be calculated. The mean value plus/minus the standard deviation determines the confidence band within the spectral range and defines what amount of variation over each spectral wavelength is acceptable for the product analysed.

Secondly, it is necessary to check whether the spectrum of a sample to be tested falls within the confidence band defined in the spectral range. The difference between this sample and the average of the reference samples is calculated at each wavelength (i). This absolute deviation is then weighted by the corresponding standard deviation "s" on the respective wavelength, which results in a relative deviation called the Conformity Index (CI).

$$CI = (A_{reference,i} - A_{sample,i})/s_{reference,i}$$

$A_{reference,\ i}$=average absorbance at a given wavelength(i) of the reference (average spectrum)

$A_{sample,\ i}$=absorbance at a given wavelength(i) of the test sample $s_{reference,\ i}$=standard deviation at a given wavelength(i) of the reference (average spectrum)

In conformity tests another parameter can be used to evaluate the tests against the reference library applying the limit of the CI.

This parameter called Sum2 is represented by:

$$\text{Sum2} = (\text{Sum of All } CIs > CI \text{ limit} - CI \text{ limit})/ (\text{Sum of the number of points in the spectrum with } CI > CI \text{ limit})$$

Selecting the appropriate parameter in a conformity test depends on the user-specific control problem that can be easily addressed by the skilled person, in the case of products comprising or consisting of one or more natural matrix, i.e. extremely heterogeneous samples, Sum 2 is a suitable parameter.

Hence, in the present case, Sum2 parameter was selected for determining the acceptability cut-off of the conformity test.

3.3.1 Preparation of the Sample

Each sample was transferred to the sample holder suitable for the NIR analysis of inhomogeneous solids. Before the analysis, it was checked that the bottom of the sample holder was completely covered.

3.3.2 Sample Acquisition

The NIR spectra were acquired in reflection mode using a rotating sample holder suitable for the analysis of samples such as inhomogeneous solids, as well as powders, in order to ensure high reproducibility of the data.

Quality Control and background subtraction was performed before each acquisition. The samples, also reported in the previous tables (Tab. 1 and Tab 2), were prepared as described above and analysed at NIR.

3.3.3. Data Pre-Processing

Pre-processing is a mathematical manipulation to extrapolate spectral features and reduce sources of variability.

For the development of the reprocessing method, the pre-processing method involving the use of SNV normalization was selected as and the region of the spectrum from 4200 to 9000 cm–$^{1}$ was selected as the region of the spectrum of greatest relevance for the model.

The OPUS Software (Opus 8.5, Bruker) was used for carrying out the conformity test. By applying the pre-processing method the following parameters in the OPUS Conformity Index method were set:

a) Pre-processing: SNV;

b) Regions: From 4200 to 9000 cm-1;

c) Conformity Test parameters: Max Conformity Index Value; Sum2

3.3.4. Data Acquisition

Four batches indicated in Tab I/1 as well as the batches in tab I/2 were analysed. The four batches if Table I/1 above were used as reference spectra in the creation of the Conformity Index (CI) as they had the desired biological activity.

SNV normalization pre-processing was carried out and the region from 4200 to 9000 cm$^{-1}$ was selected as the region for data reprocessing. The CI MAX threshold and Sum 2 values of the batches of the card are shown below:

CIMAX Experimental Assay (Interval Based on the Biological Data (Steps i) to iv) of the Method of the Invention

| Batch type | Batch ID- | Cell-based assay | CI Max | Sum 2 |
|---|---|---|---|---|
| Reference | 20B1955 | GOLD STANDARD, COMPLIANT | 1.5 | 0.0 |
| Reference | 20I1279 | COMPLIANT | 1.5 | 0.0 |
| Reference | 20J1770 | COMPLIANT | 1.5 | 0.0 |
| Reference | 20B0596 | COMPLIANT | 1.3 | 0.0 |

(NIR Spectra in FIG. 6*a*)

As reported above, the Max Conformity Index Value is assigned based on the maximum CI MAX value defined by the training consisting of compliant (positive) samples according to the cell-based assay. From the first data (reported above), the CI limit was set to 1.5, this value was hence used to calculate the Sum 2 of the training set and of the test set.

In order to define the conformity limit of Sum 2, the negative batch (i.e. non compliant with the biological data (cell based assay) according to steps i) to iv) of the method of the invention) DEST 21E160 was tested against the control chart. The table below shows the results in terms of CI and Sum 2 for each batch.

| Batch type | Batch ID- | Formulative conformity | Cell-based assay | CI Max | Sum 2 |
|---|---|---|---|---|---|
| Reference | 20B1955 | COMPLIANT | COMPLIANT | 1.5 | 0.0 |
| Reference | 20I1279 | COMPLIANT | COMPLIANT | 1.5 | 0.0 |
| Reference | 20J1770 | COMPLIANT | COMPLIANT | 1.5 | 0.0 |
| Reference | 20B0596 | COMPLIANT | COMPLIANT | 1.3 | 0.0 |
| Reference | DEG 21E1640 | COMPLIANT | NOT COMPLIANT | 5.8 | 1.3 |

(NIR Average Spectrum of Compliant Batches Plus NIR Spectrum of Non-Compliant Batch FIG. 6*b*)

Based on the Sum 2 values of batch DEG 21E1640 and its non compliance with the cell based assay, the threshold Sum 2 value in order to define a batch as not compliant is hence set as ≤1.2. Once this acceptability cut-off was set following the method of the invention, a new unknown batch of Arte GX was and to known formulative non compliant batches were tested to verify the reliability of the method of the invention and its suitability for a process of quality control according to the description and to the claims.

Results

| Sample type | Batch | Formulative compliance | Cell-based assay | CI Max | Sum 2 (≤1.2) | Expected | Result |
|---|---|---|---|---|---|---|---|
| Reference | 20B1955 | COMPLIANT | COMPLIANT | 1.5 | 0.0 | COMPLIANT | COMPLIANT |
| Reference | 20I1279 | COMPLIANT | COMPLIANT | 1.5 | 0.0 | COMPLIANT | COMPLIANT |
| Reference | 20J1770 | COMPLIANT | COMPLIANT | 1.5 | 0.0 | COMPLIANT | COMPLIANT |
| Reference | 20B0596 | COMPLIANT | COMPLIANT | 1.3 | 0.0 | COMPLIANT | COMPLIANT |
| Reference | DEST 21E1640 | COMPLIANT | NOT COMPLIANT | 5.8 | 1.3 | NOT COMPLIANT | NOT COMPLIANT |
| Test | 21E1640 | COMPLIANT | Not assessed | 3.6 | 0.6 | UNKNOWN | COMPLIANT |
| Test | R19L4299 | NON COMPLIANT | Not assessed | 5.9 | 1.6 | NOT COMPLIANT | NOT COMPLIANT |
| Test | R19L4298 | NON COMPLIANT | Not assessed | 49.4 | 8.1 | NOT COMPLIANT | NOT COMPLIANT |

Therefore, according to the NIR assay with the acceptability cut-off assessed with the method of the invention, batch 21E1640 resulted compliant according to the validation process of the invention.

In order to confirm the validity of the validation process of the invention, the modulation of the biological functions identified for the product Arté GX described above was carried out also for batch 21E1640 and the product resulted compliant with the reference Z-scores according to steps ii) to iv) of the method of the invention. Hence, processes and methods have been identified that allow defining the acceptability criteria of a product comprising or consisting of one or more natural matrix on the basis of the conservation of a number of selected biological activities and regardless of the notion of its composition at the molecular level.

4. Radical Scavenger Activity

As additional control of the validity of the method and process of the invention, all the Arté GX batches above were also tested for their radical scavenger activity as this activity is known to have a notable promoting effect in osteogenesis. FIG. 12 summarises the hallmark and biological function related to this marker.

4.1. Assay Method

The assay involves the use of Human fibroblast (HuDe) cell line as a model to test the ability of products to have an antioxidant activity based on a scavenger activity. Five different batches of Arte GX were tested at the concentration of 1.4 mg/ml, calculated by applying the dilution factor of 2.8 reflecting product dilution in synovial fluid in an in vivo scenario.

The ROS scavenger activity test is based on the use of the reactive oxygen species (ROS) generator AAPH (2,2'-azobis-2-methyl-propanimidamide, dihydrochloride) which can simulate the appearance of exogenous pro-oxidant damage and thereby induces production of endogenous ROS. Fluorescent probe 6-carboxy-2',7'-dichlorodihydrofluorescein diacetate (H2DCFDA, Life Technologies) was used as indicator of the presence of ROS in cells. The fluorescence emission of H2DCFDA was measured at regular time intervals (every 10 minutes for a total of 90 minutes) with a fluorometer (Varioskan Lux, Thermo-Scientific) and quantitatively correlated to the production of free radicals in cells. In order to account for cell number at the end of the assay, all of the calculated fluorescence values are normalized with respect to relevant cell viability measured by MTT (tetrazolium salt, [3-(4,5-dimethylthiazol-2yl)-2,5-diphenyltetrazolium bromide, Sigma Aldrich) assay performed according to the manufacturer's instructions. The degree of protection from the generation of ROS provided by the tested products is compared to those obtained by protecting cells with ascorbic acid (considered as benchmark of antioxidant molecule). The results are shown as comparison of integrated area under fluorescence versus time curve (AUC) calculated versus AAPH (considered as 100% of ROS production).

4.2. Results

FIG. 7 shows equivalent radical scavenger activity of all five batches of Arté GX. All batches show an equivalently highly significant protective effect on fibroblasts.

The above discussed data further qualify the five batches as equivalent in terms of induction of the same biological effect, due to influence on gene expression as well as to radical scavenging activity.

The percentage (Z-score) was calculated as in FIG. 12.

All the batches were compliant with the Z-score values identified for the gold standard and therefore the NIR cut-off calculated as above confirmed the suitability of the methods and process of the invention also using different markers for monitoring the modulation of the selected biological function/s.

4. Isotopic Abundance

4.1 Introduction

The analysis of isotopic abundance is a way to describe matter from an atomic point of view. The isotopic distribution characterizing the starting materials may be influenced by phenomena of different nature which in turn may lead to significant variations in the final products [ISPRA, Quaderni—Laboratorio 2/2018. ISBN 978-88-448-0873-0]. The isotopic composition of a sample is equal to the ratio between the abundance of the heavy and light isotopic forms (example the relationship 13C/12C) and is expressed as a deviation, in parts per thousand, from an internationally identified standard reference material. A positive value of δ indicates that the heavy isotope is enriched in the sample compared to the standard, while a negative value indicates that the heavy isotope in the sample is impoverished.

A marked difference in isotopic abundance ratios of a sample compared to samples known to be of good quality can account for different intra- and intermolecular interactions between the phytochemical classes that make up the matrix regardless of the quantitative profile of the individual species and the different chemical reactivity kinetics. In the first case this phenomenon is defined as geometric isotope effect (GIE) and is due in particular to hydrogen binding. In fact, the length of the hydrogen bond with oxygen is smaller than that between deuterium and oxygen. This may involve a different structural rearrangement of both intra- and inter-molecular structures.

Isotope abundance also changes the kinetics of reactions, known as Kinetic isotope effect (KIE), which can be either primary or secondary, depending on whether the isotope changes the reaction making it faster or slower than the process of interest. It is therefore clear that the KIE establishes a link between a given isotopic abundance of a material and its ability to interact in a reproducible manner with biological systems. It therefore seems plausible that the analysis of isotopic abundance is a possible tool for monitoring the conformity of the product from a physical-chemical and potentially biological point of view.

In a batch, the presence of alterations in the isotopic abundance ratios may indicate adulteration, poor quality of the product and, when samples representing different intermediates along the production process are considered, possibly a general loss of its desirable native conformation.

In this context, the acquisition of several good-quality batches of the product, together with established conformity verification techniques such as NIR, may lead to the generation of a reference library where individual batches can be evaluated and isotopic reproducibility verified within established ranges.

In addition, the 14C activity assessment can define the system as 100% natural. This is because the 14C is an unstable isotope (half-life of 5730 years) and, therefore, tends to accumulate in living material while petroleum derivatives have a very low presence/absence of this unstable carbon isotope.

4.1.1. Results and Discussion

The analysis of isotopic abundance was carried out on the five batches included in the development and validation of the NIR method and thus constituting good quality batches (20B0596, 20B1955, 2011279, 20J1770, 21E1640), batches 20B0596, 20B1955 were prepared from different batches of starting materials with respect to batches 2011279, 20J1770, 21E1640.

The samples were sent to the Chelab (Tentamus Company) laboratory and tested for stable isotopes as follows:

δ18O: Method IRMS, UNIT % % V-SMOW.

δ13C: Method QMA-M-01, EA-IRMS, UNIT % % V-PDB. C14-activity was also tested:

14C-activity: Method ISO-16620-2; 2015 (AMS), UNIT % modern carbon (pMC).

The results were as follows.

δ ratio of the main isotopes of the co-extract *Centella-Echinacea*.

| Arté GX Batch | δ18O | δ13C | 14C-activity (% modern carbon Pmc) |
|---|---|---|---|
| 20B0596 | 22.6 | −25.54 | 102.35 |
| 20I1279 | 20.3 | −28.64 | 102.53 |
| 20B1955 | 22.3 | −28.83 | 102.28 |
| 20J1770 | 20.6 | −28.54 | 103.09 |
| 21E1640 | 20.8 | −28.51 | 102.56 |

(the values in the table includes the percent error according to the official method used) The measured values for the C14 activity of the samples of Pmc correspond to those for substances from purely bio-based carbon. There is no evidence of a synthetic source in the analysed material. The C14-activity value perfectly overlaps among batches as it is not affected by the biological variability of the starting materials, thus identifying high reproducibility of the production process according to conservation of this parameter.

On two batches of co-extract (20J1770 e 21E1640) a study of the isotopic abundance during different steps of the manufacturing process was conducted.

The results are reported in the table below depicting the δ ratio of the main isotopes of the coarse plant raw plant parts of the co-extract *Centella-Echinacea*.

| Description | $\delta^{18}O/^{16}O$ | $\delta^{13}C/^{12}C$ |
|---|---|---|
| Centella leaves, Batch 20H1282 | +20.8 | −28.57 |
| Echinacea roots, Batch 20F0840 | +22.7 | −28.17 |
| Mixture Centella leaves + Echinacea roots (batches above) | +20.9 | −28.86 |
| Batch 21E1640 (manufactured in presently used as clinical experimental batch) | +20.8 | −28.51 |
| Batch 20J1770 | +20.6 | −28.54 |

The assessment of the isotopic abundance of the materials along the production process shows that the production process does not alter the abundance ratios, thus substantiating the fact that the process conserves the native biophysical characteristics of the starting materials.

Analysis for the batches under study showed substantial similarity of values and maintenance of ratios during the manufacturing process. This is consistent with the NIR results previously described, according to which all batches were similar and merged without outliers to similar spectra.

5. RNA Evaluation in Production Intermediate

Biophysical characterization of biological vegetal material includes the evaluation of biological material in production intermediates.

"RIC199EL0, extract BLEND CENT_ECH EL, batch.R20I4716" which corresponds to a production intermediate of Arté GX, i.e. the *Centella asiatica* and *Echinacea* water coextract in the proportions depicted in example 1, before ultrafiltration. The presence of RNA has been evaluated both quantitatively and qualitatively. RNA was extracted using a plant matrix specific kit (RNeasy PowerPlant kit) after homogenization with the use of QIAshredder columns before proceeding with the kit extraction protocol. The dimensional distribution of the RNA obtained was performed using Bioanalyzer 2100 with RNA 6000 Nano, RNA 6000 Pico and small RNA kits.

In FIG. 13, the electropherogram "A" shows the size distribution of the total RNA and the electropherogram "B" shows the RNA size distribution between 4 and 150 nt.

Then, to quantitatively assess the total RNA extracted from the sample, a nucleic acid digestion was performed using the New England Biolabs nucleoside digestion Mix kit. The RNA concentration was expressed as total nucleosides by UHPLC-qToF analysis. The Table below reports RNA expressed as total nucleosides.

| BLEND CENT_ECH EL | | |
|---|---|---|
| | μg/g | % |
| Guanosine | 9.20 | 41.39 |
| Adenosine | 3.51 | 15.79 |
| Uridine | 2.06 | 9.27 |
| Cytidine | 7.46 | 33.56 |
| Total | 22.23 | 100 |

These observations, in addition to providing a method for validating the biological origin of a matrix, identify an additional degree of both structural and functional complexity to be taken into account in product management.

For a prompt reference and confrontation, the experimental protocols used for the three different products described in example 1 are summarised in the table hereinbelow.

| | Arté GX (reference model) | PRODUCT B | PRODUCT C |
|---|---|---|---|
| CELL BASED ASSAY | 2. In vitro cell assay representative of Osteoarthritis An in vitro cellular model capable of recapitulating features of osteoarthritis [1-3] was established by exposing primary human chondrocytes (HC, Cell Application INC 402K-05) to IL1B [5 ng/ml] for 6 hours followed by 24 hours of exposure to five different batches of "Arté-Gx" [1.4 mg/ml]: Batch 20B1955 (gold standard) Batch 20I1279 Batch 20J1770 Batch 21E1640 Batch 20B0596 Batch 21E1640 Dest Each time one of the batch solutions was added, fresh IL1B [5 ng/ml] was also added to the medium. | Human SH-SY5Y (ATCC® No. CRL-2266™) neuroblastoma cells are a commonly used as a neuronal model, as they maintain several neuron markers [Barbosa, D.J .; Capela, J.P.; de Lourdes Bastos, M.; Carvalho, F. In vitro models for neurotoxicology research. [Toxicol. Res. 2015, 4, 801-842]. The cells were exposed for 24 hours to product B at 1.07 mg/ml in the appropriate cell culture medium. | Human, adipocyte-derived, mesenchymal stem cell lines (hADMSC), capable of differentiating into osteoblasts and mineralize the extracellular matrix (ECM) were used in this study. These cells were obtained during general surgery from three different patients (PA42, PA59 and PA69) (Romagnoli et al, "In Vitro Behavior of Human Adipose Tissue-Derived Stem Cells on Poly(ε-caprolactone) Film for Bone Tissue Engineering Applications", BioMed Research International, vol. 2015, Article ID 323571, 12 pages, 2015. https://doi.org/10.1155/2015/323571). These cell lines have been characterized with respect to the main stemness markers of mesenchymal stem cells (CD44, CD105, and STRO1) and by studying their multipotency toward osteogenic phenotypes at the Department of Surgery and Translational medicine of the University of Florence. hADMSCs were cultured in a growth medium (GM) and grown to 70-80% confluence. Afterwards, the cells were seeded in 24-well plate at a concentration of $1 \times 10^5$ cells/well. After a week, the GM was replaced with osteogenic medium (OM) containing the fluorophore calcein 1 µg/mL and incubated for 28 days with or without product C. The medium with or without the product C was refreshed twice a week. |
| DEFINITION OF THE PATHO-PHYSIOLOGICAL HALLMARKS OF THE DISEASE WITH WHICH TO INTERROGATE IPA | The patho-physiological features of state-of-the-art "Osteoarthritis condition" were considered with particular attention to the following areas involved: -inflammatory process, -cellular proliferation, -anatomical damage, -oxidative stress This knowledge was used to interrogate IPA via the "IPA Bioprofiler" tool, using the following keywords: osteoarthritis, arthropathy, formation of cartilage tissue, destruction of cartilage tissue, damage of cartilage, connective tissue disorder, inflammation of joint, immune cell trafficking. | The alteration of healthy physiological state features of state-of-the-art "Mild Cognitive Impairment" were considered with particular attention to the following areas involved: -Cognition -Activation and viability -Myelination and branching -Reduction of inflammation -Skeletal and muscular system function This knowledge was used to interrogate IPA via the "IPA Bioprofiler" tool, using the following keywords: neurodegeneration, cognitive deficit, memory deficit, function of muscle, oxidative stress and inflammatory process. | The alteration of healthy physiological state features of state-of-the-art "Osteoporosis" were considered with particular attention to the following areas involved: - Remodelling of bone - Osteoporosis - Differentiation of osteoblasts - Mineralization - Reduction of inflammation - Reduction of bone adipose tissue This knowledge was used to interrogate IPA via the "IPA Bioprofiler" tool, using the following keywords: osteoporosis, postmenopausal osteoporosis, calcification of bone, osteoblast and osteoclast differentiation, bone mineral density. |
| GENE EXPRESSION ANALYSIS | 2.1.2. Gene expression analysis At the end of described treatment periods, cells were washed with 100 µl PBS and lysed and collected in RLT buffer | At the end of described treatment periods, cells were washed with 100 µl PBS and lysed and collected in RLT | 2.1.2. Gene expression analysis At the end of described treatment periods, cells were washed with 100 µl PBS and lysed and |

-continued

| | Arté GX (reference model) | PRODUCT B | PRODUCT C |
|---|---|---|---|
| | (Qiagen, 1053393) added with ß-mercaptoethanol (Sigma, M3148) and DX reagent (Qiagen, 19088) for gene expression analysis experiments. Total RNA was extracted from cells lysates using an QIAsymphony RNA Kit (Qiagen,) with the QIAsymphony SP instrument (Qiagen). The quality and quantity of RNA was determined by A230, A260, A280 and A320 measurements on Varioskan™ LUX multimode microplate reader (Thermo Scientific™). Integrity of RNA was checked using a 2100 expert_Eukaryote Total RNA Nano Kit (Agilent). Whole transcriptome expression profile was evaluated using a Human Clariom™ S Pico Assay HT (Applied Biosystems, ThermoFisher Scientific) on a GeneTitan MC Instrument (Applied Biosystems, ThermoFisher Scientific), following the manufacturer's instructions. Briefly, 6 ng of total RNA was used to generate cDNA, then fragmented and labelled cDNA was hybridized to a Human Clariom S 96-array plate for 17 h at 45° C. Arrays were washed, stained and then scanned using the GeneTitan MC Instrument (Applied Biosystems, ThermoFisher Scientific) and CEL Intensity files were generated by Affymetrix GeneChip Command Console Software (AGCC, ThermoFisher Scientific). | buffer (Qiagen, 1053393) added with ß-mercaptoethanol (Sigma, M3148) and DX reagent (Qiagen, 19088) for gene expression analysis experiments. Total RNA was extracted from cells lysates using an QIAsymphony RNA Kit (Qiagen,) with the QIAsymphony SP instrument (Qiagen). The quality and quantity of RNA was determined by A230, A260, A280 and A320 measurements on Varioskan™ LUX multimode microplate reader (Thermo Scientific™). Integrity of RNA was checked using a 2100 expert_Eukaryote Total RNA Nano Kit (Agilent). Whole transcriptome expression profile was evaluated using RNA-Seq data obtained with Illumina NextSeq, sequenced in paired-end mode. | collected in RLT buffer (Qiagen, 1053393) added with ß-mercaptoethanol (Sigma, M3148) and DX reagent (Qiagen, 19088) for gene expression analysis experiments. Total RNA was extracted from cells lysates using an QIAsymphony RNA Kit (Qiagen,) with the QIAsymphony SP instrument (Qiagen). The quality and quantity of RNA was determined by A230, A260, A280 and A320 measurements on Varioskan™ LUX multimode microplate reader (Thermo Scientific™). Integrity of RNA was checked using a 2100 expert_Eukaryote Total RNA Nano Kit (Agilent). Whole transcriptome expression profile was evaluated using a Human Clariom™ S Pico Assay HT (Applied Biosystems, ThermoFisher Scientific) on a GeneTitan MC Instrument (Applied Biosystems, ThermoFisher Scientific), following the manufacturer's instructions. Briefly, 6 ng of total RNA was used to generate cDNA, then fragmented and labelled cDNA was hybridized to a Human Clariom S 96-array plate for 17 h at 45° C. Arrays were washed, stained and then scanned using the GeneTitan MC Instrument (Applied Biosystems, ThermoFisher Scientific) and CEL Intensity files were generated by Affymetrix GeneChip Command Console Software (AGCC, ThermoFisher Scientific). |
| TRANSCRIPTOMICS DATA ANALYSIS | 2.1.3. Transcriptomics data analysis Data analysis was performed using Transcriptomic Analysis Console Software (TAC, ThermoFisher Scientific) that provides quality control analysis, performs normalization and summarization, based on the Signal Space Transformation-Robust Multi-Chip Analysis (SST-RMA) analysis algorithm, and provides a list of differentially expressed genes (Limma Bioconductor package, p-value ≤ 0.05). | Sample was mapped on reference genome using the bioinformatics tool STAR (version 2.7.0f), with the standard parameters for paired reads. The reference track was the assembly Human obtained from GenCode (HG38). The quantification of transcripts expressed for each sequenced samples was performed using featureCount algorithm. R was used to create a matrix of all genes expressed in all samples with the | 2.1.3. Transcriptomics data analysis Data analysis was performed using Transcriptomic Analysis Console Software (TAC, ThermoFisher Scientific) that provides quality control analysis, performs normalization and summarization, based on the Signal Space Transformation-Robust Multi-Chip Analysis (SST-RMA) analysis algorithm, and provides a list of differentially expressed genes (Limma Bioconductor package, p-value ≤ 0.05). |

-continued

| Arté GX (reference model) | PRODUCT B | PRODUCT C |
|---|---|---|
| | corresponding read-counts and the Bioconductor package DESeq2 was used to normalize the data, using the median of ratio, to perform the differential expression analysis. Quality control check such as Euclidean distances (Heatmap Distances) and Principal component analysis (PCA) were performed among all samples in each condition considered. | |

5. Conclusions

Taken together, the data here reported allow to identify acceptability parameters which are key in order to guarantee the quality of the production process of a product comprising or consisting of one or more matrix of biological origin (natural matrix). Intriguingly, the data shows that monitoring exclusively the reproducibility of the composition at the molecular level does not represent a rewarding strategy, as such a strategy ignores key features of the matrix that impact its ability to induce a reproducible effect when this is used to treat a biological system. Presumably due to the presence of redundancy effects between molecular components at both the structural and functional levels, and due to the presence of a network of physical and functional interactions within the complex matrix, its biological activity strongly depends on features better monitored by analysing carefully selected biophysical properties of the matrix.

Very eloquently, the exclusive use of targeted metabolomics data, especially when judged according to the principles usually reserved to single APIs, is not capable of intercepting the capability of different batches of the same product to elicit reproducible biological effects (see FIG. 5 vs FIGS. 3 and 4). By applying targeted metabolomics alone, such batches are incorrectly perceived as unacceptably different from one another. In contrast, the application of techniques monitoring features of the matrix that are emergent and deriving from networks of interactions, therefore different from and only partially dependent on conservation of the single molecular components, as disclosed in the present application, correctly identifies a satisfactory degree of similarity between the different batches analysed and express consistency with the fact that they indeed elicit reproducible, desirable biological effects.

The invention claimed is:

1. A method for defining the acceptability values of near infrared spectroscopy spectra for the validation of one or more different test batches of a product, for the treatment of cognitive impairment, wherein the product comprises extracts of *Melissa officinalis* dry leaves and blueberry, royal jelly, blueberry juice, apple juice, lemon juice, *Malpighia emarginata* juice, *Sambucus nigrum* juice, and honey; said method comprising:

(a) performing at least one in vitro cell-based assay on a reference standard of said product, wherein said assay comprises exposing neuroblastoma cells to the reference standard, wherein the reference standard has a known therapeutic effect for treatment of cognitive impairment, and a reference drug for treatment of cognitive impairment, wherein the read-out of said cell-based assay is representative of the modulation of a biological activity associated with one or more hallmarks of cognitive impairment;

(b) performing said in vitro cell-based assay on one or more test batches of said product;

(c) quantifying as Z-scores the modulation induced by each sample tested in steps (a) and (b) for each cell-based assay readout;

(d) defining as acceptable the Z-scores of the one or more different test batches that induce a modulation of each of measured biological activity in said cell-based assay that is at least equal to the Z-score of the reference product and defining as non-acceptable the Z-score of the one or more different batches that induce a modulation of at least one of said biological activities in said cell-based assay that is less than the Z-score of the reference product;

(e) performing near infrared spectroscopy on said reference standard and on said one or more different test batches; and (f) defining the acceptability values of the near infrared spectroscopy spectra of said one or more different test batches as the variability of the spectra between said acceptable batches and of said reference standard.

2. The method of claim 1, further comprising determining the biomarkers and/or biomarker modulation pattern associated with one or more hallmarks of cognitive impairment with said product in both healthy and diseased states.

3. The method of claim 2, wherein said biomarkers and/or biomarker modulation pattern correspond to the genes and expression pattern detectable in cognitive impairment for each read-out of the cell-based assay.

4. The method of claim 1, wherein said product is in a dry or lyophilized form.

5. The method of claim 1, further comprising performing near infrared spectroscopy on one or more known non-acceptable batches of said product and confirming that said one or more non-acceptable batches do not result produce a spectra within the acceptability ranges defined in step (e).

6. A method for compliance validation of one or more different test batches of a product for the treatment of cognitive impairment, wherein the product comprises extracts of *Melissa officinalis* dry leaves and blueberry, royal jelly, blueberry juice, apple juice, lemon juice, *Malpighia emarginata* juice, *Sambucus nigrum* juice, and honey; said method comprising:

(a) performing near infrared spectroscopy of each test batch, (b) performing at least one in vitro cell-based assay on a reference standard of said product, wherein said cell-based assay comprises exposing neuroblastoma cells to the reference standard, and wherein the reference standard has a known therapeutic effect for treatment of cognitive impairment, and on one or more test batches of said product, wherein the read-out of said cell-based assay is representative of the modulation of a biological activity associated with one or more hallmarks of said pathological condition;

(c) quantifying as Z-scores the modulation induced by each sample tested in step (b) for each cell-based assay readout;

(d) defining as acceptable the Z-scores of the one or more different test batches that induce a modulation of each of measured biological activity in said cell-based assay that is at least equal to the Z-score of the reference product and defining as non-acceptable the Z-score of the one or more different batches that induce a modulation of at least one of said biological activities in said cell-based assay that is less than the Z-score of the reference product;

(e) performing near infrared spectroscopy on said reference standard and on said one or more different test batches; and (f) defining the acceptability values of the near infrared spectroscopy spectra of said one or more different test batches as the variability of the spectra between said acceptable batches and of said reference standard; and (g) validating each test batch for which the obtained spectrum satisfies the acceptability ranges or cut-offs identified in step (f).

7. The method of claim 6, further comprising determining the biomarkers and/or biomarker modulation pattern associated with one or more hallmarks of cognitive impairment to be treated with said product in both healthy and diseased states.

8. The method of claim 7, wherein said biomarkers and/or biomarker modulation pattern correspond to the genes and expression pattern detectable in cognitive impairment for each read-out of the cell-based assay.

9. The method of claim 6, wherein said product is in a dry or lyophilized form.

10. The method of claim 6, further comprising performing near infrared spectroscopy on one or more known non-acceptable batches of said product and confirming that said one or more non-acceptable batches do not result produce a spectra within the acceptability ranges defined in step (e).

* * * * *